US012753407B2

(12) United States Patent
Cardia et al.

(10) Patent No.: US 12,753,407 B2
(45) Date of Patent: Oct. 6, 2026

(54) CHEMICALLY MODIFIED OLIGONUCLEOTIDES TARGETING BROMODOMAIN CONTAINING PROTEIN 4 (BRD4) FOR IMMUNOTHERAPY

(71) Applicant: Phio Pharmaceuticals Corp., King of Prussia, PA (US)

(72) Inventors: James Cardia, Franklin, MA (US); Rolf Kiessling, Stockholm (SE); Jeroen Melief, Sollentuna (SE)

(73) Assignee: Phio Pharmaceuticals Corp., King of Prussia, PA (US)

( * ) Notice: Subject to any disclaimer, the term of this patent is extended or adjusted under 35 U.S.C. 154(b) by 1064 days.

(21) Appl. No.: 17/775,148

(22) PCT Filed: Nov. 6, 2020

(86) PCT No.: PCT/US2020/059512
§ 371 (c)(1),
(2) Date: May 6, 2022

(87) PCT Pub. No.: WO2021/092464
PCT Pub. Date: May 14, 2021

(65) Prior Publication Data

US 2023/0002766 A1 Jan. 5, 2023

Related U.S. Application Data

(60) Provisional application No. 62/932,813, filed on Nov. 8, 2019.

(51) Int. Cl.
*C12N 15/113* (2010.01)
*A61P 35/00* (2006.01)

(52) U.S. Cl.
CPC ............ *C12N 15/113* (2013.01); *A61P 35/00* (2018.01); *C12N 2310/14* (2013.01); *C12N 2310/315* (2013.01); *C12N 2310/321* (2013.01); *C12N 2310/322* (2013.01); *C12N 2310/3515* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,201,860 | A | 5/1980 | Naito et al. |
| 4,415,732 | A | 11/1983 | Caruthers et al. |
| 4,426,330 | A | 1/1984 | Sears |
| 4,897,355 | A | 1/1990 | Eppstein et al. |
| 4,904,582 | A | 2/1990 | Tullis |
| 4,958,013 | A | 9/1990 | Letsinger |
| 5,013,556 | A | 5/1991 | Woodle et al. |
| 5,023,243 | A | 6/1991 | Tullis |
| 5,051,257 | A | 9/1991 | Pietronigro |
| 5,053,228 | A | 10/1991 | Mori et al. |
| 5,108,921 | A | 4/1992 | Low et al. |
| 5,112,963 | A | 5/1992 | Pieles et al. |
| 5,151,510 | A | 9/1992 | Stec et al. |
| 5,162,115 | A | 11/1992 | Pietronigro |
| 5,188,897 | A | 2/1993 | Suhadolnik et al. |
| 5,213,804 | A | 5/1993 | Martin et al. |
| 5,227,170 | A | 7/1993 | Sullivan |
| 5,264,423 | A | 11/1993 | Cohen et al. |
| 5,264,562 | A | 11/1993 | Matteucci |
| 5,284,656 | A | 2/1994 | Platz et al. |
| 5,354,844 | A | 10/1994 | Beug et al. |
| 5,356,633 | A | 10/1994 | Woodle et al. |
| 5,405,939 | A | 4/1995 | Suhadolnik |
| 5,416,016 | A | 5/1995 | Low et al. |
| 5,416,203 | A | 5/1995 | Letsinger |
| 5,417,978 | A | 5/1995 | Tari et al. |
| 5,432,272 | A | 7/1995 | Benner |
| 5,451,569 | A | 9/1995 | Wong et al. |
| 5,453,496 | A | 9/1995 | Caruthers et al. |
| 5,459,127 | A | 10/1995 | Felgner et al. |
| 5,459,255 | A | 10/1995 | Cook et al. |
| 5,466,786 | A | 11/1995 | Buhr et al. |
| 5,470,967 | A | 11/1995 | Huie et al. |
| 5,486,603 | A | 1/1996 | Buhr |
| 5,489,677 | A | 2/1996 | Sanghvi et al. |
| 5,495,009 | A | 2/1996 | Matteucci et al. |

(Continued)

FOREIGN PATENT DOCUMENTS

| | | | |
|---|---|---|---|
| AU | 2004206255 | B2 | 8/2004 |
| CN | 1 568 373 | A | 1/2005 |

(Continued)

OTHER PUBLICATIONS

Fakhr et al. Cancer Gene Therapy 2016 23, 73-82 (Year: 2016).*
Watts et al., Journal of Pathology 226:365-379 (Year: 2012).*
GenBank NM_014299.2.1 *Homo sapiens* bromodomain containing 4, transcript variant short, mRNA, pp. 1-6, retrieved on-line Dec. 9, 2025 from National Library of Medicine (Year: 2020).*
Amarzguioui et al., Approaches for chemically synthesized siRNA and vector-mediated RNAi. FEBS Lett. Oct. 31, 2005;579(26):5974-81. doi: 10.1016/j.febslet.2005.08.070. Epub Sep. 20, 2005.

(Continued)

*Primary Examiner* — Brian Whiteman
(74) *Attorney, Agent, or Firm* — Wolf, Greenfield & Sacks, P.C.

(57) ABSTRACT

The disclosure relates, in some aspects, to methods and compositions for production of immunomodulatory compositions. In some embodiments, the disclosure provides host cells which have been treated ex vivo with one or more oligonucleotide agents capable of controlling and/or reducing the differentiation of the host cell. In some embodiments, compositions and methods described by the disclosure are useful as immunogenic modulators for treating cancer.

16 Claims, 10 Drawing Sheets

Specification includes a Sequence Listing.

(56) References Cited

U.S. PATENT DOCUMENTS 5,514,786 A 5/1996 Cook et al.
5,527,528 A 6/1996 Allen et al.
5,532,130 A 7/1996 Alul
5,534,259 A 7/1996 Zalipsky et al.
5,556,948 A 9/1996 Tagawa et al.
5,561,225 A 10/1996 Maddry et al.
5,578,718 A 11/1996 Cook et al.
5,580,731 A 12/1996 Chang et al.
5,580,972 A 12/1996 Tu et al.
5,583,020 A 12/1996 Sullivan
5,587,469 A 12/1996 Cook et al.
5,591,721 A 1/1997 Agrawal et al.
5,591,722 A 1/1997 Montgomery et al.
5,591,843 A 1/1997 Eaton
5,594,121 A 1/1997 Froehler et al.
5,596,086 A 1/1997 Matteucci et al.
5,596,091 A 1/1997 Switzer
5,599,797 A 2/1997 Cook et al.
5,602,240 A 2/1997 De Mesmaeker et al.
5,607,923 A 3/1997 Cook et al.
5,614,617 A 3/1997 Cook et al.
5,614,621 A 3/1997 Ravikumar et al.
5,623,070 A 4/1997 Cook et al.
5,625,050 A 4/1997 Beaton et al.
5,633,360 A 5/1997 Bischofberger et al.
5,643,889 A 7/1997 Suhadolnik et al.
5,646,126 A 7/1997 Cheng et al.
5,646,265 A 7/1997 McGee
5,658,731 A 8/1997 Sproat et al.
5,661,134 A 8/1997 Cook et al.
5,663,312 A 9/1997 Chaturvedula
5,670,633 A 9/1997 Cook et al.
5,681,940 A 10/1997 Wang et al.
5,681,941 A 10/1997 Cook et al.
5,684,143 A 11/1997 Gryaznov et al.
5,700,920 A 12/1997 Altmann et al.
5,750,666 A 5/1998 Caruthers et al.
5,770,713 A 6/1998 Imbach et al.
5,777,153 A 7/1998 Lin et al.
5,789,416 A 8/1998 Lum et al.
5,792,847 A 8/1998 Buhr et al.
5,808,023 A 9/1998 Sanghvi et al.
5,814,014 A 9/1998 Elsberry et al.
5,817,781 A 10/1998 Swaminathan et al.
5,830,430 A 11/1998 Unger et al.
5,830,653 A 11/1998 Froehler et al.
5,856,455 A 1/1999 Cook
5,914,396 A 6/1999 Cook et al.
5,945,521 A 8/1999 Just et al.
5,948,767 A 9/1999 Scheule et al.
5,969,116 A 10/1999 Martin
5,976,567 A 11/1999 Wheeler et al.
5,981,501 A 11/1999 Wheeler et al.
5,986,083 A 11/1999 Dwyer et al.
6,001,841 A 12/1999 Cook et al.
6,005,094 A 12/1999 Simon et al.
6,005,096 A 12/1999 Matteucci et al.
6,013,786 A 1/2000 Chen
6,015,886 A 1/2000 Dale et al.
6,020,475 A 2/2000 Capaldi et al.
6,020,483 A 2/2000 Beckvermit et al.
6,028,183 A 2/2000 Lin et al.
6,043,352 A 3/2000 Manoharan et al.
6,051,699 A 4/2000 Ravikumar
6,093,180 A 7/2000 Elsberry
6,107,094 A 8/2000 Crooke
6,111,085 A 8/2000 Cook et al.
6,121,437 A 9/2000 Guzaev
6,153,737 A 11/2000 Manoharan et al.
6,207,819 B1 3/2001 Manoharan et al.
6,242,594 B1 6/2001 Kelly
6,248,878 B1 6/2001 Matulic-Adamic et al.
6,271,358 B1 8/2001 Manoharan et al.
6,300,319 B1 10/2001 Manoharan
6,326,358 B1 12/2001 Manoharan
6,331,617 B1 12/2001 Weeks et al.
6,333,152 B1 12/2001 Vogelstein et al.
6,335,434 B1 1/2002 Guzaev et al.
6,355,787 B1 3/2002 Beckvermit et al.
6,358,931 B1 3/2002 Cook et al.
6,395,492 B1 5/2002 Manoharan et al.
6,399,754 B1 6/2002 Cook
6,410,702 B1 6/2002 Swaminathan et al.
6,420,549 B1 7/2002 Cook et al.
6,432,963 B1 8/2002 Hisamichi et al.
6,440,943 B1 8/2002 Cook et al.
6,444,806 B1 9/2002 Veerapanani et al.
6,455,586 B1 9/2002 Kaplan et al.
6,465,628 B1 10/2002 Ravikumar et al.
6,476,205 B1 11/2002 Buhr et al.
6,506,559 B1 1/2003 Fire et al.
6,525,031 B2 2/2003 Manoharan
6,528,631 B1 3/2003 Cook et al.
6,531,584 B1 3/2003 Cook et al.
6,673,611 B2 1/2004 Thompson et al.
6,683,167 B2 1/2004 Meteley et al.
6,815,432 B2 11/2004 Wheeler et al.
6,849,726 B2 2/2005 Usman et al.
6,858,225 B2 2/2005 Semple et al.
6,887,906 B1 5/2005 Teng et al.
7,041,824 B2 5/2006 Bordon-Pallier et al.
7,056,704 B2 6/2006 Tuschl et al.
7,078,196 B2 7/2006 Tuschl et al.
7,148,342 B2 12/2006 Tolentino et al.
7,205,297 B2 4/2007 Beauchamp et al.
7,345,027 B2 3/2008 Tolentino et al.
7,432,250 B2 10/2008 Crooke
7,521,431 B2 4/2009 Reich et al.
7,538,095 B2 5/2009 Fire et al.
7,560,438 B2 7/2009 Fire et al.
7,595,387 B2 9/2009 Leake et al.
7,622,633 B2 11/2009 Fire et al.
7,629,321 B2 12/2009 Crooke
7,645,744 B2 1/2010 Reich et al.
7,674,895 B2 3/2010 Tolentino et al.
7,695,902 B2 4/2010 Crooke
7,745,608 B2 6/2010 Manoharan et al.
7,750,143 B2 7/2010 Tolentino et al.
7,750,144 B2 7/2010 Zamore et al.
7,786,290 B2 8/2010 Woppmann et al.
7,807,814 B2 10/2010 Reich et al.
7,829,693 B2 11/2010 Kreutzer et al.
7,847,090 B2 12/2010 Reich et al.
7,872,118 B2 1/2011 Reich et al.
7,994,305 B2 8/2011 Reich et al.
8,110,674 B2 2/2012 Manoharan et al.
8,168,600 B2 5/2012 Dokka et al.
8,193,163 B2 6/2012 Reich et al.
8,202,845 B2 6/2012 Drumm et al.
8,227,444 B2 7/2012 Dejneka
8,236,775 B2 8/2012 Reich et al.
8,263,569 B2 9/2012 Baulcombe et al.
8,470,792 B2 6/2013 Frost et al.
8,541,384 B2 9/2013 Tolentino et al.
8,546,345 B2 10/2013 Tolentino et al.
8,664,189 B2 3/2014 Khvorova et al.
8,796,443 B2 8/2014 Khvorova et al.
8,815,818 B2 8/2014 Samarsky et al.
8,946,180 B2 2/2015 Drumm et al.
8,946,403 B2 2/2015 Tolentino et al.
9,074,211 B2 7/2015 Woolf et al.
9,080,171 B2 7/2015 Khvorova et al.
9,095,504 B2 8/2015 Libertine et al.
9,150,863 B2 10/2015 Tolentino et al.
9,175,289 B2 11/2015 Khvorova et al.
9,222,092 B2 12/2015 Giese et al.
9,303,259 B2 4/2016 Khvorova et al.
9,340,786 B2 5/2016 Khvorova et al.
9,493,774 B2 11/2016 Kamens et al.
9,745,574 B2 8/2017 Woolf et al.
9,938,530 B2 4/2018 Khvorova et al.
9,963,702 B2 5/2018 Khvorova et al.
10,041,073 B2 8/2018 Khvorova et al.
10,131,904 B2 11/2018 Pavco et al.

(56) References Cited

U.S. PATENT DOCUMENTS

| | | | |
|---|---|---|---|
| 10,138,485 | B2 | 11/2018 | Khvorova et al. |
| 10,167,471 | B2 | 1/2019 | Kamens et al. |
| 10,184,124 | B2 | 1/2019 | Libertine et al. |
| 10,240,149 | B2 | 3/2019 | Khvorova et al. |
| 10,300,027 | B2 | 5/2019 | Levis et al. |
| 10,479,992 | B2 | 11/2019 | Woolf et al. |
| 10,633,654 | B2 | 4/2020 | Pavco et al. |
| 10,662,430 | B2 | 5/2020 | Libertine et al. |
| 10,774,330 | B2 | 9/2020 | Khvorova et al. |
| 10,808,247 | B2 | 10/2020 | Byrne et al. |
| 10,815,485 | B2 | 10/2020 | Khvorova et al. |
| 10,876,119 | B2 | 12/2020 | Khvorova et al. |
| 10,900,039 | B2 | 1/2021 | Cauwenbergh |
| 10,913,948 | B2 | 2/2021 | Khvorova et al. |
| 10,934,550 | B2 | 3/2021 | Wolfson et al. |
| 11,001,845 | B2 | 5/2021 | Cardia et al. |
| 11,021,707 | B2 | 6/2021 | Cardia et al. |
| 11,118,178 | B2 | 9/2021 | Khvorova et al. |
| 11,254,940 | B2 | 2/2022 | Woolf et al. |
| 11,279,934 | B2 | 3/2022 | Byrne et al. |
| 11,396,654 | B2 | 7/2022 | Khvorova et al. |
| 12,296,009 | B2 | 5/2025 | Melief et al. |
| 12,544,344 | B2 | 2/2026 | Maxwell et al. |
| 2002/0081736 | A1 | 6/2002 | Conroy et al. |
| 2002/0132788 | A1 | 9/2002 | Lewis et al. |
| 2002/0147332 | A1 | 10/2002 | Kaneko et al. |
| 2002/0160393 | A1 | 10/2002 | Symonds et al. |
| 2002/0162126 | A1 | 10/2002 | Beach et al. |
| 2003/0004325 | A1 | 1/2003 | Cook et al. |
| 2003/0027780 | A1 | 2/2003 | Hardee et al. |
| 2003/0077829 | A1 | 4/2003 | MacLachlan |
| 2003/0108923 | A1 | 6/2003 | Tuschl et al. |
| 2003/0139585 | A1 | 7/2003 | Uhlmann et al. |
| 2003/0148979 | A1 | 8/2003 | Sosnowski et al. |
| 2003/0157030 | A1 | 8/2003 | Davis et al. |
| 2003/0158403 | A1 | 8/2003 | Manoharan et al. |
| 2003/0166282 | A1 | 9/2003 | Brown et al. |
| 2004/0009938 | A1 | 1/2004 | Manoharan et al. |
| 2004/0014957 | A1 | 1/2004 | Eldrup et al. |
| 2004/0018999 | A1 | 1/2004 | Beach et al. |
| 2004/0054155 | A1 | 3/2004 | Woolf et al. |
| 2004/0072785 | A1 | 4/2004 | Wolff et al. |
| 2004/0137471 | A1 | 7/2004 | Vickers et al. |
| 2004/0167090 | A1 | 8/2004 | Monahan et al. |
| 2004/0171033 | A1 | 9/2004 | Baker et al. |
| 2004/0180351 | A1 | 9/2004 | Giese et al. |
| 2004/0192629 | A1 | 9/2004 | Xu et al. |
| 2004/0204377 | A1 | 10/2004 | Rana et al. |
| 2004/0219520 | A1 | 11/2004 | Mirkin et al. |
| 2004/0229266 | A1 | 11/2004 | Tuschl et al. |
| 2004/0241845 | A1 | 12/2004 | Desgroseillers et al. |
| 2004/0248839 | A1 | 12/2004 | Kowalik et al. |
| 2004/0259247 | A1 | 12/2004 | Tuschl et al. |
| 2005/0020521 | A1 | 1/2005 | Rana et al. |
| 2005/0032733 | A1 | 2/2005 | McSwiggen et al. |
| 2005/0042227 | A1 | 2/2005 | Zankel et al. |
| 2005/0080246 | A1 | 4/2005 | Allerson et al. |
| 2005/0107325 | A1 | 5/2005 | Manoharan et al. |
| 2005/0142535 | A1 | 6/2005 | Damha et al. |
| 2005/0181382 | A1 | 8/2005 | Zamore et al. |
| 2005/0245474 | A1 | 11/2005 | Baker et al. |
| 2005/0246794 | A1 | 11/2005 | Khvorova et al. |
| 2005/0255487 | A1 | 11/2005 | Khvorova et al. |
| 2005/0281781 | A1 | 12/2005 | Ostroff |
| 2006/0009409 | A1 | 1/2006 | Woolf |
| 2006/0069050 | A1 | 3/2006 | Rana |
| 2006/0127891 | A1 | 6/2006 | McSwiggen et al. |
| 2006/0142228 | A1 | 6/2006 | Ford et al. |
| 2006/0160766 | A1 | 7/2006 | Cheung |
| 2006/0178324 | A1 | 8/2006 | Hadwiger et al. |
| 2006/0178327 | A1 | 8/2006 | Yeung |
| 2006/0211766 | A1 | 9/2006 | Kaplan et al. |
| 2007/0032441 | A1 | 2/2007 | McSwiggen et al. |
| 2007/0166734 | A1 | 7/2007 | Bhat et al. |
| 2007/0173473 | A1 | 7/2007 | McSwiggen et al. |
| 2007/0173476 | A1 | 7/2007 | Leake et al. |
| 2007/0231392 | A1 | 10/2007 | Wagner et al. |
| 2007/0248659 | A1 | 10/2007 | Shanahan et al. |
| 2007/0254850 | A1 | 11/2007 | Lieberman et al. |
| 2007/0269889 | A1 | 11/2007 | Leake et al. |
| 2008/0071068 | A1 | 3/2008 | Oba et al. |
| 2008/0085869 | A1 | 4/2008 | Yamada et al. |
| 2008/0293593 | A1 | 11/2008 | Khvorova et al. |
| 2008/0311040 | A1 | 12/2008 | Berry et al. |
| 2009/0010948 | A1 | 1/2009 | Huang et al. |
| 2009/0023216 | A1 | 1/2009 | Woolf |
| 2009/0131360 | A1 | 5/2009 | Woolf et al. |
| 2009/0171075 | A1 | 7/2009 | Li |
| 2009/0208564 | A1 | 8/2009 | Li et al. |
| 2009/0220582 | A1 | 9/2009 | Min |
| 2009/0220583 | A1 | 9/2009 | Pereswetoff-Morath et al. |
| 2009/0239814 | A1 | 9/2009 | Manoharan et al. |
| 2009/0247608 | A1 | 10/2009 | Manoharan et al. |
| 2010/0040656 | A1 | 2/2010 | Franklin et al. |
| 2010/0069620 | A1 | 3/2010 | Zon |
| 2010/0136695 | A1 | 6/2010 | Woolf |
| 2010/0166707 | A1* | 7/2010 | Hunter ............... A61K 38/1709 435/6.12 |
| 2010/0286236 | A1 | 11/2010 | Schlingensiepen et al. |
| 2011/0251258 | A1 | 10/2011 | Samarsky et al. |
| 2011/0268761 | A1 | 11/2011 | Levis et al. |
| 2011/0294869 | A1 | 12/2011 | Petersen |
| 2012/0046186 | A1 | 2/2012 | Pelham et al. |
| 2013/0142875 | A1* | 6/2013 | Shemi .................. A61K 9/7007 424/484 |
| 2014/0030319 | A1 | 1/2014 | Tocque et al. |
| 2016/0152973 | A1 | 6/2016 | Jadhav et al. |
| 2016/0304875 | A1 | 10/2016 | Cauwenbergh et al. |
| 2016/0319278 | A1 | 11/2016 | Khvorova et al. |
| 2016/0355808 | A1 | 12/2016 | Khvorova et al. |
| 2016/0355826 | A1 | 12/2016 | Khvorova et al. |
| 2017/0051290 | A1 | 2/2017 | Byrne et al. |
| 2018/0263925 | A1 | 9/2018 | Cauwenbergh et al. |
| 2019/0029974 | A1 | 1/2019 | Cauwenbergh et al. |
| 2019/0218557 | A1 | 7/2019 | Kamens et al. |
| 2020/0085764 | A1 | 3/2020 | Maxwell et al. |
| 2020/0101028 | A1 | 4/2020 | Levis et al. |
| 2020/0215113 | A1 | 7/2020 | Eliseev |
| 2020/0308578 | A1 | 10/2020 | Woolf et al. |
| 2021/0024926 | A1 | 1/2021 | Khvorova et al. |
| 2021/0062195 | A1 | 3/2021 | Libertine et al. |
| 2021/0147849 | A1 | 5/2021 | Khvorova et al. |
| 2021/0261968 | A1 | 8/2021 | Khvorova et al. |
| 2021/0348166 | A1 | 11/2021 | Cauwenbergh |
| 2021/0348169 | A1 | 11/2021 | Cauwenbergh |
| 2023/0089478 | A1* | 3/2023 | Cardia ................. C12N 15/113 |
| 2024/0301430 | A1 | 9/2024 | Maxwell et al. |

FOREIGN PATENT DOCUMENTS

| | | | |
|---|---|---|---|
| CN | 101374528 | A | 2/2009 |
| CN | 105734058 | A | 7/2016 |
| DE | 197 27 932 | A1 | 1/1999 |
| EP | 0 552 766 | A2 | 7/1993 |
| EP | 1214 945 | A2 | 6/2002 |
| EP | 1 144 623 | B9 | 3/2003 |
| EP | 1 352 061 | B1 | 10/2003 |
| EP | 0 928 290 | B9 | 3/2005 |
| EP | 1 407 044 | B1 | 9/2007 |
| EP | 1 605 978 | B1 | 9/2010 |
| EP | 2592146 | A2 | 5/2013 |
| JP | 2004-500846 | | 1/2004 |
| JP | 4 095 895 | B2 | 9/2004 |
| JP | 2006-516288 | A | 6/2006 |
| JP | 2007-525169 | A | 9/2007 |
| JP | 2007-531520 | A | 11/2007 |
| JP | 2008-536874 | A | 9/2008 |
| JP | 2009-519033 | | 5/2009 |
| JP | 2016-540511 | A | 12/2016 |
| WO | WO 92/003464 | A1 | 3/1992 |
| WO | WO 94/023028 | A2 | 10/1994 |
| WO | WO 95/016466 | A1 | 6/1995 |
| WO | WO 95/023162 | A1 | 8/1995 |
| WO | WO 96/040964 | A2 | 12/1996 |

(56) References Cited

FOREIGN PATENT DOCUMENTS

| | | | | |
|---|---|---|---|---|
| WO | WO 99/013915 A1 | 3/1999 | | |
| WO | WO 99/060012 A1 | 11/1999 | | |
| WO | WO 01/085941 A2 | 11/2001 | | |
| WO | WO 03/012052 A2 | 2/2003 | | |
| WO | WO 2003/064626 A2 | 8/2003 | | |
| WO | WO 2003/087367 A2 | 10/2003 | | |
| WO | WO 2003/087368 A2 | 10/2003 | | |
| WO | WO 2004/064760 A2 | 8/2004 | | |
| WO | WO 2004/065600 A2 | 8/2004 | | |
| WO | WO 2004/065601 A2 | 8/2004 | | |
| WO | WO 2004/090105 A2 | 10/2004 | | |
| WO | WO 2005/019430 A2 | 3/2005 | | |
| WO | WO 2005/019453 A2 | 3/2005 | | |
| WO | WO 2005/059133 A2 | 6/2005 | | |
| WO | WO 2005/079533 A2 | 9/2005 | | |
| WO | WO 2005/097992 A2 | 10/2005 | | |
| WO | WO 2006/019430 A2 | 2/2006 | | |
| WO | WO 2006/039656 A2 | 4/2006 | | |
| WO | WO 2006/065601 A2 | 6/2006 | | |
| WO | WO 2006/092795 A2 | 9/2006 | | |
| WO | WO 2006/128141 A2 | 11/2006 | | |
| WO | WO 2007/021142 A1 | 2/2007 | | |
| WO | WO 2007/030167 A1 | 3/2007 | | |
| WO | WO 2007/069068 A2 | 6/2007 | | |
| WO | WO 2007/089607 A2 | 8/2007 | | |
| WO | WO 2008/021157 A1 | 2/2008 | | |
| WO | WO 2008/028965 A2 | 3/2008 | | |
| WO | WO 2008/028968 A2 | 3/2008 | | |
| WO | WO 2008/036825 A2 | 3/2008 | | |
| WO | WO 2008/094866 A1 | 8/2008 | | |
| WO | WO 2008/109353 A1 | 9/2008 | | |
| WO | WO 2008/125908 A2 | 10/2008 | | |
| WO | WO 2009/020344 A2 | 2/2009 | | |
| WO | WO 2009/029688 A3 | 3/2009 | | |
| WO | WO 2009/029690 A1 | 3/2009 | | |
| WO | WO 2009/044392 A2 | 4/2009 | | |
| WO | WO 2009/078685 A2 | 6/2009 | | |
| WO | WO 2009/126933 A2 | 10/2009 | | |
| WO | WO 2010/006237 A2 | 1/2010 | | |
| WO | WO 2010/027830 A2 | 3/2010 | | |
| WO | WO 2010/042281 A2 | 4/2010 | | |
| WO | WO 2011/143660 A2 | 11/2011 | | |
| WO | WO 2011/154542 A1 | 12/2011 | | |
| WO | WO 2012/112079 A1 | 8/2012 | | |
| WO | WO 2013/101436 A1 | 7/2013 | | |
| WO | WO 2014/076703 A1 | 5/2014 | | |
| WO | WO 2015/024986 A2 | 2/2015 | | |
| WO | WO 2015/084897 A2 | 6/2015 | | |
| WO | WO 2016/025880 A1 | 2/2016 | | |
| WO | WO 2016/161388 A1 | 10/2016 | | |
| WO | WO 2016/177343 A1 | 11/2016 | | |
| WO | WO 2017/173453 A1 | 10/2017 | | |
| WO | WO-2019032619 A1 * | 2/2019 | .......... | C12N 15/113 |
| WO | WO 2020/163222 A1 | 8/2020 | | |
| WO | WO 2022/245754 A1 | 11/2022 | | |
| WO | WO 2023/015265 A2 | 2/2023 | | |
| WO | WO 2023/130021 A1 | 7/2023 | | |
| WO | WO 2025/101204 A1 | 5/2025 | | |
| WO | WO 2025/117786 A1 | 6/2025 | | |

OTHER PUBLICATIONS

Boone et al., INTASYL™ self-delivering RNAi therapeutic targeting BRD4 elicits on-target apoptosis of human tumor cells. AACR-NCI-EORTC International Conference on Molecular Targets and Cancer Therapeutics. Boston, MA. Poster C107. Oct. 11, 2023.

Corey, Chemical modification: the key to clinical application of RNA interference? J Clin Invest. Dec. 2007; 117(12):3615-22. doi: 10.1172/JCI33483.

Cuiffo et al., INTASYL™ self-delivering RNAi therapy specifically dual targeting BRD4 and PD-1 elicits complete tumor responses and evidence of synergy in a subcutaneous Hepa1-6 model of murine hepatoma in C57BL/6N mice. 2021 American Society of Clinical Oncology (ASCO) Annual Meeting. Chicago, IL. Poster e14537. Accessible at https://meetings.asco.org/abstracts-presentations/200319. May 19, 2021.

Cuiffo et al., Local administration of BRD4-targeting self-delivering RNAi (PH-894) provides abscopal efficacy toward untreated distal tumors and potentiates the efficacy of systemic anti-PD-1 antibody therapy. American Association for Cancer Research (AACR) Annual Meeting 2022. New Orleans, LA. Poster #4237. Apr. 13, 2022.

Maxwell et al., INTASYL PH-894: Targeting BRD4 to Enhance NK Cell-Based Immunotherapy. ASGCT Advancing Gene + Cell Therapies for Cancer Conference. Sep. 16, 2024. Abstract.

Maxwell et al., INTASYL self-delivering RNAi: a flexible platform to treat dermatological malignancies. Society for Investigative Dermatology (SID) 2024 Annual Meeting. Dallas, TX. Poster 575. May 17, 2024.

Melief et al., Modulating BRD4 in T cells using self-delivery RNAi to improve adoptive cell therapy of cancer. Journal of Immuno Therapy of Cancer. Nov. 6, 2019;7(Suppl 1):P222. 34th Annual Meeting of the Society for Immunotherapy of Cancer. Abstract.

Podbevsek et al., Solution-state structure of a fully alternately 2'-F/2'-OMe modified 42-nt dimeric siRNA construct. Nucleic Acids Res. Nov. 2010;38(20):7298-307. doi: 10.1093/nar/gkq621. Epub Jul. 12, 2010.

Rana, Illuminating the silence: understanding the structure and function of small RNAs. Nat Rev Mol Cell Biol. Jan. 2007;8(1):23-36. doi: 10.1038/nrm2085.

Rivest et al., INTASYLTM PH-894 self-delivering RNAi targeting BRD4 enhances the antigenicity of melanoma cells through MART-1 upregulation. AACR-NCI-EORTC International Conference on Molecular Targets and Cancer Therapeutics. Boston, MA. Poster C109. Oct. 11, 2023.

Shmushkovich et al., Functional features defining the efficacy of cholesterol-conjugated, self-deliverable, chemically modified siRNAs. Nucleic Acids Res. Nov. 16, 2018;46(20):10905-10916. doi: 10.1093/nar/gky745.

Zheng et al., Activation of the protein kinase PKR by short double-stranded RNAs with single-stranded tails. RNA. Dec. 2004;10(12):1934-45. doi: 10.1261/rna.7150804.

Invitation to Pay Additional Fees for Application No. PCT/US2020/059512 mailed Feb. 19, 2021.

International Search Report and Written Opinion for Application No. PCT/US2020/059512 mailed May 27, 2021.

International Preliminary Report on Patentability for Application No. PCT/US2020/059512 mailed May 19, 2022.

[No Author Listed] RedChip Small-Cap Investor Conference. RXI Pharmaceuticals (Nasdaq RXII). Jun. 16, 2009.

[No Author Listed] RXi Pharmaceuticals Completes Apthera Acquisition. Press Release. Business Wire. Apr. 14, 2011. 2 pages.

[No Author Listed] RXi Pharmaceuticals Corporation. Ex 99.1. OTC: RXII. Mar. 2013. 38 pages.

[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

Akhtar et al., Interactions of antisense DNA oligonucleotide analogs with phospholipid membranes (liposomes). Nucleic Acids Res. Oct. 25, 1991;19(20):5551-9. doi: 10.1093/nar/19.20.5551.

Akinc et al., Development of lipidoid-siRNA formulations for systemic delivery to the liver. Mol Ther. May 2009;17(5):872-9. doi: 10.1038/mt.2009.36. Epub Mar. 3, 2009.

Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.

Aleckovic M, Carter D. RNAi at Oxford. J RNAi Gene Silencing. May 27, 2008;4(1):266-8.

Augustyns et al., Incorporation of hexose nucleoside analogues into oligonucleotides: synthesis, base-pairing properties and enzymatic stability. Nucleic Acids Res. Sep. 25, 1992;20(18):4711-6.

Baigude et al., Design and creation of new nanomaterials for therapeutic RNAi. ACS Chem Biol. Apr. 24, 2007;2(4):237-41.

(56) References Cited

OTHER PUBLICATIONS

Behlke M., Progress towards in vivo use of siRNAs. Mol Ther. Apr. 2006;13(4):644-70. doi: 10.1016/j.ymthe.2006.01.001. Epub Feb. 14, 2006.

Bjerke et al., Histone H3.3. mutations drive pediatric glioblastoma through upregulation of MYCN. Cancer Discov. May 2013;3(5):512-9.

Bongartz et al., Improved biological activity of antisense oligonucleotides conjugated to a fusogenic peptide. Nucleic Acids Res. Nov. 11, 1994;22(22):4681-8.

Borkner et al., RNA interference targeting programmed death receptor-1 improves immune functions of tumor-specific T cells. Cancer Immunol Immunother. Aug. 2010;59(8):1173-83. doi: 10.1007/s00262-010-0842-0. Epub Mar. 27, 2010.

Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.

Braasch et al., RNA interference in mammalian cells by chemically-modified RNA. Biochemistry. Jul. 8, 2003;42(26):7967-75.

Brenner et al., Adoptive T cell therapy of cancer. Curr Opin Immunol. Apr. 2010;22(2):251-7. doi: 10.1016/j.coi.2010.01.020. Epub Feb. 17, 2010.

Brown et al., RNAi off-targeting: Light at the end of the tunnel. J RNAi Gene Silencing. Jul. 28, 2006;2(2):175-7.

Byrne et al., Formulation and Release of sd-rxRNA® from a Cross-linked, Thiolated CMHA-based Film for Topical Delivery to Reduce the Formation of Corneal Scarring. RXI Pharmaceuticals. Association for Research in Vision and Ophthalmology (ARVO) 2015 Annual Meeting. May 6, 2015. Poster. 1 page.

Cardia et al., Novel self-delivering RNAi compounds with enhanced cellular updatake and distribution properties. Keystone RNAi Silencing Conference. Jan. 14-19, 2010. Poster. 1 Page.

Cardia et al., Self-Delivering RNAi Compounds. Drug Delivery Technology. Sep. 2010; 10(7):1-4.

Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.

Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.

Chen et al., Mdm2 deficiency suppresses MYCN-Driven neuroblastoma tumorigenesis in vivo. Neoplasia. Aug. 2009; 11(8):753-62.

Chernikov et al., Current Development of siRNA Bioconjugates: From Research to the Clinic. Front Pharmacol. Apr. 26, 2019;10:444. doi: 10.3389/fphar.2019.00444.

Chiang et al., Antisense oligonucleotides inhibit intercellular adhesion molecule 1 expression by two distinct mechanisms. J Biol Chem. Sep. 25, 1991;266(27):18162-71.

Chiu et al., Visualizing a correlation between siRNA localization, cellular uptake, and RNAi in living cells. Chem Biol. Aug. 2004;11(8):1165-75.

Chiu et al., siRNA function in RNAi: a chemical modification analysis. RNA. Sep. 2003;9(9):1034-48.

Choung et al., Chemical modification of siRNAs to improve serum stability without loss of efficacy. Biochem Biophys Res Commun. Apr. 14, 2006;342(3):919-27.

Chu et al., Potent RNAi by short RNA triggers. RNA. 2008;14:1714-9.

Chung et al., Discovery and characterization of small molecule inhibitors of the BET family bromodomains. J Med Chem. Jun. 9, 2011;54(11):3827-38. doi: 10.1021/jm200108t. Epub May 13, 2011. Supp. Information: S7-S10. S20. Retrieved from: https://pubs.acs.org/doi/suppl/10.1021/jm200108t/suppl_file/jm200108_si_001.pdf.

Corsello et al., Endocrine side effects induced by immune checkpoint inhibitors. J Clin Endocrinol Metab. Apr. 2013;98(4):1361-75. doi: 10.1210/jc.2012-4075. Epub Mar. 7, 2013. Review.

Crombez et al., A non-covalent peptide-based strategy for siRNA delivery. Biochem Soc Trans. Feb. 2007;35(Pt 1):44-6. Review.

Czauderna et al., Structural variations and stabilising modifications of synthetic siRNAs in mammalian cells. Nucleic Acids Res. Jun. 1, 2003;31(11):2705-16.

De Smidt et al., Association of antisense oligonucleotides with lipoproteins prolongs the plasma half-life and modifies the tissue distribution. Nucleic Acids Res. Sep. 11, 1991;19(17):4695-700.

Debart et al., Chemical modifications to improve the cellular uptake of oligonucleotides. Curr Top Med Chem. 2007;7(7):727-37.

Dispersyn et al., Intratumoral use of self-delivering RNAi to reprogram the tumor microenvironment and boost the antitumor response. Journal of Clinical Oncology. May 25, 2020 38:15_suppl, e15206-e15206 . Conference Abstract.

Dykxhoorn et al., The silent treatment: siRNAs as small molecule drugs. Gene Ther. Mar. 2006; 13(6):541-52. Review.

Eichelbaum et al., Influence of pharmacogenetics on drug disposition and response. Clin Exp Pharmacol Physiol. Oct.-Nov. 1996;23(10-11):983-5. Review.

Elbashir et al., Duplexes of 21-nucleotide RNAs mediate RNA interference in cultured mammalian cells. Nature. May 24, 2001;411(6836):494-8.

Elbashir et al., Functional anatomy of siRNAs for mediating efficient RNAi in *Drosophila* melanogaster embryo lysate. Embo J. Dec. 3, 2001;20(23):6877-88.

Fabbri et al., MicroRNA-29 family reverts aberrant methylation in lung cancer by targeting DNA methyltransferases 3A and 3B. Proc Natl Acad Sci U S A. Oct. 2, 2007;104(40):15805-10. Epub Sep. 21, 2007.

Fedorov et al., Off-target effects by siRNA can induce toxic phenotype. RNA. Jul. 2006;12(7):1188-96. Epub May 8, 2006.

Ferentz et al., Disulfide-crosslinked oligonucleotides. Journal of the American Chemical Society. 1991;113 (10): 4000-4002.

Fisher et al., Intracellular disposition and metabolism of fluorescently-labeled unmodified and modified oligonucleotides microinjected into mammalian cells. Nucleic Acids Res. Aug. 11, 1993;21(16):3857-65.

Florence, The oral absorption of micro- and nanoparticulates: neither exceptional nor unusual. Pharm Res. Mar. 1997; 14(3):259-66.

Floyd et al., The bromodomain protein Brd4 insulates chromatin from DNA damage signalling. Nature. Jun. 13, 2013;498(7453):246-50. doi: 10.1038/nature12147. Epub Jun. 2, 2013.

Frank-Kamenetsky et al., Therapeutic RNAi targeting PCSK9 acutely lowers plasma cholesterol in rodents and LDL cholesterol in non-human primates. Proc Natl Acad Sci U S A. Aug. 19, 2008;105(33):11915-20. doi: 10.1073/pnas.0805434105. Epub Aug. 11, 2008.

Freeley et al., Advances in siRNA delivery to T-cells: potential clinical applications for inflammatory disease, cancer and infection. Biochem J. Oct. 15, 2013;455(2):133-47. doi: 10.1042/BJ20130950.

Gallas et al., Chemistry and formulations for siRNA therapeutics. Chem Soc Rev. Oct. 21, 2013;42(20):7983-97. doi: 10.1039/c3cs35520a.

Gao et al., Targeting BRD4 proteins suppresses the growth of NSCLC through downregulation of eIF4E expression. Cancer Biol Ther. May 4, 2018;19(5):407-415. doi: 10.1080/15384047.2018.1423923. Epub Feb. 6, 2018.

Gattinoni et al., T memory stem cells in health and disease. Nat Med. Jan. 6, 2017;23(1):18-27. doi: 10.1038/nm.4241.

Gaudana et al., Ocular drug delivery. AAPS J. Sep. 2010;12(3):348-60. doi: 10.1208/s12248-010-9183-3. Epub May 1, 2010.

Glaser, Oligonucleotide therapies move toward efficacy trials to treat HIV CMV, cancer. Genetic Engineering News. Feb. 1, 2016;16:1-21.

Grosse et al., In vivo gene delivery in the mouse lung with lactosylated polyethylenimine, questioning the relevance of in vitro experiments. J Control Release. Dec. 8, 2008;132(2):105-12. Epub Sep. 4, 2008.

(56) References Cited

OTHER PUBLICATIONS

Haraszti et al., Optimized Cholesterol-siRNA Chemistry Improves Productive Loading onto Extracellular Vesicles. Mol Ther. Aug. 1, 2018;26(8):1973-1982. doi: 10.1016/j.ymthe.2018.05.024. Epub Jun. 21, 2018.

Hassler et al., Comparison of partially and fully chemically-modified siRNA in conjugate-mediated delivery in vivo. Nucleic Acids Res. Mar. 16, 2018;46(5):2185-2196. doi: 10.1093/nar/gky037. Suppl. Data 9 pages.

Heemskerk et al., T-cell receptor gene transfer for the treatment of leukemia and other tumors. Haematologica. Jan. 2010;95(1):15-9. doi: 10.3324/haematol.2009.016022.

Heung et al., Enhancing dendritic cell vaccine potency by combining a BAK/BAX siRNA-mediated antiapoptotic strategy to prolong dendritic cell life with an intracellular strategy to target antigen to lysosomal compartments. Apr. 15, 2007. Medline Database Accession No. NLM17230516.

Hodi et al., New toxicities of immune checkpoint modulators. Ann Oncol. 2013;24(Suppl1):i7-i17.

Hoerter et al., Chemical modification resolves the asymmetry of siRNA strand degradation in human blood serum. RNA. Nov. 2007;13(11):1887-93. doi: 10.1261/rna.602307. Epub Sep. 5, 2007.

Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.

Hudziak et al., Resistance of morpholino phosphorodiamidate oligomers to enzymatic degradation. Antisense Nucleic Acid Drug Dev. 1996 Winter;6(4):267-72.

Hyeon Lee et al., Current preclinical small interfering RNA (siRNA)-based conjugate systems for RNA therapeutics. Adv Drug Deliv Rev. Sep. 1, 2016;104:78-92. doi: 10.1016/j.addr.2015.10.009. Epub Oct. 27, 2015.

Iwakuma et al., MDM2, an introduction. Mol Cancer Res. Dec. 2003;1(14):993-1000.

Jackson et al., Position-specific chemical modification of siRNAs reduces "off-target" transcript silencing. RNA. Jul. 2006; 12(7):1197-1205. Epub May 8, 2006.

Kamens et al., Novel, chemically modified RNAi compounds with improved potency, stability and specificity. Keystone RNAi Silencing: Mechanism, Biology and Application Conference. Jan. 14-19, 2010. Poster. 1 Page.

Kim et al., Blocking the immunosuppressive axis with small interfering RNA targeting interleukin (IL)-10 receptor enhances dendritic cell-based vaccine potency. Clin Exp Immunol. Aug. 2011;165(2):180-9. doi: 10.1111/j.1365-2249.2011.04410.x. Epub May 18, 2011.

Kim et al., Systemic and specific delivery of small interfering RNAs to the liver mediated by apolipoprotein A-I. Mol Ther. Jun. 2007; 15(6):1145-52. Epub Apr. 17, 2007.

Knoechel et al., An epigenetic mechanism of resistance to targeted therapy in T cell acute lymphoblastic leukemia. Nat Genet. Apr. 2014;46(4):364-70. doi: 10.1038/ng.2913. Epub Mar. 2, 2014.

Kubo et al., Modified 27-nt dsRNAs with dramatically enhanced stability in serum and long- term RNAi activity. Oligonucleotides. 2007 Winter; 17(4):445-64.

Layzer et al., In vivo activity of nuclease-resistant siRNAs. RNA. May 2004;10(5):766-71.

Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.

Letsinger et al., Cholesteryl-conjugated oligonucleotides: synthesis, properties, and activity as inhibitors of replication of human immunodeficiency virus in cell culture. Proc Natl Acad Sci USA. Sep. 1989;86(17):6553-6.

Leuschner et al., Cleavage of the siRNA passenger strand during RISC assembly in human cells. EMBO Reports 2006;7(3):314-20.

Li et al., BRD4 Promotes DNA Repair and Mediates the Formation of TMPRSS2-ERG Gene Rearrangements in Prostate Cancer. Cell Rep. Jan. 16, 2018;22(3):796-808. doi: 10.1016/j.celrep.2017.12.078.

Li et al., Surface-modified LPD nanoparticles for tumor targeting. Ann N Y Acad Sci. Oct. 2006;1082:1-8.

Manoharan et al., Chemical modifications to improve uptake and bioavailability of antisense oligonucleotides. Ann N Y Acad Sci. Oct. 28, 1992;660:306-9.

Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.

Martins et al., Sterol side chain length and structure affect the clearance of chylomicron-like lipid emulsions in rats and mice. J Lipid Res. Feb. 1998;39(2):302-12.

Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.

Maxwell et al., The Use of Self-delivering RNAi to Enhance NK Cell Cytotoxicity. Discovery on Target. Sep. 26, 2018. Poster. 1 Page.

Medarova et al., In vivo imaging of siRNA delivery and silencing in tumors. Nat Med. Mar. 2007; 13(3):372-7. Epub Feb. 25, 2007.

Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.

Miska et al., Autoimmunity-mediated antitumor immunity: tumor as an immunoprivileged self. Eur J Immunol. Oct. 2012;42(10):2584-96. doi: 10.1002/eji.201242590. Epub Aug. 10, 2012.

Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.

Ortigão et al., Antisense effect of oligodeoxynucleotides with inverted terminal internucleotidic linkages: a minimal modification protecting against nucleolytic degradation. Antisense Res Dev. 1992 Summer;2(2):129-46.

Overhoff et al., Phosphorothioate-stimulated uptake of short interfering RNA by human cells. EMBO Rep. Dec. 2005;6(12):1176-81.

Pardoll, The blockade of immune checkpoints in cancer immunotherapy. Nat Rev Cancer. Mar. 22, 2012;12(4):252-64. doi: 10.1038/nrc3239. Review.

Parrish et al., Functional anatomy of a dsRNA trigger: differential requirement for the two trigger strands in RNA interference. Mol Cell. Nov. 2000;6(5):1077-87.

Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.

Peng et al., Vaccination with dendritic cells transfected with BAK and BAX siRNA enhances antigen-specific immune responses by prolonging dendritic cell life. Hum Gene Ther. May 2005;16(5):584-93.

Rajeev et al., 2'-modified-2-thiothymidine oligonucleotides. Org Lett. Aug. 21, 2003;5(17):3005-8.

Rose et al., Functional polarity is introduced by Dicer processing of short substrate RNAs. Nucleic Acids Res. Jul. 26, 2005;33(13):4140-56. Print 2005.

Rozema et al., Dynamic PolyConjugates for targeted in vivo delivery of siRNA to hepatocytes. Proc Natl Acad Sci U S A. Aug. 7, 2007; 104(32): 12982-12987.

Rozners et al., Expanding functionality of RNA: synthesis and properties of RNA containing imidazole modified tandem G-U wobble base pairs. Chem Commun (Camb). Dec. 14, 2005;(46):5778-80.

Rump et al., Preparation of conjugates of oligodeoxynucleotides and lipid structures and their interaction with low-density lipoprotein. Bioconjug Chem. May-Jun. 1998;9(3):341-9.

(56) References Cited

OTHER PUBLICATIONS

Sakamaki et al., Bromodomain Protein BRD4 Is a Transcriptional Repressor of Autophagy and Lysosomal Function. Mol Cell. May 18, 2017;66(4):517-532.e9. doi: 10.1016/j.molcel.2017.04.027.
Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Setten et al., The current state and future directions of RNAi-based therapeutics. Nat Rev Drug Discov. Jun. 2019; 18(6):421-446. doi: 10.1038/s41573-019-0017-4. Erratum in: Nat Rev Drug Discov. Mar. 18, 2019;: Erratum in: Nat Rev Drug Discov. Apr. 24, 2019.
Shen, Advances in the development of siRNA-based therapeutics for cancer. IDrugs. Aug. 2008;11(8):572-8. Review.
Shi, Mammalian RNAi for the masses. Trends Genet. Jan. 2003; 19(1):9-12.
Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytogfr.2008.01.002.
Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.
Sibley et al. Novel RNA-based strategies for therapeutic gene silencing. Mol Ther. Mar. 2010;18(3):466-76. doi: 10.1038/mt.2009.306. Epub Jan. 19, 2010.
Smith et al., Pulmonary deposition and clearance of aerosolized alpha-1-proteinase inhibitor administered to dogs and to sheep. J Clin Invest. Oct. 1989;84(4):1145-54.
Snead et al., RNA interference trigger variants: getting the most out of RNA for RNA interference-based therapeutics. Nucleic Acid Ther. Jun. 2012;22(3):139-46. doi: 10.1089/nat.2012.0361. Review.
Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.
Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.
Soutschek et al., Therapeutic silencing of an endogenous gene by systemic administration of modified siRNAs. Nature. Nov. 11, 2004;432(7014):173-8.
Stein et al., A specificity comparison of four antisense types: morpholino, 2'-O-methyl RNA, DNA, and phosphorothioate DNA. Antisense Nucleic Acid Drug Dev. Jun. 1997;7(3):151-7.
Summerton et al., Morpholino and phosphorothioate antisense oligomers compared in cell-free and in-cell systems. Antisense Nucleic Acid Drug Dev. Apr. 1997;7(2):63-70.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.
Tai et al., Chemical modulation of siRNA lipophilicity for efficient delivery. J Control Release. Aug. 10, 2019;307:98-107. doi: 10.1016/j.jconrel.2019.06.022. Epub Jun. 21, 2019.
Tan et al., Inhibition of BRD4 suppresses tumor growth in prostate cancer via the enhancement of FOXO1 expression. Int J Oncol. Dec. 2018;53(6):2503-2517. doi: 10.3892/ijo.2018.4577. Epub Sep. 27, 2018.
Tan et al., Quantum-dot based nanoparticles for targeted silencing of HER2/neu gene via RNA interference. Biomaterials. Mar. 2007;28(8):1565-71. Epub Dec. 11, 2006.
Taylor et al., Curbing activation: proprotein convertases in homeostasis and pathology. Faseb J. Jul. 2003;17(10):1215-27.
Uhlmann et al., Antisense oligonucleotides: a new therapeutic principle. Chem Rev. 1990;90(4):543-84.
Vaught et al., Expanding the chemistry of DNA for in vitro selection. J Am Chem Soc. Mar. 31, 2010;132(12):4141-51. doi: 10.1021/ja908035g.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
Wang et al., Recruitment of Brd4 to the human papillomavirus type 16 DNA replication complex is essential for replication of viral DNA. J Virol. Apr. 2013;87(7):3871-84. doi: 10.1128/JVI.03068-12. Epub Jan. 30, 2013.
Wolfrum et al., Mechanisms and optimization of in vivo delivery of lipophilic siRNAs. Nat Biotechnol. Oct. 2007;25(10):1149-57. Epub Sep. 16, 2007.
Wu et al., Durable protection from Herpes Simplex Virus-2 transmission following intravaginal application of siRNAs targeting both a viral and host gene. Cell Host Microbe. Jan. 22, 2009;5(1):84-94. doi: 10.1016/j.chom.2008.12.003.
Xu et al., Tumor Microenvironment-Responsive Multistaged Nanoplatform for Systemic RNAi and Cancer Therapy. Nano Lett. Jul. 12, 2017;17(7):4427-4435. doi: 10.1021/acs.nanolett.7b01571. Epub Jun. 26, 2017. Supp. Information: 27 pages.
Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.
Zhou et al., Controlled release of PEI/DNA complexes from mannose-bearing chitosan microspheres as a potent delivery system to enhance immune response to Hbv Dna vaccine. J Control Release. Aug. 28, 2007;121(3):200-7. Epub May 25, 2007.
Zimmermann et al., RNAi-mediated gene silencing in non-human primates. Nature. May 4, 2006;441(7089):111-4. Epub Mar. 26, 2006.
[No Author Listed], Developing the Next Generation of immuno-oncology therapeutics. H.C. Wainwright Virtual BioConnect 2022 Conference. Jan. 10, 2022. 31 pages.
Chang et al., Asymmetric shorter-duplex siRNA structures trigger efficient gene silencing with reduced nonspecific effects. Mol Ther. Apr. 2009;17(4):725-32. doi: 10.1038/mt.2008.298. Epub Jan. 20, 2009.
Cuiffo et al., INTASYL self-delivering RNAi therapy specifically dual-targeting BRD4 and PD-1 to elicit complete tumor responses and evidence of synergy in a subcutaneous Hepa1-6 model of murine hepatoma in C57BL/6N mice. J Clin Oncol. May 20, 2021;39(15 Suppl):e14537. doi: 10.1200/JCO.2021.39.15_suppl.e14537. 2021 ASCO Annual Meeting I—Abstract. 1 page.
Facciabene et al., T regulatory cells: key players in tumor immune escape and angiogenesis. Cancer Res. May 1, 2012;72(9):2162-71. doi: 10.1158/0008-5472.CAN-11-3687. Author manuscript, 16 pages.
Kandalaft et al., The emergence of immunomodulation: combinatorial immunochemotherapy opportunities for the next decade. Gynecol Oncol. Feb. 2010;116(2):222-33. doi: 10.1016/j.ygyno.2009.11.001. Epub Dec. 2, 2009. Author manuscript, 27 pages.
Kloss et al., Combinatorial antigen recognition with balanced signaling promotes selective tumor eradication by engineered T cells. Nat Biotechnol. Jan. 2013;31(1):71-5. doi: 10.1038/nbt.2459. Epub Dec. 16, 2012.
Ligtenberg et al., Self-Delivering RNAi Targeting PD-1 Improves Tumor-Specific T Cell Functionality for Adoptive Cell Therapy of Malignant Melanoma. Mol Ther. Jun. 6, 2018;26(6): 1482-1493. doi: 10.1016/j.ymthe.2018.04.015. Epub Apr. 13, 2018.

(56) References Cited

OTHER PUBLICATIONS

Wolfson et al., Enhancement of CAR-T cell activity via PD-1 knockdown by self-deliverable RNAi. Cancer Research. Jul. 1, 2017; 77(13): Supplement 1, 5650.

GENBANK Submission. NCBI Accession No. NM_058243.2. Han et al. Jul. 19, 2020. 7 pages.

Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.

Osborn et al., Hydrophobicity drives the systemic distribution of lipid-conjugated siRNAs via lipid transport pathways. Nucleic Acids Res. Feb. 20, 2019;47(3):1070-1081. doi: 10.1093/nar/gky1232.

* cited by examiner

| | | |
|---|---|---|
| PBS vs NTC | ** | 0.0066 |
| PBS vs BRD4-20 (0.5 mg) | **** | <0.0001 |
| PBS vs BRD4-20 (2.0 mg) | **** | <0.0001 |
| PBS vs JQ1 | **** | <0.0001 |

| | | |
|---|---|---|
| * PBS vs. BRD4-20 (0.5mg) | *** | <0.008 |
| # PBS vs. BRD4-20 (2mg) | *** | <0.01 |

CHEMICALLY MODIFIED OLIGONUCLEOTIDES TARGETING BROMODOMAIN CONTAINING PROTEIN 4 (BRD4) FOR IMMUNOTHERAPY

RELATED APPLICATIONS

This application is a national stage filing under 35 U.S.C. § 371 of International Patent Application Serial No. PCT/US2020/059512, filed Nov. 6, 2020, entitled "CHEMICALLY MODIFIED OLIGONUCLEOTIDES TARGETING BROMODOMAIN CONTAINING PROTEIN 4 (BRD4) FOR IMMUNOTHERAPY" which claims the benefit under 35 U.S.C. § 119 (e) of the filing date of U.S. provisional application Ser. No. 62/932,813, filed Nov. 8, 2019, entitled "CHEMICALLY MODIFIED OLIGONUCLEOTIDES TARGETING BROMODOMAIN CONTAINING PROTEIN 4 (BRD4) FOR IMMUNOTHERAPY," the entire contents of each of which are incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 5, 2022, is named R065970055US01-SEQ-JXV and is 91,385 bytes in size.

FIELD

In some aspects, the disclosure relates to immunomodulatory compositions and methods of making immunomodulatory compositions including the use of oligonucleotides to modulate a gene target, bromodomain containing protein 4 (BRD4), involved in transcriptional and epigenetic regulation to improve the population or subsets of therapeutic immune cells. The disclosure further relates to methods of using immunomodulatory compositions for the treatment of cell proliferative disorders or infectious disease, including, for example, cancer and autoimmune disorders.

BACKGROUND

A physiologic function of the immune system is to recognize and eliminate neoplastic cells. Therefore, an aspect of tumor progression is the development of immune resistance mechanisms. Once developed, these resistance mechanisms not only prevent the natural immune system from affecting the tumor growth, but also limit the efficacy of any immunotherapeutic approaches to cancer. An immune resistance mechanism involves immune-inhibitory pathways, sometimes referred to as immune checkpoints. The immune-inhibitory pathways play a particularly important role in the interaction between tumor cells and CD8+ cytotoxic T-lymphocytes, including Adoptive Cell Transfer (ACT) therapeutic agents.

Various methods of adoptive cell transfer (ACT) involve ex vivo treatment of cells collected from a patient's samples, such as blood or tumor material. Common steps involved in the preparation of cell-based treatments are isolation of cells from the primary source (e.g., peripheral blood), gene editing (e.g., engineering of chimeric antigen receptor (CAR) T-cells or engineered T-cell receptor (TCR) cells), activation, and expansion.

During the ex vivo processing, the cells undergo certain phenotypic changes that may affect their therapeutic properties, such as trafficking to the tumor, proliferative ability and longevity in vivo, and their efficacy in the immunosuppressive environment, among others. For example, the state of T-cell differentiation and maturation typically progresses through the following sequence of subtypes: naïve ($T_N$)-stem cell memory ($T_{SCM}$)-central memory ($T_{CM}$)-effector memory ($T_{EM}$)-terminally differentiated effector T cells ($T_{EFF}$). It has been observed that phenotypic and functional attributes of early memory T-cells ($T_{SCM}$/$T_{CM}$) among CD8+ T cells demonstrate superior in vivo expansion, persistence, and antitumor efficacy than more differentiated effector cells (e.g., $T_{EM}$, $T_{EFF}$, etc.).

SUMMARY

In some aspects, the disclosure relates to compositions and methods for controlling the differentiation process of T-cells during production of immunomodulatory compositions to enhance levels of desired subtypes of therapeutic T cells (e.g., $T_{SCM}$ and $T_{CM}$). The disclosure is based, in part, on immunomodulatory (e.g., immunogenic) compositions comprising a host cell comprising oligonucleotide molecules that target genes associated with signal transduction/transcription factors, epigenetic, metabolic and co-inhibitory/negative regulatory targets, as well as methods of producing such compositions. In some aspects, the disclosure provides chemically-modified oligonucleotide molecules for use in methods of producing immunomodulatory compositions. In some embodiments, methods and compositions described by the disclosure are useful for the manufacture of immunomodulatory compositions and for treating a subject having a proliferative or infectious disease.

Accordingly, in some aspects, the disclosure provides a chemically-modified double stranded nucleic acid molecule that targets (e.g., is directed against a gene encoding) a member of the bromodomains and extraterminal (BET) family, Bromodomain Containing Protein 4 (BRD4).

In some embodiments, a chemically-modified double stranded nucleic acid molecule is directed against a sequence comprising at least 12 contiguous nucleotides of a sequence selected from the sequences within Table 1. In some embodiments, a chemically-modified double stranded nucleic acid molecule is a self-delivering RNA (e.g., INTASYL™; also referred to herein as sd-rxRNA)). In some embodiments, a chemically-modified double stranded nucleic acid molecule (e.g., INTASYL™) comprises or consists of, or is targeted to or directed against, a sequence set forth in Tables 1 or 2, or a fragment thereof.

In some embodiments, a chemically-modified double stranded nucleic acid molecule comprises at least one 2'-O-methyl modification and/or at least one 2'-O-Fluoro modification, and at least one phosphorothioate modification.

In some aspects, the disclosure provides an INTASYL™ compound that is directed against a gene encoding BRD4. In some embodiments, an INTASYL™ compound (sd-rxRNA) comprises at least 12 contiguous nucleotides of a sequence selected from the sequences within Table 2.

In some embodiments, an INTASYL™ compound is hydrophobically modified. In some embodiments, an INTASYL™ compound is linked to one or more hydrophobic conjugates. In some embodiments, the hydrophobic conjugate is cholesterol.

In some embodiments, a chemically-modified double stranded nucleic acid molecule or an INTASYL™ compound as described herein comprises or consists of the sequence set forth in BRD4-20 sense or antisense strand or BRD4-21 sense or antisense strand or BRD4-22 sense or antisense strand.

In some embodiments, a chemically-modified double stranded nucleic acid molecule or an INTASYL™ compound as described herein comprises or consists of a sense strand having the sequence set forth in BRD4-20 sense strand and/or an antisense strand having the sequence set forth in BRD4-20 antisense strand. In some embodiments, a chemically-modified double stranded nucleic acid molecule or INTASYL™ compound as described herein comprises or consists of a sense strand having the sequence set forth in BRD4-21 sense strand and/or an antisense strand having the sequence set forth in BRD4-21 antisense strand. In some embodiments, a chemically-modified double stranded nucleic acid molecule or INTASYL™ compound as described herein comprises or consists of a sense strand having the sequence set forth in BRD4-22 sense strand and/or an antisense strand having the sequence set forth in BRD4-22 antisense strand.

In some aspects, the disclosure provides a composition comprising a chemically-modified double stranded nucleic acid molecule or an INTASYL™ compound as described herein and a pharmaceutically acceptable excipient.

In some embodiments, a composition as described herein comprises a chemically-modified double stranded nucleic acid molecule or an INTASYL™ compound directed against BRD4. In some embodiments, a chemically-modified double stranded nucleic acid molecule or an INTASYL™ compound directed against BRD4 comprises at least 12 contiguous nucleotides of a sequence selected from Table 2.

In some aspects, the disclosure provides an immunomodulatory composition comprising a host cell (e.g., an immune cell, such as a T-cell or NK cell) which has been treated ex vivo with a chemically-modified double stranded nucleic acid molecule to control and/or reduce the level of differentiation of the host cell (e.g., T-cell) to enable the production of a specific immune cellular population (e.g., a population enriched for a particular T-cell subtype) for administration in a human. In some embodiments, an immunomodulatory composition comprises a plurality of host cells that are enriched for a particular cell type (e.g. T-cell subtype). For example, in some embodiments, an immunomodulatory composition comprises at least 50%, at least 60%, at least 70%, at least 80%, at least 90%, at least 95%, at least 99% or 100% (e.g., any percentage between 50% and 100%, inclusive) T-cells of a particular T-cell subtype, such as $T_{SCM}$ or $T_{CM}$ cells.

In some embodiments, an immunomodulatory composition comprises a host cell comprising a chemically-modified double stranded nucleic acid molecule as described herein (e.g., a chemically-modified double stranded nucleic acid molecule or an INTASYL™ compound that is directed against a gene encoding BRD4). In some embodiments, the chemically-modified double stranded nucleic acid molecule or INTASYL™ compound is directed against a sequence comprising at least 12 contiguous nucleotides of a sequence selected from the sequences within Table 1. In some embodiments, a chemically-modified double stranded nucleic acid molecule (e.g., INTASYL™) comprises or consists of, or is targeted to or directed against, a sequence set forth in Tables 1 and 2, or a fragment thereof.

In some embodiments, a host cell comprises a chemically-modified double stranded nucleic acid molecule that is directed against BRD4. In some embodiments, the chemically-modified double stranded nucleic acid molecule directed against BRD4 comprises at least 12 contiguous nucleotides of a sequence selected from Table 2.

In some embodiments, a host cell is selected from the group of: T-cell, NK-cell, antigen-presenting cell (APC), dendritic cell (DC), stem cell (SC), induced pluripotent stem cell (iPSC), stem cell memory T-cell, and Cytokine-induced Killer cell (CIK). In some embodiments, the host cell is a T-cell. In some embodiments, the T-cell is a CD8+ T-cell. In some embodiments, the T-cell is differentiated into a particular T-cell subtype, such as a $T_{SCM}$ or $T_{CM}$ T-cell after introduction of the chemically-modified double stranded nucleic acid or INTASYL™ compound.

In some embodiments, a T-cell comprises one or more transgenes expressing a high affinity T-cell receptor (TCR) and/or a chimeric antigen receptor (CAR).

In some embodiments, a host cell is derived from a healthy donor.

In some aspects, the disclosure provides a method for producing an immunomodulatory composition, the method comprising introducing into a cell one or more chemically-modified double stranded nucleic acid molecules or INTASYL™ compounds as described herein. In some embodiments, the chemically-modified double stranded nucleic acid molecules or sd-rxRNA are introduced into the cell ex vivo.

In some embodiments of methods described herein, a cell is a T-cell, NK-cell, antigen-presenting cell (APC), dendritic cell (DC), stem cell (SC), induced pluripotent stem cell (iPSC), stem cell memory T-cell, and Cytokine-induced Killer cell (CIK).

In some embodiments, the T-cell is a $CD8^+$ T-cell. In some embodiments, the T-cell is differentiated into a particular T-cell subtype, such as a $T_{SCM}$ or $T_{CM}$ T-cell after introduction of the chemically-modified double stranded nucleic acid or sd-rxRNA. In some embodiments, the T-cell comprises one or more transgenes expressing a high affinity T-cell receptor (TCR) and/or a chimeric antigen receptor (CAR). In some embodiments, the cell is derived from a healthy donor.

In some aspects, the disclosure provides a method for treating a subject for suffering from a proliferative disease or an infectious disease, the method comprising administering to the subject an immunomodulatory composition as described herein. In some embodiments, a proliferative disease is cancer. In some embodiments, an infectious disease is a pathogen infection, such as a viral, bacterial, or parasitic infection.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6A shows the raw data, and FIG. 6B shows the quantification of the data. The results were obtained following no treatment (UNT), treatment with a non-targeting control (NTC; negative control), treatment with BRD4-20, or treatment with JQ1 (a positive control).

FIG. 9A represents the mean tumor volume over time, and FIG. 9B shows the tumor volume AUC following the treatment indicated.

DETAILED DESCRIPTION

Figure 1:
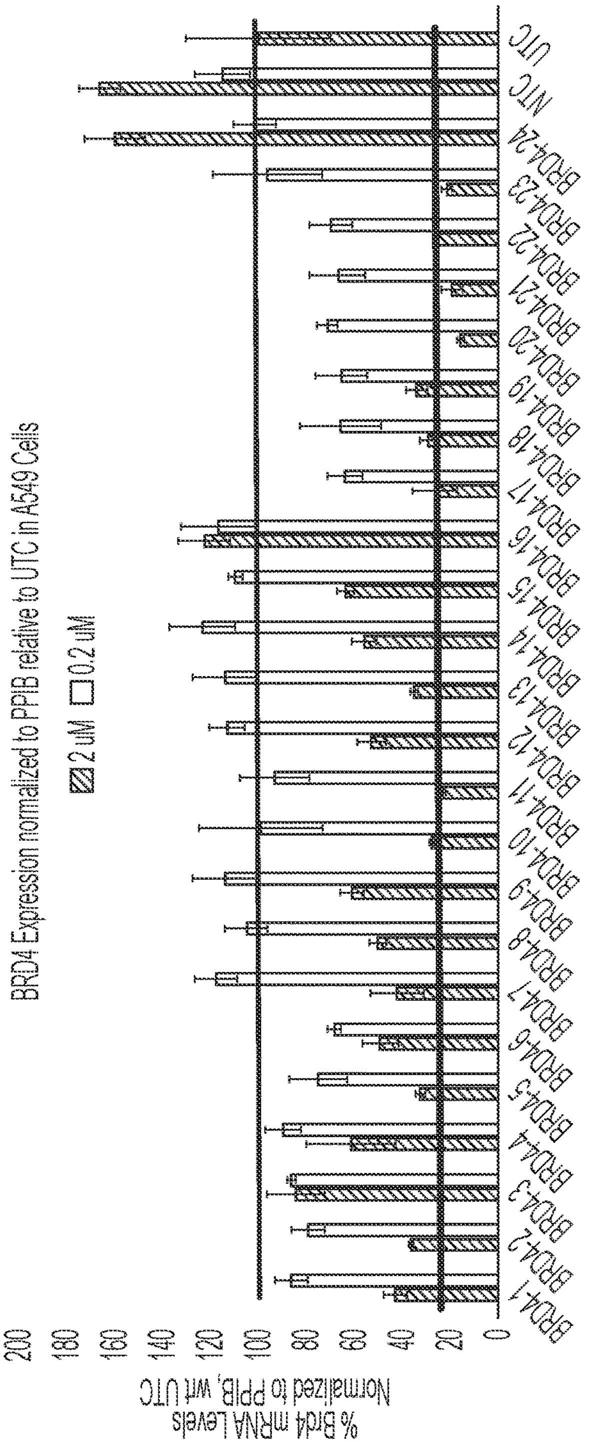
FIG. 1 shows a two point dose response of mRNA silencing of chemically modified INTASYL™ molecules targeting BRD4 in A549 cells.

In some aspects, the disclosure relates to compositions and methods for immunotherapy. The disclosure is based, in part, on chemically modified double-stranded nucleic acid molecules (e.g., INTASYL™) targeting genes associated with controlling the differentiation process of T-cells, such as BRD4.

INTASYL™ technology is particularly suitable for controlling the differentiation process of cells, including T-cells, and the production of therapeutic cells rich in the desired subtypes ($T_{SCM}/T_{CM}$). Several advantages of INTASYL™ include: (i) INTASYL™ can be developed in a short period of time and can silence virtually any target including "non-druggable" targets, e.g., those that are difficult to inhibit by small molecules, e.g., transcription factors; (ii) compared to alternative ex vivo siRNA transfection techniques (e.g., lipid mediated transfection or electroporation), INTASYL™ can transfect a variety of cell types, including T cells with high transfection efficiency retaining a high cell viability; (iii) when added to cell culture media at an early expansion stage, INTASYL™ compounds provide transient silencing of targets of interest during 8-10 division cycles, allowing the silencing effect to disappear in the final population of cells by the time of their re-infusion into a patient; (iv) INTASYL™ can be used in combination to simultaneously silence multiple targets, thus providing considerable flexibility for the use in different types of cell treatment protocols.

Described herein are INTASYL™ compounds directed to specific targets involved in the differentiation of T cells, and the beneficial effect of such INTASYL™ on the phenotype of T cells during and or following ex vivo expansion. Also presented is a screening method that can be used to identify INTASYL™ compounds suitable for a specific cell production protocol.

As used herein, "nucleic acid molecule" includes but is not limited to: INTASYL™, sd-rxRNA, rxRNAori, oligonucleotides, ASO, siRNA, shRNA, miRNA, ncRNA, cp-lasiRNA, aiRNA, single-stranded nucleic acid molecules, double-stranded nucleic acid molecules, RNA and DNA. In some embodiments, the nucleic acid molecule is a chemically-modified nucleic acid molecule, such as a chemically-modified oligonucleotide. In some embodiments, the nucleic acid molecule is double stranded. In some embodiments, chemically-modified double stranded nucleic acid molecules as described herein are INTASYL™ (also known as sd-rxRNA) molecules.

INTASYL™ (Sd-rxRNA) Molecules

Aspects of the invention relate to INTASYL™ molecules that target genes associated with controlling the differentiation process of T-cells, such as BRD4. In some embodiments, the disclosure provides an INTASYL™ targeting the gene BRD4. In some embodiments, an INTASYL™ molecule described herein comprises or consists of, or is targeted to or directed against, a sequence set forth in Table 2, or a fragment thereof.

As used herein, an "sd-rxRNA" or an "sd-rxRNA molecule" or an "INTASYL™" or an "INTASYL™ molecule" or an INTASYL compound" refers to a self-delivering RNA molecule such as those described in, and incorporated by reference from, U.S. Pat. No. 8,796,443, granted on Aug. 5, 2014, entitled "REDUCED SIZE SELF-DELIVERING RNAI COMPOUNDS", U.S. Pat. No. 9,175,289, granted on Nov. 3, 2015, entitled "REDUCED SIZE SELF-DELIVERING RNAI COMPOUNDS", U.S. Pat. No. 10,774,330, granted on Sep. 15, 2020, entitled "REDUCED SIZE SELF-DELIVERING RNAI COMPOUNDS," and PCT Publication No. WO2010/033247 (Application No. PCT/US2009/005247), filed on Sep. 22, 2009, and entitled "REDUCED SIZE SELF-DELIVERING RNAI COMPOUNDS." Briefly, an INTASYL™, (also referred to as an sd-rxRNA$^{nano}$) is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications. In preferred embodiments, the double stranded nucleic acid molecule has one end that is blunt or includes a one or two nucleotide overhang. INTASYL™ molecules can be optimized through chemical modification, and in some instances through attachment of hydrophobic conjugates. Each of the above-referenced patents and publications are incorporated by reference herein in their entireties.

In some embodiments, an INTASYL™ comprises an isolated double stranded nucleic acid molecule comprising a guide strand and a passenger strand, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the double stranded nucleic acid are modified.

The nucleic acid molecules of the invention are referred to herein as isolated double stranded or duplex nucleic acids, oligonucleotides or polynucleotides, nano molecules, nano RNA, sd-rxRNA$^{nano}$, sd-rxRNA, INTASYL™ or RNA molecules of the invention.

INTASYL™ molecules are much more effectively taken up by cells compared to conventional siRNAs. These molecules are highly efficient in silencing of target gene expression and offer significant advantages over previously described RNAi molecules including high activity in the presence of serum, efficient self-delivery, compatibility with a wide variety of linkers, and reduced presence or complete absence of chemical modifications that are associated with toxicity.

In contrast to single-stranded polynucleotides, duplex polynucleotides have traditionally been difficult to deliver to a cell as they have rigid structures and a large number of negative charges which makes membrane transfer difficult. INTASYL™ molecules however, although partially double-stranded, are recognized in vivo as single-stranded and, as such, are capable of efficiently being delivered across cell membranes. As a result, the polynucleotides of the invention are capable in many instances of self-delivery. Thus, the polynucleotides of the invention may be formulated in a manner similar to conventional RNAi agents or they may be delivered to the cell or subject alone (or with non-delivery type carriers) and allowed to self-deliver. In one embodiment of the present invention, self-delivering asymmetric double-stranded RNA molecules are provided in which one portion of the molecule resembles a conventional RNA duplex and a second portion of the molecule is single stranded.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. In some embodiments, this class of RNAi like compounds have superior efficacy in vitro and in vivo. It is believed that the reduction in the size of the rigid duplex region in combination with phosphorothioate modifications applied to a single stranded region contribute to the observed superior efficacy.

In some embodiments, the RNAi compounds of the invention comprise an asymmetric compound comprising a duplex region (required for efficient RISC entry) of 8-15 bases long and a single stranded region of 4-12 nucleotides long. In some embodiments, the duplex region is 13 or 14 nucleotides long, and in some embodiments, the since stranded region is 6-7 nucleotides long. The single stranded region of the RNAi compounds (e.g., INTASYL™ molecules) also comprises 2-12 phosphorothioate internucleotide linkages (referred to as phosphorothioate modifications). In some embodiments, the single stranded region comprises 6-8 phosphorothioate internucleotide linkages. Additionally, the RNAi compounds of the invention also include a unique chemical modification pattern, which provides stability and is compatible with RISC entry. In some embodiments, the combination of these elements has resulted in unexpected properties which are highly useful for delivery of RNAi reagents in vitro and in vivo.

The chemical modification pattern, which provides stability and is compatible with RISC entry includes modifications to the sense, or passenger, strand as well as the antisense, or guide, strand. For instance, the passenger strand can be modified with any chemical entities which confirm stability and do not interfere with activity. Such modifications include 2' ribo modifications (O-methyl, 2'F, 2 deoxy and others) and backbone modifications, such as phosphorothioate modifications. In some embodiments, the chemical modification pattern in the passenger strand includes O-methyl modification of C and U nucleotides within the passenger strand or alternatively, the passenger strand may be completely O-methyl modified.

The guide strand, in some embodiments, may also be modified by any chemical modification which confirms stability without interfering with RISC entry. In some embodiments, the chemical modification pattern in the guide strand includes the majority of C and U nucleotides being 2'F modified and the 5' end being phosphorylated. In some embodiments, a chemical modification pattern in the guide strand includes 2'O-methyl modification of position 1 and C/U in positions 11-18 and 5' end chemical phosphorylation. In some embodiments, a chemical modification pattern in the guide strand includes 2'O-methyl modification of position 1 and C/U in positions 11-18 and 5' end chemical phosphorylation and 2'F modification of C/U in positions 2-10. In some embodiments, the passenger strand and/or the guide strand contains at least one 5-methyl C or U modification.

In some embodiments, at least 30% of the nucleotides in the sd-rxRNA (e.g., INTASYL™ compound) are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the INTASYL™ compound are modified. In some embodiments, 100% of the nucleotides in the INTASYL™ compound are modified.

The above-described chemical modification patterns of the oligonucleotides of the invention are well tolerated and improve efficacy of asymmetric RNAi compounds. In some embodiments, elimination of any of the described components (guide strand stabilization, phosphorothioate stretch, sense strand stabilization and hydrophobic conjugate) or increase in size, in some instances, results in sub-optimal efficacy and, in some instances, complete loss of efficacy. The combination of elements results in development of a compound, which is fully active following passive delivery to cells such as HeLa cells or T-cells.

The INTASYL™ can be further improved in some instances by improving the hydrophobicity of compounds using novel types of chemistries. For example, one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. In some embodiments, INTASYL™ compounds where multiple deoxy uridines are present without interfering with overall compound efficacy are used. In addition, major improvement in tissue distribution and cellular uptake might be obtained by modifying the structure of the hydrophobic conjugate. In some embodiments, the structure of sterol is modified to alter (increase/decrease) C17 attached chain. This type of modification results in significant increase in cellular uptake and improvement of tissue uptake prosperities in vivo.

In some embodiments, a chemically-modified double stranded nucleic acid molecule is a hydrophobically modified siRNA-antisense hybrid molecule, comprising a double-stranded region of about 13-22 base pairs, with or without a 3'-overhang on each of the sense and antisense strands, and a 3' single-stranded tail on the antisense strand of about 2-9 nucleotides. In some embodiments, the chemically-modified double stranded nucleic acid molecule contains at least one 2'-O-Methyl modification, at least one 2'-Fluoro modification, and at least one phosphorothioate modification, as well as at least one hydrophobic modification selected from sterol, cholesterol, vitamin D, napthyl, isobutyl, benzyl, indol, tryptophane, phenyl, and the like hydrophobic modifiers. In some embodiments, a chemically-modified double stranded nucleic acid molecule comprises a plurality of such modifications.

In some aspects, the disclosure relates to chemically-modified double stranded nucleic acid molecules that target genes encoding targets related to differentiation of cells (e.g., differentiation of T-cells), such as signal transduction/transcription factor targets, epigenetic targets, metabolic and co-inhibitory/negative regulatory targets. Examples of epigenetic proteins include but are not limited to BRD4. In some embodiments, a chemically-modified double stranded nucleic acid targets a gene encoding BRD4.

As used herein, "BRD4" (also known as CAP, MCAP, HUNK1, HUNKI) refers to Bromodomain Containing Protein 4 or Bromodomain Containing 4, a member of the bromodomains and extraterminal (BET) family, which is a transcriptional and epigenetic regulator that plays a role during cancer development. BRD4 contains two bromodomains which recognize acetylated lysine residues on DNA histone tails. As a chromatin regulatory protein, BRD4 binds the acetylated histones, and is involved in the transmission of epigenetic memory across cell divisions and transcription regulation. Specifically, once the protein is bound, it remains with the acetylated chromatin during the entire cell cycle, providing epigenetic memory for postmitotic G1 gene transcription by preserving high-order chromatin structure. (Wang et al. (2012) *J. Biol. Chem.* 287:10738-10752). BRD4 promotes gene transcription during the initiation and elongation steps, as it recruits P-TEFb, a positive transcription elongation factor (Yang et al. (2005) *Mol Cell.* 19(4): 535-45). BRD4 has been implicated in cancer because of its role in modulating transcription elongation of genes involved in cell cycle and apoptosis, such as c-Myc and BCL2. (Jung et al. (2015) *Epigenomics,* 7(3):487-501). In some embodiments, BRD4 is encoded by a nucleic acid sequence represented by NCBI Reference Sequence Number NM_058243.2.

Non-limiting examples of BRD4 sequences that may be targeted by chemically-modified double stranded nucleic acid molecules of the disclosure are listed in Table 2.

In some embodiments a chemically-modified double stranded nucleic acid molecule comprises at least 12 nucleotides of a sequence within Table 2. In some embodiments, a chemically-modified double stranded nucleic acid molecule comprises at least one sequence within Table 2 (e.g., comprises a sense strand or an antisense strand comprising a sequence as set forth in any one of Table 2). In some embodiments, a chemically-modified double stranded nucleic acid molecule (e.g., INTASYL™) comprises or consists of, or is targeted to or directed against, a sequence set forth in Table 2, or a fragment thereof.

In some embodiments, a chemically-modified double stranded nucleic acid molecule (e.g., an INTASYL™) comprises a sense strand having the sequence set forth in BRD4-20 sense strand and/or an antisense strand having the sequence set forth in BRD4-20 antisense strand. In some embodiments, a chemically-modified double stranded nucleic acid molecule (e.g., an INTASYL™) comprises a sense strand having the sequence set forth in BRD4-21 sense strand and/or an antisense strand having the sequence set forth in BRD4-21 antisense strand. In some embodiments, chemically-modified double stranded nucleic acid molecule (e.g., an INTASYL™) comprises a sense strand having the sequence set forth in BRD4-22 sense strand and/or an antisense strand having the sequence set forth in BRD4-22 antisense strand.

In some embodiments, a dsRNA formulated according to the invention is an rxRNAori. rxRNAori refers to a class of RNA molecules described in and incorporated by reference from PCT Publication No. WO2009/102427 (Application No. PCT/US2009/000852), filed on Feb. 11, 2009, and entitled, "MODIFIED RNAI POLYNUCLEOTIDES AND USES THEREOF," and US Patent Publication No. 2011/0039914, filed on Nov. 1, 2010, and entitled "MODIFIED RNAI POLYNUCLEOTIDES AND USES THEREOF."

In some embodiments, an rxRNAori molecule comprises a double-stranded RNA (dsRNA) construct of 12-35 nucleotides in length, for inhibiting expression of a target gene, comprising: a sense strand having a 5'-end and a 3'-end, wherein the sense strand is highly modified with 2'-modified ribose sugars, and wherein 3-6 nucleotides in the central portion of the sense strand are not modified with 2'-modified ribose sugars and, an antisense strand having a 5'-end and a 3'-end, which hybridizes to the sense strand and to mRNA of the target gene, wherein the dsRNA inhibits expression of the target gene in a sequence-dependent manner.

rxRNAori can contain any of the modifications described herein. In some embodiments, at least 30% of the nucleotides in the rxRNAori are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the rxRNAori are modified. In some embodiments, 100% of the nucleotides in the sd-rxRNA are modified. In some embodiments, only the passenger strand of the rxRNAori contains modifications.

Thus, aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. In some embodiments, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments of double stranded nucleic acid molecules described herein, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments of double stranded nucleic acid molecules described herein, the length of the passenger strand ranges from 8-15 nucleotides long. In certain embodiments, the passenger strand is 8, 9, 10, 11, 12, 13, 14 or 15 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-15 nucleotides long. In certain embodiments, the region of the molecule that is double stranded is 8, 9, 10, 11, 12, 13, 14 or 15 nucleotides long. In certain embodiments the double stranded region is 13 or 14 nucleotides long. In some embodiments, the region of the molecule that is double stranded is 13-22 nucleotides long. In certain embodiments, the region of the molecule that is double stranded is 16, 17, 18, 19, 20, 21 or 22 nucleotides long.

There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is at least 6 or at least 7 nucleotides long. In some embodiments, the single stranded region is 2-9 nucleotides long, including 2 or 3 nucleotides long.

RNAi constructs associated with the invention can have a thermodynamic stability (ΔG) of less than −13 kkal/mol. In some embodiments, the thermodynamic stability (ΔG) is less than −20 kkal/mol. In some embodiments there is a loss of efficacy when (ΔG) goes below −21 kkal/mol. In some embodiments a (ΔG) value higher than −13 kkal/mol is compatible with aspects of the invention. Without wishing to be bound by any theory, in some embodiments a molecule with a relatively higher (ΔG) value may become active at a relatively higher concentration, while a molecule with a relatively lower (ΔG) value may become active at a relatively lower concentration. In some embodiments, the (ΔG) value may be higher than −9 kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al 2004).

Without wishing to be bound by any theory, results described herein suggest that a stretch of 8-10 bp of dsRNA or dsDNA will be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If acceptable thermodynamics are present and there is a double stranded portion that is preferably at least 8 nucleotides, then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 5' Phosphonate, 5' Vinyl Phosphonate, 2'-O-methyl, 2'-O-ethyl, 2'-fluoro, ribothymidine, C-5 propynyl-dC (pdC) and C-5 propynyl-dU (pdU); C-5 propynyl-C (pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxyCytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. Specifically, reduction in 2'F content of a molecule is predicted to reduce toxicity of the molecule. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-20 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated and/or contains a vinyl phosphonate. C and U nucleotides within the guide strand can be 2'F modified. For example, C and U nucleotides in positions 2-10 of a 20 nucleotide guide strand (or corresponding positions in a guide strand of a different length) can be 2'F modified. C and U nucleotides within the guide strand can also be 2'OMe modified. For example, C and U nucleotides in positions 11-18 of a 19 nucleotide guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, a passenger strand is approximately 11-14 nucleotides in length. The passenger strand may contain modifications that confer increased stability. One or more nucleotides in the passenger strand can be 2'OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2'OMe modified. One or more of the nucleotides on the passenger strand can also be phosphate-modified such as phosphorothioate modified. The passenger strand can also contain 2' ribo, 2'F and 2 deoxy modifications or any combination of the above. Chemical modification patterns on both the guide and passenger strand can be well tolerated and a combination of chemical modifications can lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications.

Molecules associated with the invention are also designed for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12 C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. In some embodiments, molecules that have a double stranded region of 8-15 nucleotides can be selected for use in RNAi. In some embodiments, molecules are selected based on their thermodynamic stability (ΔG). In some embodiments, molecules will be selected that have a (ΔG) of less than −13 kkal/mol. For example, the (ΔG) value may be −13, −14, −15, −16, −17, −18, −19, −21, −22 or less than −22 kkal/mol. In other embodiments, the (ΔG) value may be higher than −13 kkal/mol. For example, the (ΔG) value may be −12, −11, −10, −9, −8, −7 or more than −7 kkal/mol. It should be appreciated that ΔG can be calculated using any method known in the art. In some embodiments ΔG is calculated using Mfold, available through the Mfold internet site (mfold.bioinfo.rpi.edu/cgi-bin/rna-form1.cgi). Methods for calculating ΔG are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the sd-rxRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

Certain combinations of modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the chemically modified double stranded nucleic acid molecule structures of the present invention mediate sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments, a version of chemically modified double stranded nucleic acid compounds, which are effective in cellular uptake and inhibition of miRNA activity, are described. Essentially, the compounds are similar to RISC entering versions, but large strand chemical modification patterns are made to block cleavage and act as an effective inhibitor of the RISC action. For example, the compound might be completely or mostly O-methyl modified with the phosphorothioate content described previously. For these types of compounds, the 5' phosphorylation is not necessary in some embodiments. The presence of a double stranded region is preferred as it promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. Single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo. As such, the RNAi constructs of the invention are useful for treating a patient with a disease characterized by the over-expression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the nucleic acids of the invention, and cells comprising such vectors or the nucleic acids. The cell may be a mammalian cell in vivo or in culture, such as a human cell.

The invention further relates to compositions comprising the subject RNAi constructs, and a pharmaceutically acceptable carrier or diluent.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2'F modified nucleotides, 2'-O-methyl modified and 2'deoxy nucleotides. In another particular embodiment, the chemically modified nucleotides result from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl ($C_8H_6N$) $CH_2CH(NH_2)CO$), isobutyl, butyl, aminobenzyl; phenyl; naphthyl, etc.), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

In some embodiments, the base moiety of a nucleoside may be modified. For example, a pyrimidine base may be modified at the 2, 3, 4, 5, and/or 6 position of the pyrimidine ring. In some embodiments, the exocyclic amine of cytosine may be modified. A purine base may also be modified. For example, a purine base may be modified at the 1, 2, 3, 6, 7, or 8 position. In some embodiments, the exocyclic amine of adenine may be modified. In some cases, a nitrogen atom in a ring of a base moiety may be substituted with another atom, such as carbon. A modification to a base moiety may be any suitable modification. Examples of modifications are known to those of ordinary skill in the art. In some embodiments, the base modifications include alkylated purines or pyrimidines, acylated purines or pyrimidines, or other heterocycles.

In some embodiments, a pyrimidine may be modified at the 5 position. For example, the 5 position of a pyrimidine may be modified with an alkyl group, an alkynyl group, an alkenyl group, an acyl group, or substituted derivatives thereof. In other examples, the 5 position of a pyrimidine may be modified with a hydroxyl group or an alkoxyl group or substituted derivative thereof. Also, the $N^4$ position of a pyrimidine may be alkylated. In still further examples, the pyrimidine 5-6 bond may be saturated, a nitrogen atom within the pyrimidine ring may be substituted with a carbon atom, and/or the $O^2$ and $O^4$ atoms may be substituted with sulfur atoms. It should be understood that other modifications are possible as well.

In other examples, the $N^7$ position and/or $N^2$ and/or $N^3$ position of a purine may be modified with an alkyl group or substituted derivative thereof. In further examples, a third ring may be fused to the purine bicyclic ring system and/or a nitrogen atom within the purine ring system may be substituted with a carbon atom. It should be understood that other modifications are possible as well.

Non-limiting examples of pyrimidines modified at the 5 position are disclosed in U.S. Patent 5591843, U.S. Pat. Nos. 7,205,297, 6,432,963, and 6,020,483; non-limiting examples of pyrimidines modified at the $N^4$ position are disclosed in U.S. Pat. No. 5,580,731; non-limiting examples of purines modified at the 8 position are disclosed in U.S. Pat. Nos. 6,355,787 and 5,580,972; non-limiting examples of purines modified at the $N^6$ position are disclosed in U.S. Pat. Nos. 4,853,386, 5,789,416, and 7,041,824; and non-limiting examples of purines modified at the 2 position are disclosed in U.S. Pat. Nos. 4,201,860 and 5,587,469, all of which are incorporated herein by reference.

Non-limiting examples of modified bases include $N^4$,$N^4$-ethanocytosine, 7-deazaxanthosine, 7-deazaguanosine, 8-oxo-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, 5-methoxyuracil, 2-methylthio-$N^6$-isopentenyladenine, pseudouracil, 5-methyl-2-thiouracil, 2-thiouracil, 4-thiouracil, 5-methyluracil, 2-thiocytosine, and 2,6-diaminopurine. In some embodiments, the base moiety may be a heterocyclic base other than a purine or pyrimidine. The heterocyclic base may be optionally modified and/or substituted.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($—OCH_2CH{=}CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2—CH_2—CH_3$), glycol ($—O—CH_2—CH_2—O—$) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, $-CH_2$-cyclopropyl, vinyl, allyl, n-butyl, sec-butyl, isobutyl, tert-butyl, cyclobutyl, $-CH_2$-cyclobutyl, n-pentyl, sec-pentyl, isopentyl, tert-pentyl, cyclopentyl, $-CH_2$-cyclopentyl, n-hexyl, sec-hexyl, cyclohexyl, $-CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; $-NO_2$; —CN; $-CF_3$; $-CH_2CF_3$; $-CHCl_2$; $-CH_2OH$; $-CH_2CH_2OH$; $-CH_2NH_2$; $-CH_2SO_2CH_3$; $-C(O)R_x$; $-CO_2(R_x)$; $-CON(R_x)_2$; $-OC(O)R_x$; $-OCO_2R_x$;

—$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$—$CH_2OH$; —$CH_2CH_2OH$; —$CH_2NH_2$: —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The terms "halo" and "halogen" as used herein refer to an atom selected from fluorine, chlorine, bromine, and iodine.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfydryl, alkylthio, arylthio, thiocarboxylate, sulfates, alkylsulfamoyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —$O^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The olynucleotide may comprise a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

The term "base" includes the known purine and pyrimidine heterocyclic bases, deazapurines, and analogs (including heterocyclic substituted analogs, e.g., aminoethyloxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

The nucleic acid molecules may be associated with a hydrophobic moiety for targeting and/or delivery of the molecule to a cell. In certain embodiments, the hydrophobic moiety is associated with the nucleic acid molecule through a linker. In certain embodiments, the association is through non-covalent interactions. In other embodiments, the association is through a covalent bond. Any linker known in the art may be used to associate the nucleic acid with the hydrophobic moiety. Linkers known in the art are described in published international PCT applications, WO 92/03464, WO 95/23162, WO 2008/021157, WO 2009/021157, WO 2009/134487, WO 2009/126933, U.S. Patent Application Publication 2005/0107325, U.S. Pat. Nos. 5,414,077, 5,419,966, 5,512,667, 5,646,126, and 5,652,359, which are incorporated herein by reference. The linker may be as simple as a covalent bond to a multi-atom linker. The linker may be cyclic or acyclic. The linker may be optionally substituted. In certain embodiments, the linker is capable of being cleaved from the nucleic acid. In certain embodiments, the linker is capable of being hydrolyzed under physiological conditions. In certain embodiments, the linker is capable of being cleaved by an enzyme (e.g., an esterase or phosphodiesterase). In certain embodiments, the linker comprises a spacer element to separate the nucleic acid from the hydrophobic moiety. The spacer element may include one to thirty carbon or heteroatoms. In certain embodiments, the linker and/or spacer element comprises protonatable functional groups. Such protonatable functional groups may promote the endosomal escape of the nucleic acid molecule. The protonatable functional groups may also aid in the delivery of the nucleic acid to a cell, for example, neutralizing the overall charge of the molecule. In other embodiments, the linker and/or spacer element is biologically inert (that is, it does not impart biological activity or function to the resulting nucleic acid molecule).

In certain embodiments, the nucleic acid molecule with a linker and hydrophobic moiety is of the formulae described herein. In certain embodiments, the nucleic acid molecule is of the formula:

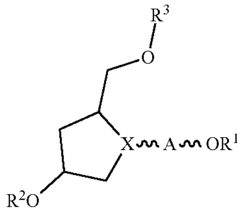

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the molecule is of the formula:

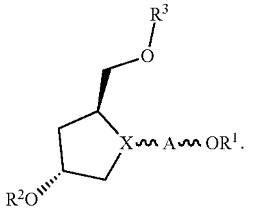

In certain embodiments, the molecule is of the formula:

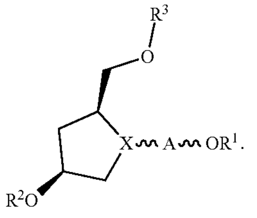

In certain embodiments, the molecule is of the formula:

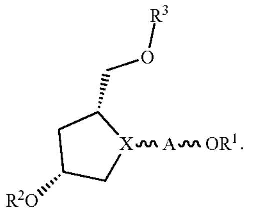

In certain embodiments, the molecule is of the formula:

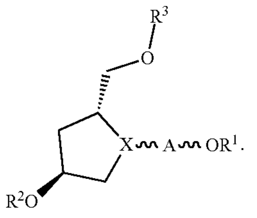

In certain embodiments, X is N. In certain embodiments, X is CH.

In certain embodiments, A is a bond. In certain embodiments, A is substituted or unsubstituted, cyclic or acyclic, branched or unbranched aliphatic. In certain embodiments, A is acyclic, substituted or unsubstituted, branched or unbranched aliphatic. In certain embodiments, A is acyclic, substituted, branched or unbranched aliphatic. In certain embodiments, A is acyclic, substituted, unbranched aliphatic. In certain embodiments, A is acyclic, substituted, unbranched alkyl. In certain embodiments, A is acyclic, substituted, unbranched $C_{1-20}$ alkyl. In certain embodiments, A is acyclic, substituted, unbranched $C_{1-12}$ alkyl. In certain embodiments, A is acyclic, substituted, unbranched $C_{1-10}$ alkyl. In certain embodiments, A is acyclic, substituted, unbranched $C_{1-8}$ alkyl. In certain embodiments, A is acyclic, substituted, unbranched $C_{1-6}$ alkyl. In certain embodiments, A is substituted or unsubstituted, cyclic or acyclic, branched or unbranched heteroaliphatic. In certain embodiments, A is acyclic, substituted or unsubstituted, branched or unbranched heteroaliphatic. In certain embodiments, A is acyclic, substituted, branched or unbranched heteroaliphatic. In certain embodiments, A is acyclic, substituted, unbranched heteroaliphatic.

In certain embodiments, A is of the formula:

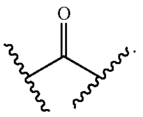 [SMILES: *C(*)=O]

In certain embodiments, A is of one of the formulae:

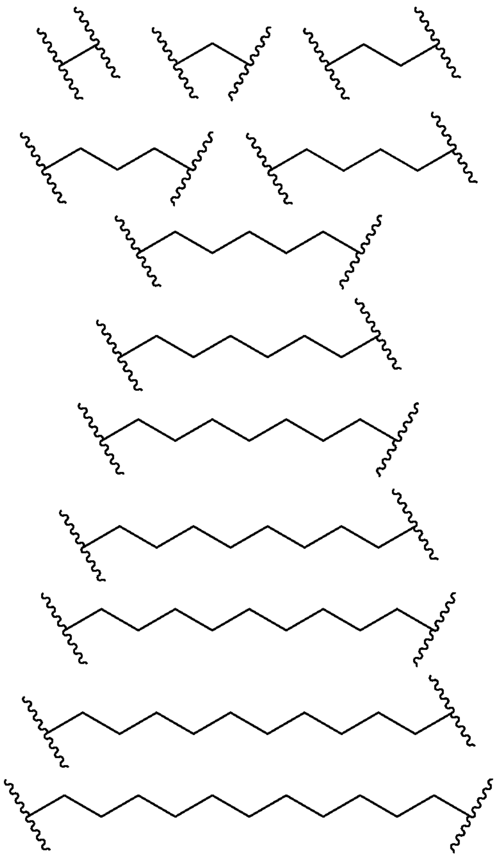

-continued

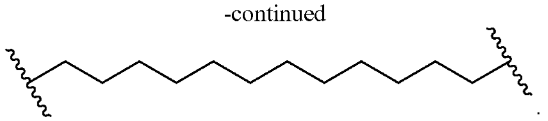

In certain embodiments, A is of one of the formulae:

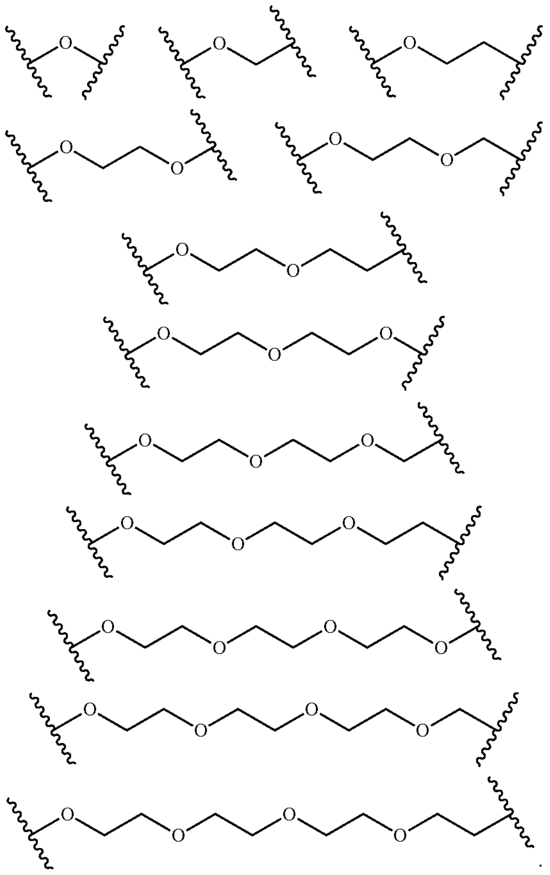

In certain embodiments, A is of one of the formulae:

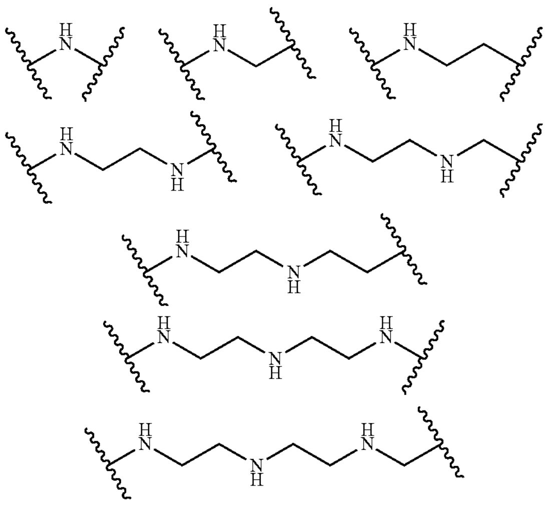

-continued

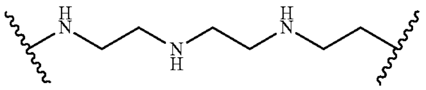

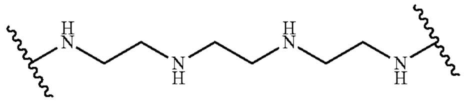

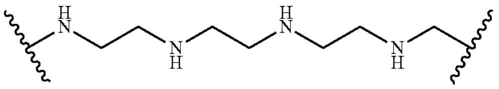

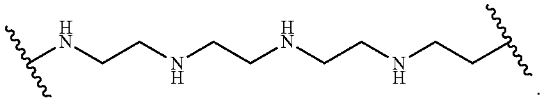

In certain embodiments, A is of the formula:

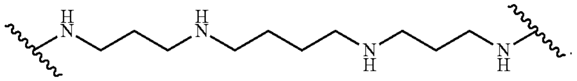 [SMILES: *NCCCNCCCCNCCCN*]

In certain embodiments, A is of the formula:

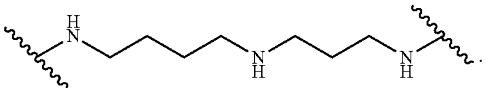 [SMILES: *NCCCCNCCCN*]

In certain embodiments, A is of the formula:

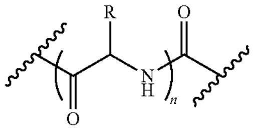

wherein each occurrence of R is independently the side chain of a natural or unnatural amino acid; and n is an integer between 1 and 20, inclusive. In certain embodiments, A is of the formula:

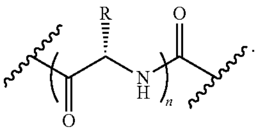

In certain embodiments, each occurrence of R is independently the side chain of a natural amino acid. In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

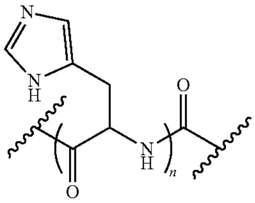

wherein n is an integer between 1 and 20, inclusive. In certain embodiments, A is of the formula:

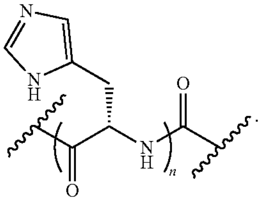

In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

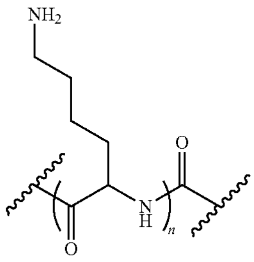

wherein n is an integer between 1 and 20, inclusive. In certain embodiments, A is of the formula:

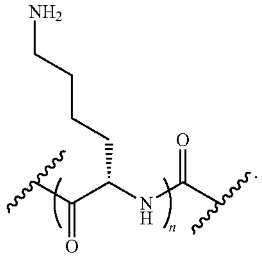

In certain embodiments, n is an integer between 1 and 15, inclusive. In certain embodiments, n is an integer between 1 and 10, inclusive. In certain embodiments, n is an integer between 1 and 5, inclusive.

In certain embodiments, the molecule is of the formula:

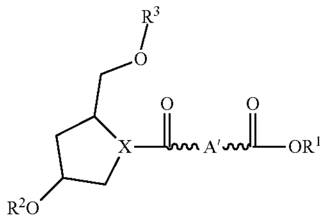

wherein X, $R^1$, $R^2$, and $R^3$ are as defined herein; and

A' is substituted or unsubstituted, cyclic or acyclic, branched or unbranched aliphatic; or substituted or unsubstituted, cyclic or acyclic, branched or unbranched heteroaliphatic.

In certain embodiments, A' is of one of the formulae:

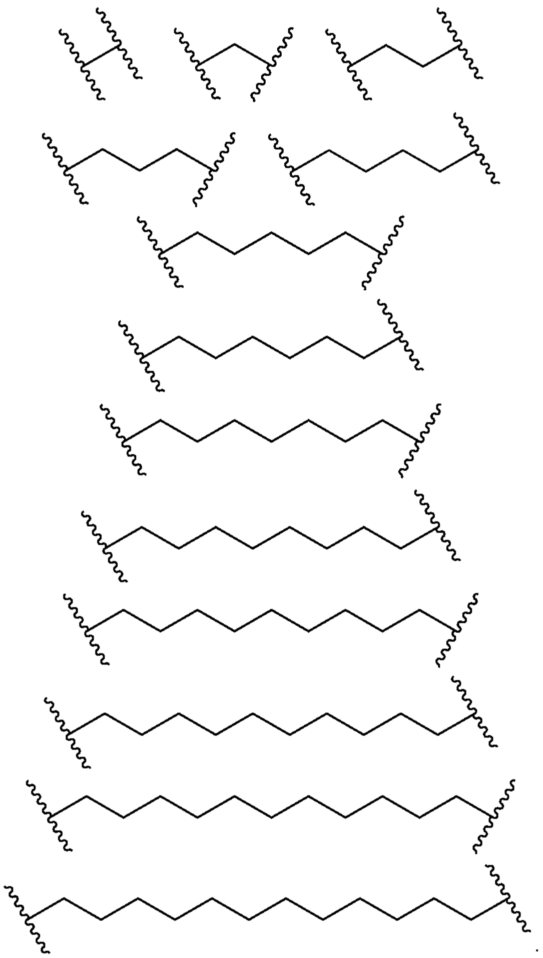

In certain embodiments, A is of one of the formulae:

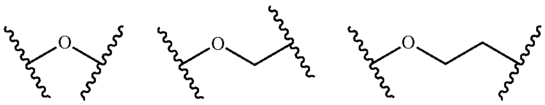

-continued

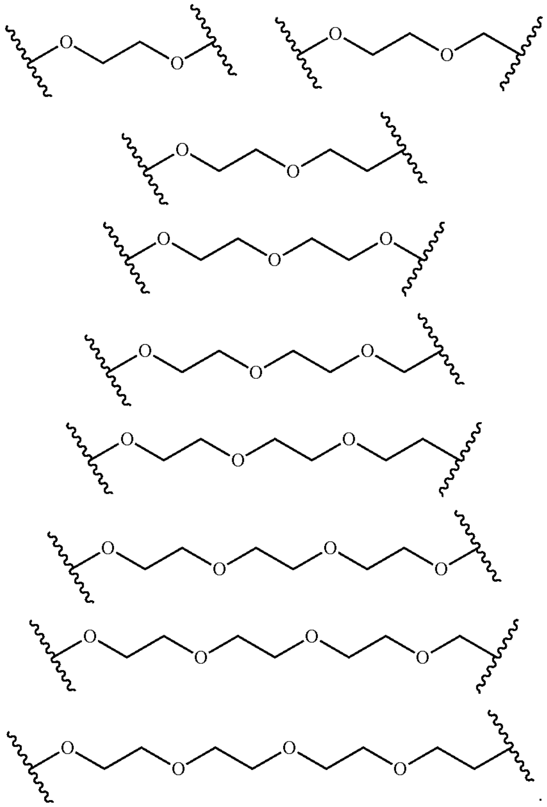

In certain embodiments, A is of one of the formulae:

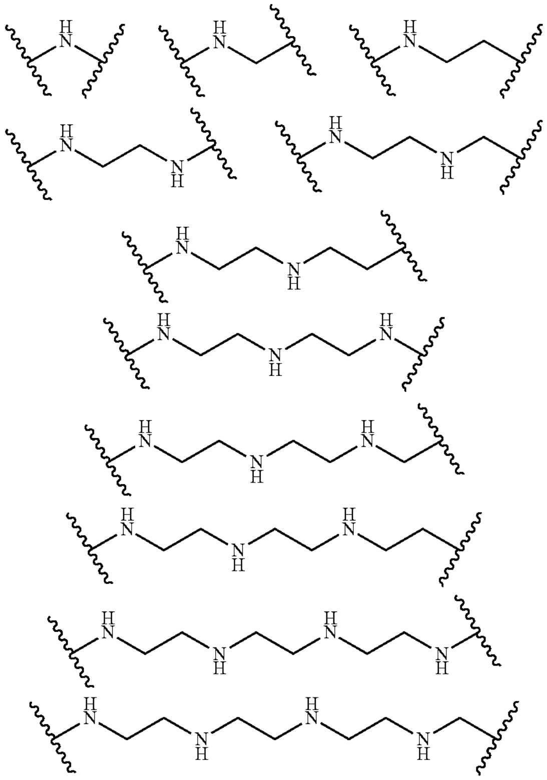

-continued

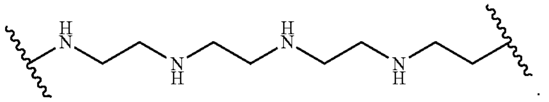

.

In certain embodiments, A is of the formula:

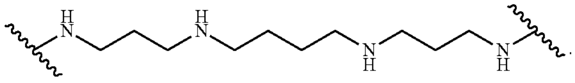 [SMILES: *NCCCNCCCCNCCCN*]

In certain embodiments, A is of the formula:

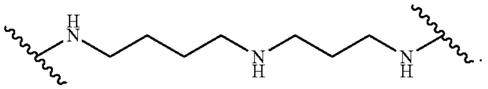 [SMILES: *NCCCCNCCCN*]

In certain embodiments, $R^1$ is a steroid. In certain embodiments, $R^1$ is a cholesterol. In certain embodiments, $R^1$ is a lipophilic vitamin. In certain embodiments, $R^1$ s a vitamin A. In certain embodiments, $R^1$ is a vitamin E.

In certain embodiments, $R^1$ is of the formula:

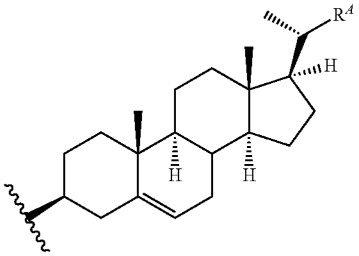

wherein $R^A$ is substituted or unsubstituted, cyclic or acyclic, branched or unbranched aliphatic; or substituted or unsubstituted, cyclic or acyclic, branched or unbranched heteroaliphatic.

In certain embodiments, $R^1$ is of the formula:

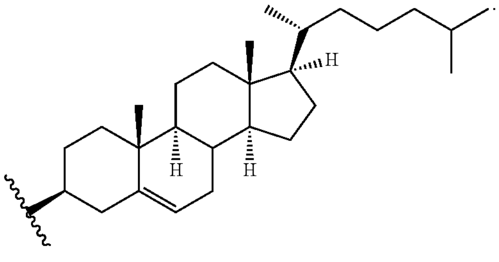

In certain embodiments, $R^1$ is of the formula:

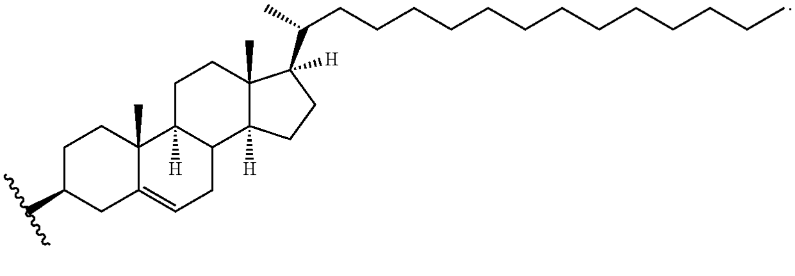

In certain embodiments, $R^1$ is of the formula:

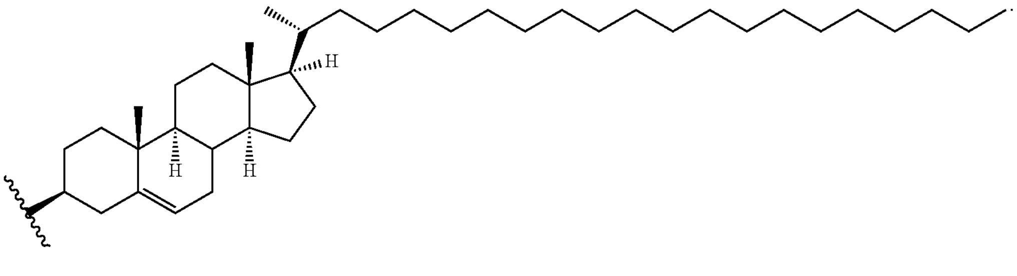

In certain embodiments, $R^1$ is of the formula:

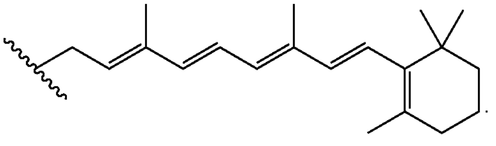 [SMILES: *C/C=C(C)/C=C/C=C(C)/C=C/C1=C(C)CCCC1(C)C]

In certain embodiments, $R^1$ is of the formula:

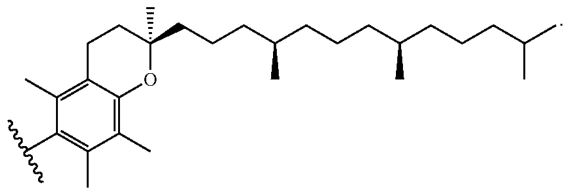 [SMILES: *c1c(C)c(C)c2c(c1C)CC[C@@](C)(CCC[C@H](C)CCC[C@H](C)CCCC(C)C)O2]

In certain embodiments, the nucleic acid molecule is of the formula:

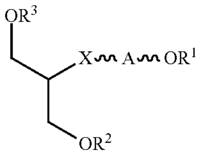

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the nucleic acid molecule is of the formula:

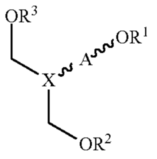

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the nucleic acid molecule is of the formula:

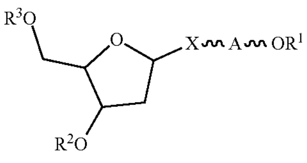

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid. In certain embodiments, the nucleic acid molecule is of the formula:

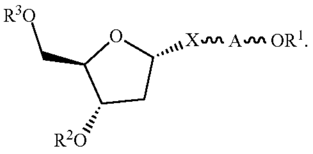

In certain embodiments, the nucleic acid molecule is of the formula:

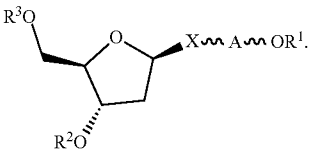

In certain embodiments, the nucleic acid molecule is of the formula:

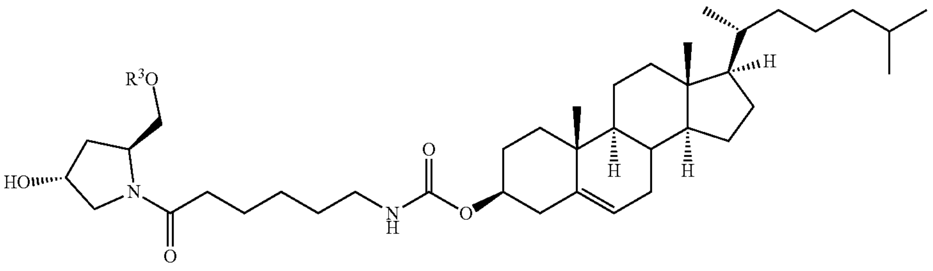

wherein $R^3$ is a nucleic acid.

In certain embodiments, the nucleic acid molecule is of the formula:

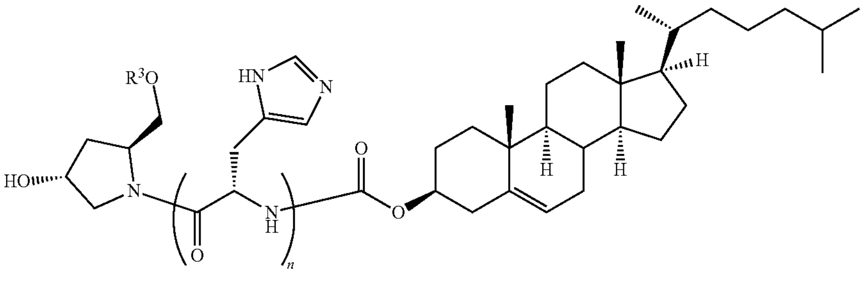

wherein $R^3$ is a nucleic acid; and n is an integer between 1 and 20, inclusive.

In certain embodiments, the nucleic acid molecule is of the formula:

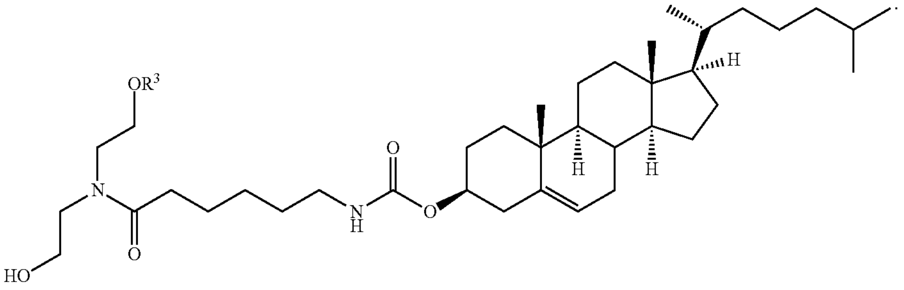

In certain embodiments, the nucleic acid molecule is of the formula:

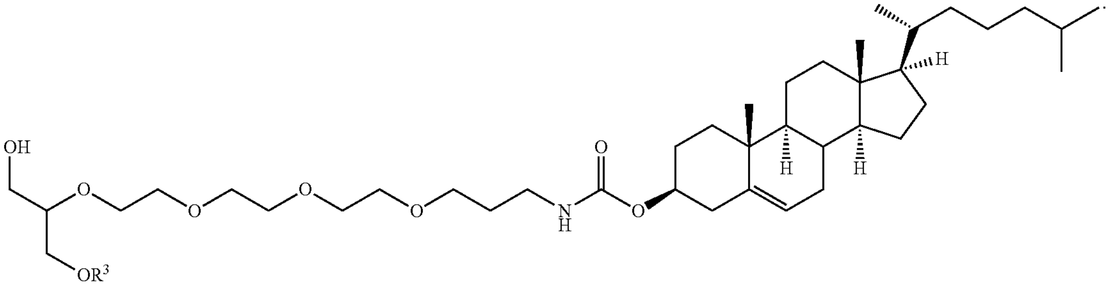

In certain embodiments, the nucleic acid molecule is of the formula:

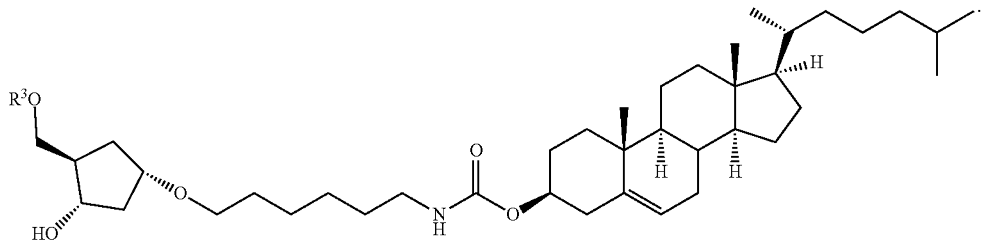

In certain embodiments, the nucleic acid molecule is of the formula:

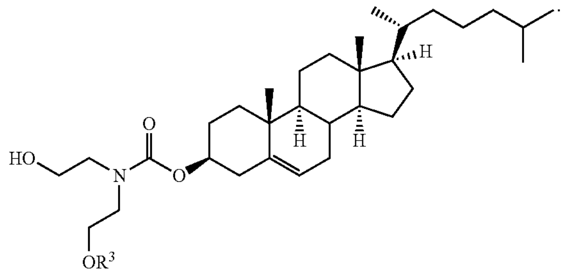

In certain embodiments, the nucleic acid molecule is of the formula:

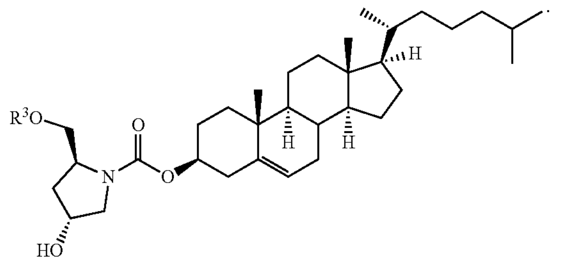

As used herein, the term "linkage" includes a naturally occurring, unmodified phosphodiester moiety (—O—($PO^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolyzable linkages are preferred, such as phosphorothioate linkages.

In certain embodiments, oligonucleotides of the invention comprise hydrophobically modified nucleotides or "hydrophobic modifications." As used herein "hydrophobic modifications" refers to bases that are modified such that (1) overall hydrophobicity of the base is significantly increased, and/or (2) the base is still capable of forming close to regular Watson—Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl ($C_8H_6N$) $CH_2CH(NH_2)CO$), Isobutyl, butyl, aminobenzyl; phenyl; and naphthyl.

Other types of conjugates that can be attached to the end (3' or 5' end), a loop region, or any other parts of a chemically modified double stranded nucleic acid molecule include a sterol, sterol type molecule, peptide, small molecule, protein, etc. In some embodiments, a chemically modified double stranded nucleic acid molecule, such as an sd-rxRNA (INTASYL™), may contain more than one conjugate (same or different chemical nature). In some embodiments, the conjugate is cholesterol.

In some embodiments, the first nucleotide relative to the 5' end of the guide strand has a 2'-O-methyl modification, optionally wherein the 2'-O-methyl modification is a 5P-2'O-methyl U modification, or a 5' vinyl phosphonate 2'-O-methyl U modification. Another way to increase target gene specificity, or to reduce off-target silencing effect, is to introduce a 2'-modification (such as the 2'-O methyl modification) at a position corresponding to the second 5'-end nucleotide of the guide sequence. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC. In some embodiments, high levels of phosphorothioate modification can lead to improved delivery. In some embodiments, the guide and/or passenger strand is completely phosphorothioated.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. The chemical modification patterns may include a combination of ribose, backbone, hydrophobic nucleoside and conjugate type of modifications. In addition, in some of the embodiments, the 5' end of the single polynucleotide may be chemically phosphorylated.

In yet another embodiment, the present invention provides a description of the chemical modification patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. The chemical modification patterns may include a combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In some embodiments, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

Without wishing to be bound by any particular theory, the inventors believe that the particular patterns of modifications on the passenger strand and guide strand of the double stranded nucleic acid molecules described herein (e.g., INTASYL™) facilitate entry of the guide strand into the nucleus, where the guide strand mediates gene silencing (e.g., silencing of target genes, such as BRD4).

Without wishing to be bound by any theory, several potential mechanisms of action could account for this activity. For example, in some embodiments, the guide strand (e.g., antisense strand) of the nucleic acid molecule (e.g., INTASYL™) may dissociate from the passenger strand and enter into the nucleus as a single strand. Once in the nucleus the single stranded guide strand may associate with RNAse H or another ribonuclease and cleave the target (e.g., BRD4) ("Antisense mechanism of action"). In some embodiments, the guide strand (e.g., antisense strand) of the nucleic acid molecule (e.g., INTASYL™) may associate with an Argonaute (Ago) protein in the cytoplasm or outside the nucleus, forming a loaded Ago complex. This loaded Ago complex may translocate into the nucleus and then cleave the target (e.g., BRD4). In some embodiments, both strands (e.g. a duplex) of the nucleic acid molecule (e.g., INTASYL™) may enter the nucleus and the guide strand may associate with RNAse H, an Ago protein or another ribonuclease and cleaves the target (e.g., BRD4).

The skilled artisan appreciates that the sense strand of the double stranded molecules described herein (e.g., INTASYL™ sense strand) is not limited to delivery of a guide strand of the double stranded nucleic acid molecule described herein. Rather, in some embodiments, a passenger strand described herein is joined (e.g., covalently bound, non-covalently bound, conjugated, hybridized via a region of complementarity, etc.) to certain molecules (e.g., antisense oligonucleotides, ASO) for the purpose of targeting said other molecule to the nucleus of a cell. In some embodiments, the molecule joined to a sense strand described herein is a synthetic antisense oligonucleotide (ASO). In some embodiments, the sense strand joined to an anti-sense oligonucleotide is between 8-15 nucleotides long, chemically modified, and comprises a hydrophobic conjugate.

Without wishing to be bound by any particular theory, an ASO can be joined to a complementary passenger strand by hydrogen bonding. Accordingly, in some aspects, the disclosure provides a method of delivering a nucleic acid molecule to a cell, the method comprising administering an isolated nucleic acid molecule to a cell, wherein the isolated nucleic acid comprises a sense strand which is complementary to an antisense oligonucleotide (ASO), wherein the sense strand is between 8-15 nucleotides in length, comprises at least two phosphorothioate modifications, at least 50% of the pyrimidines in the sense strand are modified, and wherein the molecule comprises a hydrophobic conjugate.

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In some embodiments, the oligonucleotide compositions of the invention are contacted with bacterial cells. In some embodiments, the oligonucleotide compositions of the invention are contacted with eukaryotic cells (e.g., plant cell, mammalian cell, arthropod cell, such as insect cell). In some embodiments, the oligonucleotide compositions of the invention are contacted with stem cells. In some embodiments, the oligonucleotide compositions of the invention are contacted with immune cells, such as T-cells (e.g., CD8+ T-cells). In some embodiments, the T-cells are $T_{SCM}$ or $T_{CM}$ T-cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject, or ex vivo. In some embodiments, oligonucleotides are administered topically or through electroporation. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the chemically modified double stranded nucleic acid molecules of the invention may be delivered by using various beta-glucan containing particles, referred to as GeRPs (glucan encapsulated RNA loaded particle), described in, and incorporated by reference from, U.S. Provisional Application No. 61/310,611, filed on Mar. 4, 2010 and entitled "Formulations and Methods for Targeted Delivery to Phagocyte Cells." Such particles are also described in, and incorporated by reference from US Patent Publications US 2005/0281781 A1, and US 2010/0040656, and in PCT publications WO 2006/007372, and WO 2007/050643. The chemically modified double stranded nucleic acid molecule may be hydrophobically modified and optionally may be associated with a lipid and/or amphiphilic peptide. In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Glucan particles can be derived from insoluble components of fungal cell walls such as yeast cell walls. In some embodiments, the yeast is Baker's yeast. Yeast-derived glucan molecules can include one or more of ß-(1,3)-Glucan, ß-(1,6)-Glucan, mannan and chitin. In some embodiments, a glucan particle comprises a hollow yeast cell wall whereby the particle maintains a three dimensional structure resembling a cell, within which it can complex with or encapsulate a molecule such as an RNA molecule. Some of the advantages associated with the use of yeast cell wall particles are availability of the components, their biodegradable nature, and their ability to be targeted to phagocytic cells.

In some embodiments, glucan particles can be prepared by extraction of insoluble components from cell walls, for example by extracting Baker's yeast (Fleischmann's) with 1M NaOH/pH 4.0 $H_2O$, followed by washing and drying. Methods of preparing yeast cell wall particles are discussed in, and incorporated by reference from U.S. Pat. Nos. 4,810,646, 4,992,540, 5,082,936, 5,028,703, 5,032,401, 5,322,841, 5,401,727, 5,504,079, 5,607,677, 5,968,811, 6,242,594, 6,444,448, 6,476,003, US Patent Publications 2003/0216346, 2004/0014715 and 2010/0040656, and PCT published application WO02/12348.

Protocols for preparing glucan particles are also described in, and incorporated by reference from, the following references: Soto and Ostroff (2008), "Characterization of multilayered nanoparticles encapsulated in yeast cell wall particles for DNA delivery." *Bioconjug Chem* 19(4):840-8; Soto and Ostroff (2007), "Oral Macrophage Mediated Gene Delivery System," *Nanotech*, Volume 2, Chapter 5 ("Drug Delivery"), pages 378-381; and Li et al. (2007), "Yeast glucan particles activate murine resident macrophages to secrete proinflammatory cytokines via MyD88- and Syk kinase-dependent pathways." *Clinical Immunology* 124(2): 170-181.

Glucan containing particles such as yeast cell wall particles can also be obtained commercially. Several non-limiting examples include: Nutricell MOS 55 from Biorigin (Sao Paolo, Brazil), SAF-Mannan (SAF Agri, Minneapolis, Minn.), Nutrex (Sensient Technologies, Milwaukee, Wis.), alkali-extracted particles such as those produced by Nutricepts (Nutricepts Inc., Burnsville, Minn.) and ASA Biotech, acid-extracted WGP particles from Biopolymer Engineering, and organic solvent-extracted particles such as Adjuvax™ from Alpha-beta Technology, Inc. (Worcester, Mass.) and microparticulate glucan from Novogen (Stamford, Conn.).

Glucan particles such as yeast cell wall particles can have varying levels of purity depending on the method of production and/or extraction. In some instances, particles are alkali-extracted, acid-extracted or organic solvent-extracted to remove intracellular components and/or the outer mannoprotein layer of the cell wall. Such protocols can produce particles that have a glucan (w/w) content in the range of 50%-90%. In some instances, a particle of lower purity, meaning lower glucan w/w content may be preferred, while in other embodiments, a particle of higher purity, meaning higher glucan w/w content may be preferred.

Glucan particles, such as yeast cell wall particles, can have a natural lipid content. For example, the particles can contain 1%, 2%, 3%, 4%, 5%, 6%, 7%, 8%, 9%, 10%, 11%, 12%, 13%, 14%, 15%, 16%, 17%, 18%, 19%, 20% or more than 20% w/w lipid. In some instances, the presence of natural lipids may assist in complexation or capture of RNA molecules.

Glucan containing particles typically have a diameter of approximately 2-4 microns, although particles with a diameter of less than 2 microns or greater than 4 microns are also compatible with aspects of the invention.

The RNA molecule(s) to be delivered can be complexed or "trapped" within the shell of the glucan particle. The shell or RNA component of the particle can be labeled for visualization, as described in, and incorporated by reference from, Soto and Ostroff (2008) *Bioconjug Chem* 19:840. Methods of loading GeRPs are discussed further below.

The protocol used for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Immunomodulatory Compositions and Methods of Producing the Same

In some embodiments, chemically-modified double stranded nucleic acid molecules (e.g., INTASYL™ molecules) described herein are useful for producing specific cell subtypes or T-cell subtypes for immunomodulatory compositions. As used herein, an "immunomodulatory composition" is a composition comprising a host cell that comprises a chemically-modified nucleic acid molecule as described herein and/or a host cell that has been treated with a chemically-modified nucleic acid molecule as described herein. An immunomodulatory composition can optionally further comprise one or more pharmaceutically acceptable excipients or carriers. Without wishing to be bound by any particular theory, immunomodulatory compositions as described by the disclosure are characterized by a population of immune cells (e.g., T-cells, NK-cells, antigen-presenting cells (APC), dendritic cells (DC), stem cells (SC), induced pluripotent stem cells (iPSC), etc.) that have been engineered to have an enriched population of a particular cell subtype (e.g., T-cell subtype, such as $T_{SCM}$ or $T_{CM}$ T-cells), and are thus useful, in some embodiments, for modulating (e.g., stimulating or inhibiting) the immune response of a subject.

As used herein, a "host cell" is a cell to which one or more chemically-modified double stranded nucleic acid molecules have been introduced. Typically, a host cell is a mammalian cell, for example a human cell, mouse cell, rat cell, pig cell, etc. However, in some embodiments, a host cell is a non-mammalian cell, for example a prokaryotic cell (e.g., bacterial cell), yeast cell, insect cell, etc. Generally, a host cell is derived from a donor, such as a healthy donor (e.g., the cell to which the chemically-modified double stranded nucleic acid is introduced is taken from a donor, such as a healthy donor). For example, a cell or cells may be isolated from a biological sample obtained from a donor, such as a healthy donor, such as bone marrow or blood. As used herein "healthy donor" refers to a subject that does not have, or is not suspected of having, a proliferative disorder or an infectious disease (e.g., a bacterial, viral, or parasitic infection). However, in some embodiments, a host cell is derived from a subject having (or suspected of having) a proliferative disease or an infectious disease, for example in the context of autologous cell therapy.

In some embodiments a cell (e.g., a host cell) is an immune cell, for example a T-cell, B-cell, dendritic cell (DC), granulocyte, natural killer cell, macrophage, etc. In some embodiments, a cell (e.g., a host cell) is a cell that is capable of differentiating into an immune cell, such as a stem cell (SC) or induced pluripotent stem cell (iPSC). In some embodiments, a cell (e.g., a host cell) is a stem cell memory T-cell, for example as described in, and incorporated by reference from, Gattinoni et al. (2017) *Nature Medicine* 23; 18-27.

In some embodiments, a cell (e.g., a host cell) is a T-cell, such as a killer T-cell, helper T-cell, a regulatory T-cell, or a tumor infiltrating lymphocyte (TIL). In some embodiments the T-cell is a killer T-cell (e.g., a CD8+ T-cell). In some embodiments, the T-cell is a helper T-cell (e.g., a CD4+ T-cell). In some embodiments, a T-cell is an activated T-cell (e.g., a T-cell that has been presented with a peptide antigen by MHC class II molecules on an antigen presenting cell).

In some embodiments, a T-cell comprises one or more transgenes expressing a high affinity T-cell receptor (TCR) and/or a chimeric antibody receptor (CAR).

In some aspects, the disclosure relates to the discovery that introducing one or more chemically-modified double stranded nucleic acid molecules (e.g., one or more INTASYL™ molecules) of the disclosure to a cell (e.g., an immune cell obtained from a donor) to produce a host cell characterized by a significant reduction of one or more signal transduction/transcription factor, epigenetic, metabolic and/or co-inhibitory/negative regulatory protein (e.g., BRD4, etc.) expression or activity in the host cell. In some embodiments, a host cell is characterized by between about 5% and about 50% reduced expression of an immune checkpoint protein relative to a cell (e.g., an immune cell of the same cell type) that does not comprise the chemically-modified double stranded nucleic acid molecules. In some embodiments, a host cell is characterized by greater than 50% (e.g., 51%, 52%, 53%, 54%, 55%, 60%, 70%, 75%, 80%, 85%, 90%, 95%, 99%, 100%, or any percentage between 51% and 100%, including all values in between) reduced expression of a differentiation related target (e.g. signaling molecule, kinase/phosphatase, transcription factor, epigenetic modulator, metabolic and regulatory target) relative to a cell (e.g., an immune cell of the same cell type) that does not comprise the chemically-modified double stranded nucleic acid molecules (e.g., an immune cell of a subject having or suspected of having a proliferative disease or an infectious disease).

In some embodiments, an immunomodulatory composition as described by the disclosure comprises a plurality of host cells. In some embodiments, the plurality of host cells is about 10,000 host cells per kilogram, about 50,000 host cells per kilogram, about 100,000 host cells per kilogram, about 250,000 host cells per kilogram, about 500,000 host cells per kilogram, about $1\times10^6$ host cells per kilogram, about $5\times10^6$ host cells per kilogram, about $1\times10^7$ host cells per kilogram, about $1\times10^8$ host cells per kilogram, about $1\times10^9$ host cells per kilogram, or more than $1\times10^9$ host cells per kilogram. In some embodiments, the plurality of host cells is between about $1\times10^5$ and $1\times10^{14}$ host cells per kilogram.

In some aspects, the disclosure provides methods for producing an immunomodulatory composition as described by the disclosure. In some embodiments, the methods comprise, introducing into a cell one or more chemically-modified double stranded nucleic acid molecules (e.g., INTASYL™), wherein the chemically-modified double stranded nucleic acid molecules target BRD4, thereby producing a host cell with a specific cell subtype or T-cell subtype (e.g., $T_{SCM}$ or $T_{CM}$).

Methods of producing immunomodulatory compositions (e.g., producing a host cell or populations of host cells) may be carried out in vitro, ex vivo, or in vivo, in, for example, mammalian cells in culture, such as a human cell in culture. In some embodiments, target cells (e.g., cells obtained from a donor) may be contacted in the presence of a delivery reagent, such as a lipid (e.g., a cationic lipid) or a liposome to facilitate entry of the chemically-modified double stranded nucleic acid molecules into the cell, as described in further detail elsewhere in the disclosure.

Carriers and Complexing Agents

The disclosure further relates to compositions comprising RNAi constructs as described herein, and a pharmaceutically acceptable carrier or diluent. In some aspects, the disclosure relates to immunomodulatory compositions comprising the RNAi constructs described herein, and a pharmaceutically acceptable carrier.

As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

For example, in some embodiments, oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types (e.g., immune cells, such as T-cells).

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as dicetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (e.g., a cationic lipid). The presence of this positively charged lipid is believed to be essential for obtaining a high degree of oligonucleotide loading and for enhancing liposome fusogenic properties. Several methods have been performed and published to identify functional positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (e.g., elevation in liver enzymes) at concentrations only slightly higher than concentration required to achieve RNA silencing.

Nucleic acids associated with the invention can be hydrophobically modified and can be encompassed within neutral nanotransporters. Further description of neutral nanotransporters is incorporated by reference from PCT Application PCT/US2009/005251, filed on Sep. 22, 2009, and entitled "Neutral Nanotransporters." Such particles enable quantitative oligonucleotide incorporation into non-charged lipid mixtures. The lack of toxic levels of cationic lipids in such neutral nanotransporter compositions is an important feature.

As demonstrated in PCT/US2009/005251, oligonucleotides can effectively be incorporated into a lipid mixture that is free of cationic lipids and such a composition can effectively deliver a therapeutic oligonucleotide to a cell in a manner that it is functional. For example, a high level of activity was observed when the fatty mixture was composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non-charged formulation.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is built into the oligonucleotide itself, enables efficient encapsulation of oligonucleotide in neutral lipid particles.

In some aspects, stable particles ranging in size from 50 to 140 nm can be formed upon complexing of hydrophobic oligonucleotides with preferred formulations. The formulation by itself typically does not form small particles, but rather, forms agglomerates, which are transformed into stable 50-120 nm particles upon addition of the hydrophobic modified oligonucleotide.

In some embodiments, neutral nanotransporter compositions include a hydrophobic modified polynucleotide, a neutral fatty mixture, and optionally a cargo molecule. A "hydrophobic modified polynucleotide" as used herein is a polynucleotide of the invention (e.g., sd-rxRNA) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridones, biotin, coumarin, fluorescein, rhodamine, Texas-Red, digoxygenin, dimethoxytrityl, t-butyldimethylsilyl, t-butyldiphenylsilyl, cyanine dyes (e.g., Cy3 or Cy5), Hoechst 33258 dye, psoralen, or ibuprofen. The cholesterol moiety may be reduced (e.g., as in cholestan) or may be substituted (e.g., by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethyleneglycol (spacer 18), or alkane-diol, such as butanediol. The spacer units are preferably linked by phosphodiester or phosphorothioate bonds. The linker units may appear just once in the molecule or may be incorporated several times, e.g., via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more than 200 different known PhytoSterols.

For purposes of the present invention, the term "sterol side chain" refers to a chemical composition of a side chain attached at the position 17 of sterol-type molecule. In a standard definition, sterols are limited to a 4 ring structure carrying an 8 carbon chain at position 17. In this invention, the sterol type molecules with side chain longer and shorter than conventional are described. The side chain may be branched or contain double back bones.

Thus, sterols useful in the invention, for example, include cholesterols, as well as unique sterols in which position 17 has attached side chain of 2-7 or longer than 9 carbons. In some embodiments the length of the polycarbon tail is varied between 5 and 9 carbons. Such conjugates may have significantly better in vivo efficacy, in particular delivery to liver. These types of molecules are expected to work at concentrations 5 to 9 fold lower then oligonucleotides conjugated to conventional cholesterols.

Alternatively the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with specific chemical modification patterns of the polynucleotide (as described herein in detail), containing but not limited to hydrophobic modifications, phosphorothioate modifications, and 2' ribo modifications.

In another embodiment the sterol type molecule may be a naturally occurring PhytoSterols. The polycarbon chain may be longer than 9 and may be linear, branched and/or contain double bonds. Some PhytoSterol-containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non-charged fatty acids and phospholipids. The neutral fatty mixture may include cationic lipids as long as they are present in an amount that does not cause toxicity. In some embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleoylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soybean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. In some embodiments, vitamin A or E is used. Complexes are formed at different oligonucleotide concentrations, with higher concentrations favoring more efficient complex formation.

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more than 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

In yet another embodiment of the present invention, the alteration of the composition of the fat emulsion is used as a way to alter tissue distribution of hydrophobically modified polynucleotides. This methodology provides for the specific delivery of the polynucleotides to particular tissues.

In another embodiment the fat emulsions of the cargo molecule contain more than 70% of Linoleic acid ($C_{18}H_{32}O_2$) and/or cardiolipin.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms.

Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[l-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to improve uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to improve uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. USA.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine-tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Other carriers for in vitro and/or in vivo delivery of RNAi reagents are known in the art, and can be used to deliver the subject RNAi constructs (e.g., to a host cell, such as a T-cell). See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Therapeutic Methods

In some aspects, the disclosure provides methods of treating a proliferative disease or an infectious disease by administering to a subject (e.g., a subject having or suspected of having a proliferative disease or an infectious disease) an immunomodulatory composition as described by the disclosure (e.g., an immunomodulatory composition comprising one or more host cells of a particular cell subtype or T-cell subtype). In some embodiments, immunomodulatory compositions as described herein are characterized as population of immune cells (e.g., T-cells, NK-cells, antigen-presenting cells (APC), dendritic cells (DC), stem cells (SC), induced pluripotent stem cells (iPSC), etc.) having reduced (e.g., inhibited) expression or activity of one or more genes associated with controlling the differentiation process of T-cells (e.g., BRD4).

As used herein, a "proliferative disease" refers to diseases and disorders characterized by excessive proliferation of cells and turnover of cellular matrix, including cancer, atherlorosclerosis, rheumatoid arthritis, psoriasis, idiopathic pulmonary fibrosis, scleroderma, cirrhosis of the liver, etc. Examples of cancers include but are not limited to neoplasms, malignant tumors, metastases, or any other disease or disorder characterized by uncontrolled cell growth such that it would be considered cancerous. In some embodiments, the cancer is a primary cancer. In some embodiments, the cancer is a metastatic cancer. Examples of cancers include biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas; tumor mutational burden high tumors; choriocarcinomas; stromal tumors and germ cell tumors; thyroid cancer including thyroid adenocarcinoma and medullar carcinoma; and renal cancer including adenocarcinoma and Wilms' tumor. In some embodiments, the cancer is selected from the group consisting of: small cell lung cancer, colon cancer, breast cancer, lung cancer, prostate cancer, ovarian cancer, pancreatic cancer, melanoma, hematological malignancy such as chronic myeloid leukemia, etc. In some embodiments, a subject has one type of cancer. In some embodiments, a subject has more than one type (e.g., 2, 3, 4, 5, or more types) of cancer. In some embodiments, the cancer includes small cell lung cancer, colon cancer, breast cancer, lung cancer, prostate cancer, ovarian cancer, pancreatic cancer, melanoma, or hematological malignancy such as chronic myeloid leukemia (CML).

As used herein, the term "infectious disease" refers to diseases and disorders that result from infection of a subject with a pathogen. Examples of human pathogens include but are not limited to certain bacteria (e.g., certain strains of *E. coli, Salmonella*, etc.), viruses (HIV, HCV, influenza, etc.), parasites (protozoans, helminths, amoeba, etc.), yeasts (e.g., certain *Candida* species, etc.), and fungi (e.g., certain *Aspergillus* species).

Examples of subjects include mammals, e.g., humans and other primates; cows, pigs, horses, and farming (agricultural) animals; dogs, cats, and other domesticated pets; mice, rats, and transgenic non-human animals.

In some embodiments, immunomodulatory compositions as described by the disclosure are administered to a subject by adoptive cell transfer (ACT) therapeutic methods. Examples of ACT modalities include but are not limited to autologous cell therapy (e.g., a subject's own cells are removed, genetically-modified, and returned to the subject), tumor infiltrating lymphocytes (TILs) and heterologous cell therapy (e.g., cells are removed from a donor, genetically-modified, and placed into a recipient). In some embodiments, cells utilized in ACT therapeutic methods may be genetically-modified to express chimeric antigen receptors (CARs), which are engineered T-cell receptors displaying specificity against a target antigen based on a selected antibody moiety. Accordingly, in some embodiments, CAR T-cells (e.g. CARTs) may be transfected with a chemically-modified double stranded nucleic acid using methods described herein for the purpose of ACT therapy.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; intratumorally; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension and include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Drug delivery vehicles can be chosen e.g., for in vitro, for systemic administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an immunomodulatory composition and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimens may be adjusted to provide the target therapeutic responses. For example, the immunomodulatory composition may be repeatedly administered, e.g., several doses may be administered daily, or the dose may be proportionally reduced as indicated by the exigencies of the therapeutic situation. One of ordinary skill in the art will readily be able to determine appropriate doses and schedules of administration of the subject chemically-modified double stranded nucleic acid molecules or immunomodulatory compositions, whether they are to be administered to cells or to subjects.

Administration of immunomodulatory compositions, such as through intradermal injection or subcutaneous delivery, can be improved through testing of dosing regimens. In some embodiments, a single administration is sufficient. To further prolong the effect of the administered immunomodulatory compositions, the compositions can be administered in a slow-release formulation or device, as would be familiar to one of ordinary skill in the art.

In other embodiments, the chemically-modified double stranded nucleic acid molecules or immunomodulatory compositions are administered multiple times. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours, 10 hours, 12 hours or more than twelve hours. It can be administered 1, 2, 3, 4, 5, 6, 7, 8, 9, 10 or more than 10 times per day.

Aspects of the invention relate to administering immunomodulatory compositions to a subject. In some instances, the subject is a patient and administering the immunomodulatory composition involves administering the composition in a doctor's office.

In some embodiments, more than one immunomodulatory composition is administered simultaneously. For example, a composition may be administered that contains 1, 2, 3, 4, 5, 6, 7, 8, 9, 10 or more than 10 different compositions. In certain embodiments, a composition comprises 2 or 3 different immunomodulatory compositions.

Self-Delivering RNAi Immunotherapeutic Agents

As described in U.S. Patent Publication No. US 2016/0304873, the entire contents of which are incorporated herein by reference, immunotherapeutic agents were produced by treating cells with particular INTASYL™ agents designed to target and knock down specific genes involved in immune suppression mechanisms. Several cells and cell lines have been successfully treated with INTASYL™ compounds and have been shown to knock down at least 70% of targeted gene expression in the specified human cells.

These studies demonstrated utility of these immunomodulatory agents to suppress expression of target genes in cells normally very resistant to transfection, and suggested the agents are capable of reducing expression of target cells in any cell type.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Compositions and methods described herein are further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Identification of BRD4 Targeting INTASYL™ Sequences

The BRD4 gene was analyzed using a proprietary algorithm to identify preferred INTASYL™ molecules targeting BRD4 sequences and target regions. Non-limiting examples of BRD4 target sequences and/or INTASYL™ sequences are shown in Tables 1 and 2.

Example 2: Two Point Dose Response of Chemically-Modified INTASYL™ Molecules Targeting BRD4 in A549 Cells A549 cells were obtained from ATCC and cultured in F12K media with 10% Fetal Bovine Serum and 1% Pen/Strep. Cells were plated in 96 wells 24 hours prior to transfection. Chemically modified INTASYL™ molecules targeting BRD4 were prepared by diluting the INTASYL™ molecules to 0.2-2 μM in serum-free Accell media (well) and aliquoted the INTASYL™ containing media to cells (100 μl/well of 96-well plate).

Seventy-two hours post administration, cells were lysed, and mRNA levels determined by the Quantigene branched DNA assay according to manufacturer's protocol using gene-specific probes. Data are normalized to a housekeeping gene (PPIB) and graphed with respect to the non-targeting control. Error bars represent the standard deviation from the mean of biological triplicates.

Results shown in FIG. 1 demonstrate significant silencing of BRD4-targeting INTASYL™ molecules BRD4-11, BRD4-20, BRD4-21, BRD4-22, and BRD4-23 delivered to A549 cells, obtaining greater than 60-70% inhibition of gene expression with 2 μM INTASYL™ molecules.

Example 3: Five Point Dose Response Curves of INTASYL™ Molecules Targeting BRD4 in T-Cells Primary human T-cells were obtained from AllCells (CA) and cultured in Immunocult medium containing 10% Fetal Bovine Serum (Gibco) and 1000 IU/mL IL2. Cells were activated with anti-CD3/CD28 Dynabeads (Gibco, 11131) according to the manufacturer's instructions for at least 4 days prior to the transfection. INTASYL™ molecules targeting BRD4 were prepared by separately diluting the compounds to 0.12-4 μM in serum-free RPMI per sample (well) and aliquoted at 50 μl/well of 96-well plate. Cells were prepared in Immunocult media containing 5% FBS and IL2 2000 U/ml at 1,000,000 cells/ml and seeded at 50 μl/well into the 96-well plate with pre-diluted INTASYL™ molecules.

72 hours later, the transfected cells were lysed with 50 uL of Lysis Mixture and 3 uL of Proteinase K per well. Cells were lysed for 30 min at 37 C. mRNA levels determined by Branched DNA assay according to manufacturer's protocol.

Figure 2:
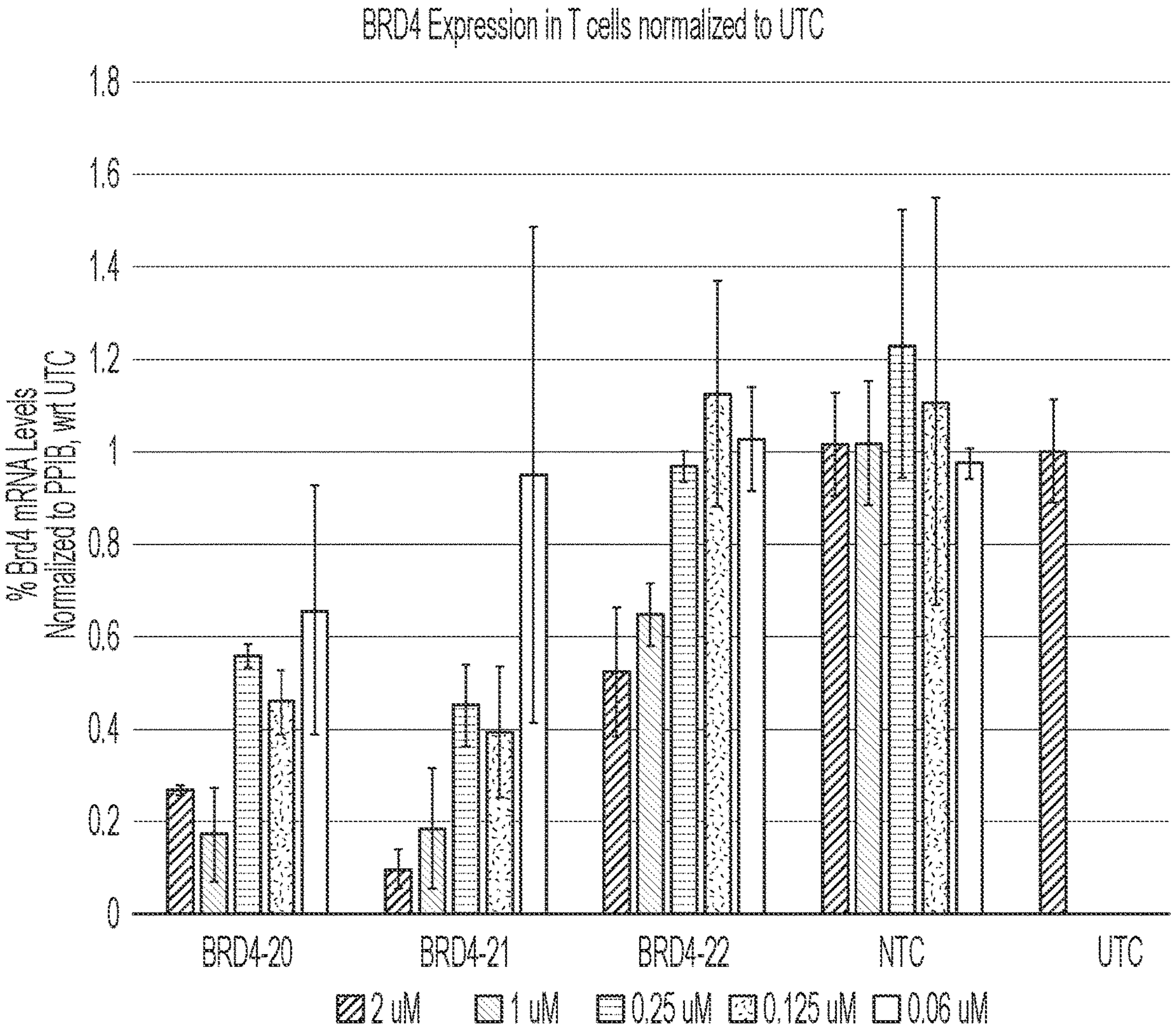
FIG. 2 shows dose response curves of chemically-modified INTASYL™ molecules targeting BRD4 in human primary T-cells. For each chemically modified INTASYL™ molecules, the concentrations tested from left to right were 2 μM, 1 μM, 0.25 μM, 0.125 μM, and 0.06 μM.

Results shown in FIG. 2 demonstrate dose-dependent silencing of BRD4-targeting INTASYL™ molecules in T-cells, with greater than 70-80% inhibition of gene expression with 2 μM with INTASYL™ molecules BRD4-20 and 21.

Figure 3:
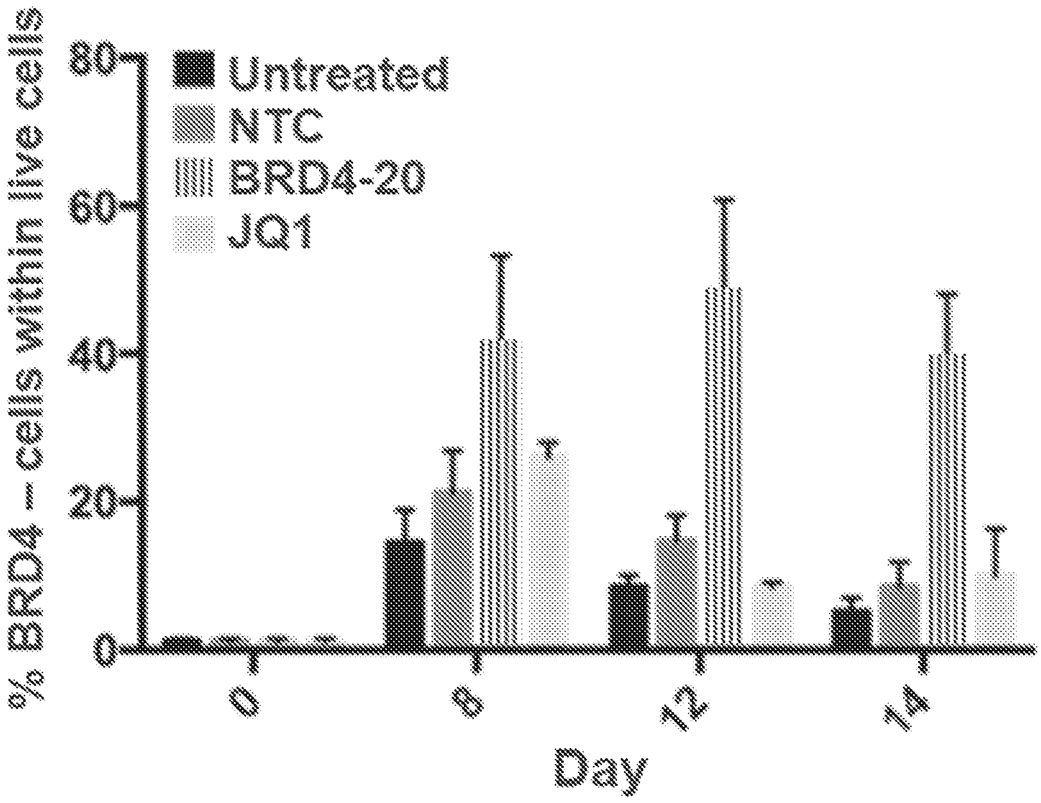
FIG. 3 shows the percentage of BRD4-negative cells after treatment with BRD4-20, a non-targeting control (NTC; a negative control), or JQ1 (a positive control), or without treatment (untreated) at different time points.
Figure 4A:
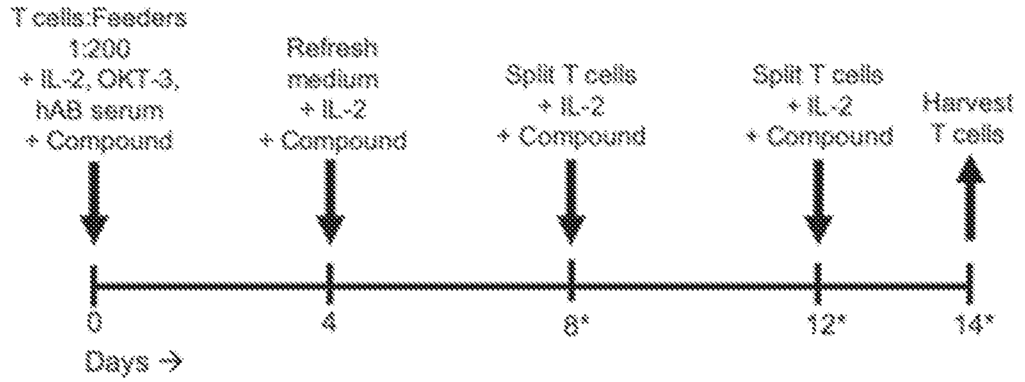
FIGS. 4A-4B show the study protocol (FIG. 4A) and the percentage of CCR7+/CD62L+ cells following no treatment (UNT, untreated), treatment with a non-targeting control (NTC), treatment with BRD4-20, and treatment with a positive control (JQ1) (FIG. 4B).
Figure 4B:
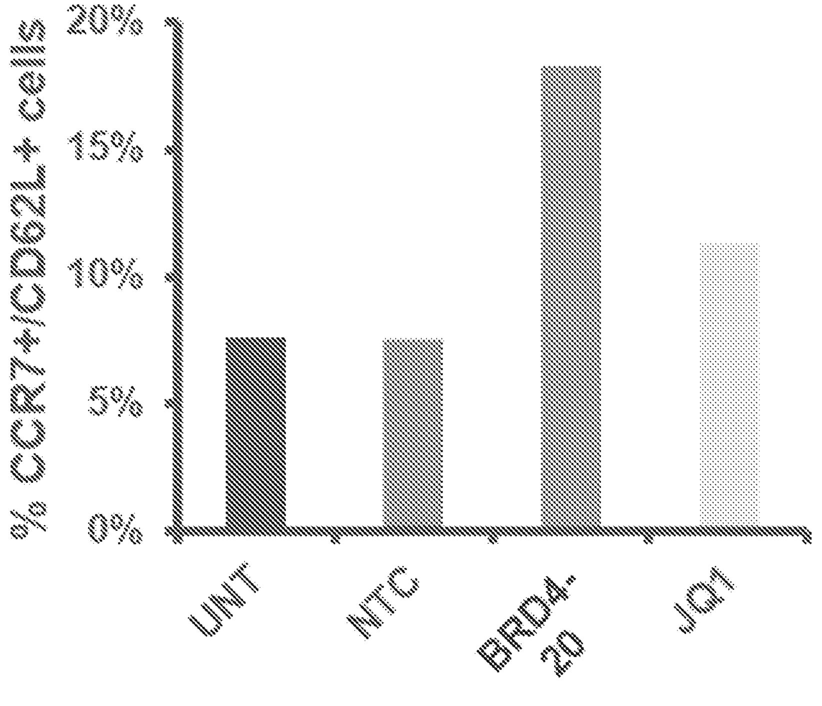

Example 4: Ex Vivo Treatment of Tumor Infiltrating Lymphocytes (TILs) with BRD-4-Targeting INTASYL™ Compounds CD8+ T cells were isolated from healthy human volunteer peripheral blood mononuclear cells (PBMCs) by negative selection. These cells were then expanded using the National Cancer Institute's rapid expansion protocol (REP). During the REP, cells were treated with either BRD4-20, non-targeting control (NTC), JQ1 (positive control) or left untreated. Compound addition is outlined in FIG. 4A. The percent of BRD4-negative cells was determined on days 0, 8, 12, and 14. At day 14 of the REP, cells were harvested and analyzed for levels of BRD4 protein as well as differentiation markers by flow-cell cytometry. Treatment of CD8+ T cells with BRD4-20 (2 μM) resulted in increased population of BRD4-negative CD8+ T cells (demonstrating BRD4 protein reduction) (FIG. 3), as well as an increase in the frequency of CD 8+ T cells with a stem-cell like memory phenotype (CCR7+/CD62L+) compared to controls (FIG. 4B).

Figure 5:
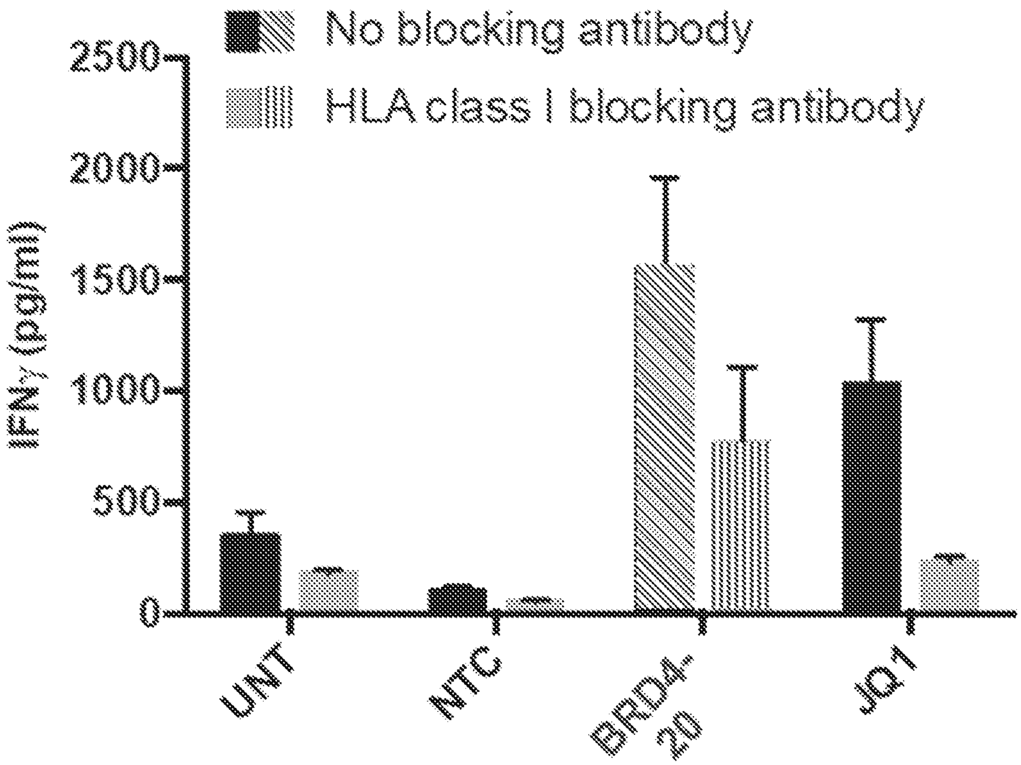
FIG. 5 shows the concentration of interferon-γ (IFN-γ) in melanoma-derived tumor-infiltrating lymphocytes (TILs) co-incubated with human melanoma following no treatment (UNT), a non-targeting control (NTC; negative control), BRD4-20, or JQ1 (a positive control).

Furthermore, a subset of CD8+ T cells treated as above were used in co-culture with A375, a malignant melanoma cell line, to determine functional recognition of tumor cells. Treatment with BRD4-20 during the REP resulted in CD8+ T cells with enhanced recognition of the tumor cells as demonstrated by increased levels of INF¥ production (FIG. 5).

Figure 6A:
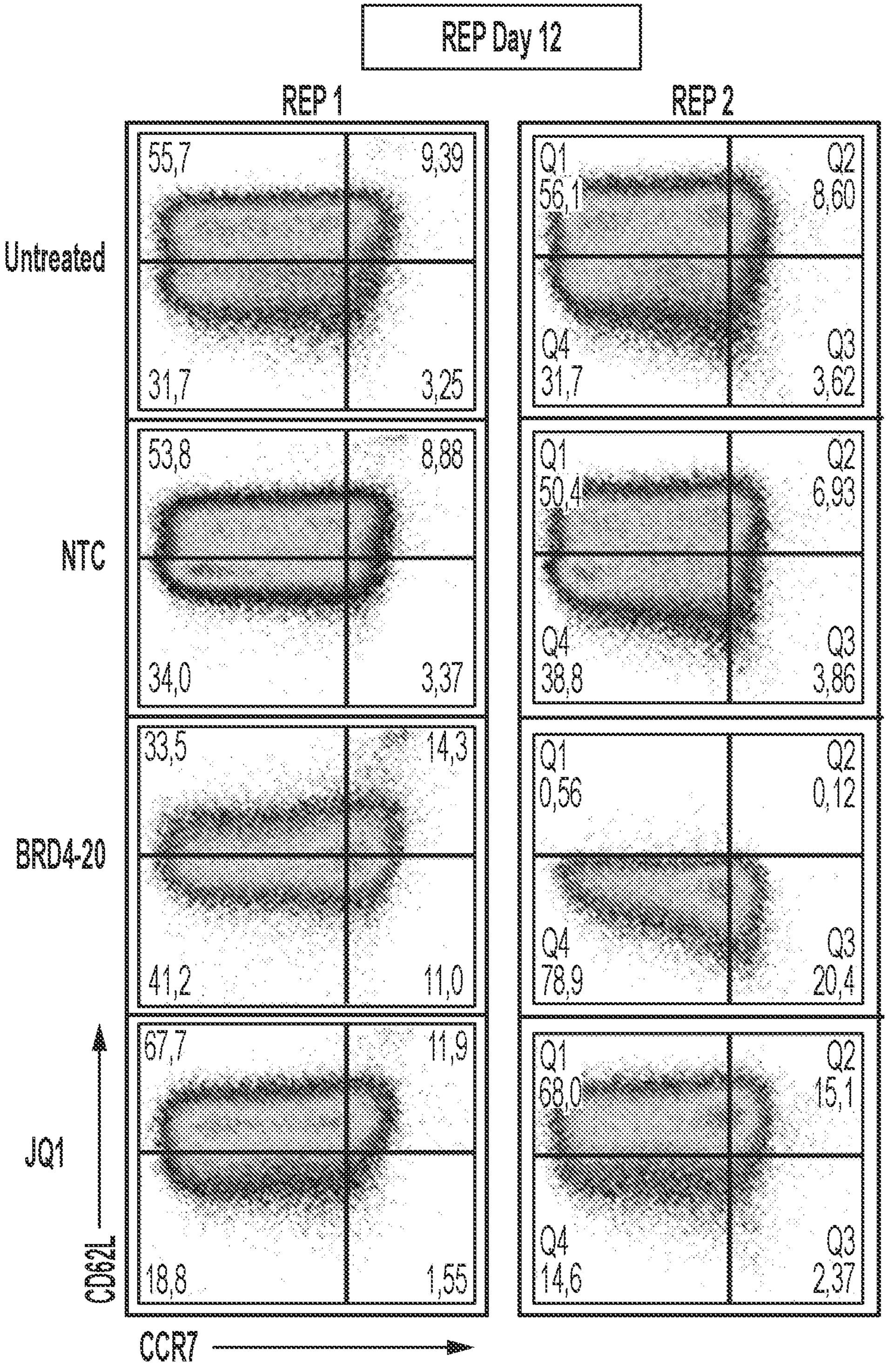
FIGS. 6A-6B show the results of a flow cytometric analysis of TILs on Day 12 of the National Cancer Institute rapid expansion protocol (REP).
Figure 6B:
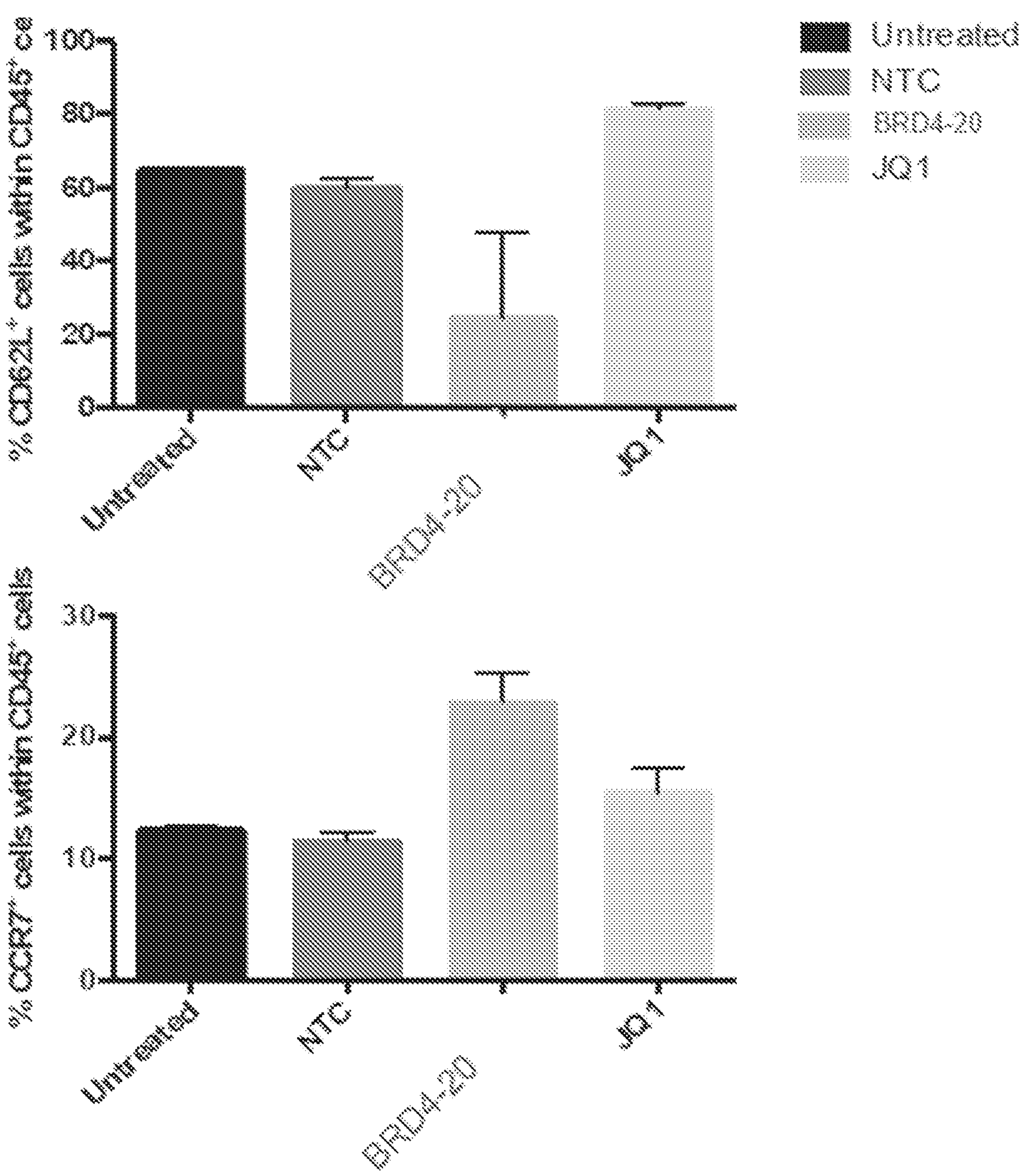

Treatment with BRD4-20 during REP was also found to result in differentiation to stem cell memory T cells ($T_{SCM}$). FIGS. 6A-6B show the results of flow cytometry on REP Day 12, indicating that the BRD4-20-treated cells had a decrease in CD45RA+CD62L+ staining, and an increase in CD45RA+CCR7+ staining in comparison to the other treatment groups.

Figure 7:
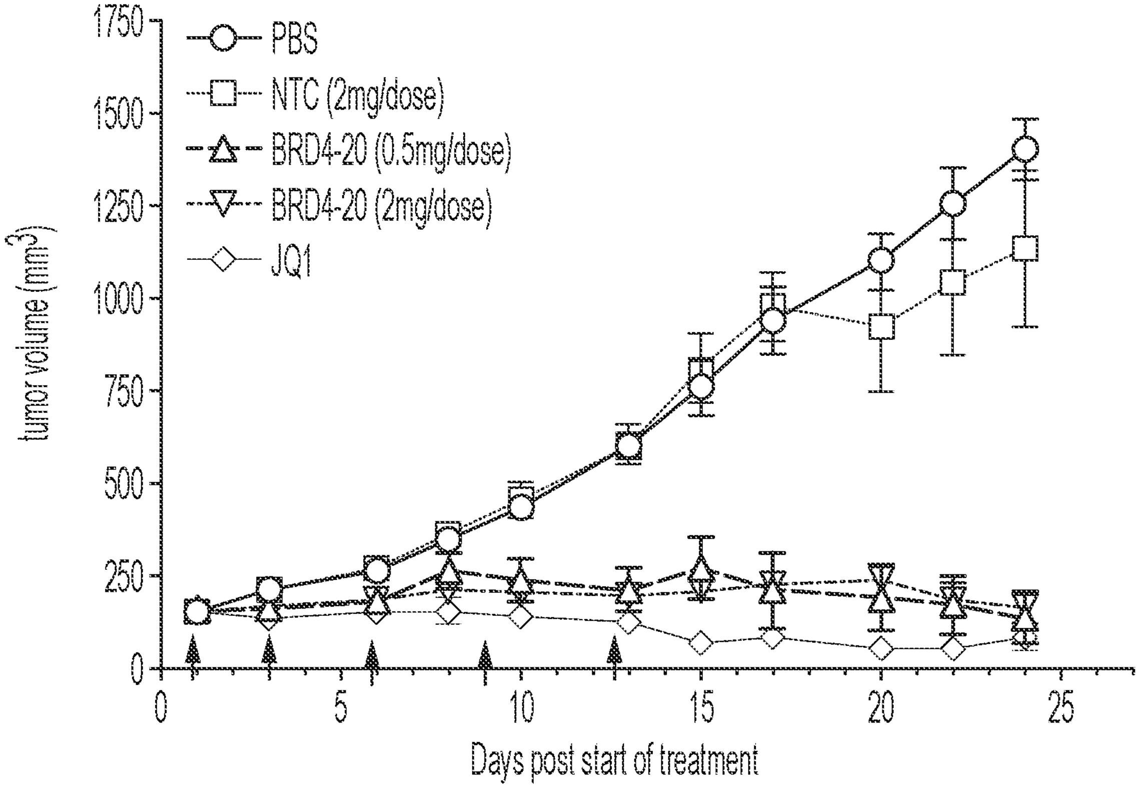
FIG. 7 shows the tumor volume in Hepa 1-6 tumor-bearing mice measured after treatment with PBS, a non-targeting control (NTC), BRD4-20 (0.5 mg/dose), BRD4-20 (2 mg/dose), or JQ1 (a positive control) over time.
Figure 8:
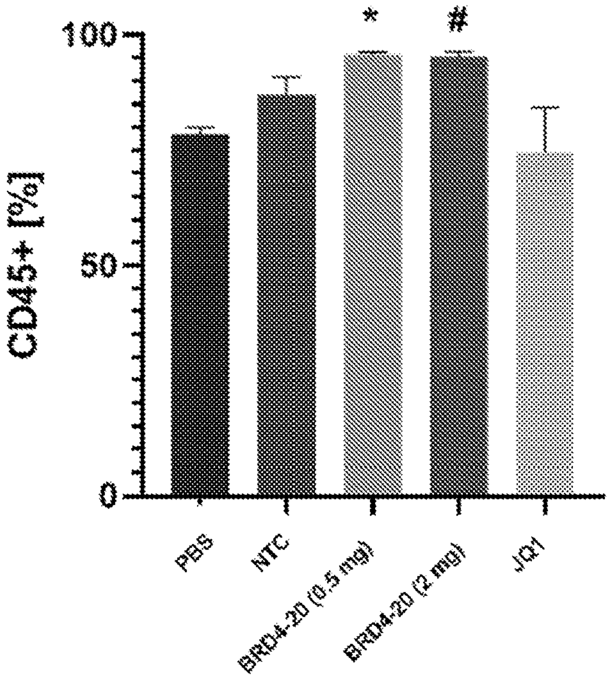
FIG. 8 shows the percentage of CD45+ TILs measured in Hepa 1-6 tumor-bearing mice following the treatment indicated in the graph.

Example 5: Multi Dose Intratumoral Injection of BRD4-20 Results in the Inhibition of Tumor Growth In Vivo Hepa 1-6 tumor-bearing mice (female C57BL/6Crl mice subcutaneously injected with murine hepatocellular carcinoma) were treated with INTASYL™ targeting BRD4 (BRD4-20) intratumorally on Days 1, 4, 7, 10, and 14 at two doses: 0.5 mg/tumor and 2 mg/tumor. JQ1, a non-specific inhibitor of bromodomain proteins, was used as a positive control. A non-targeting control (NTC) was used as a negative control. The longitudinal mean tumor volume ($mm^3$) was recorded and plotted through the duration of the study (FIG. 7). The intratumor injection of BRD4-20 was found to inhibit tumor growth at both dose levels. Mice were sacrificed on Day 14 following the last dose, and the tumors were excised. TILs were isolated and analyzed for CD45+ population by flow cytometry. As is shown in FIG. 8, treatment with BRD4-20 increased CD45+ TILs in the tumor microenvironment (TME) at both dose levels.

Example 6: Dose Response of BRD4-20 in Hepa 1-6 Tumor Bearing Mice Results in the Inhibition of Tumor Growth In Vivo Hepa 1-6 tumor bearing mice were treated with increasing dose levels of INTASYL™ targeting BRD4 (BRD4-20) administered intratumorally on Days 1, 3, 7, 10, and 14 (0.02 mg to 0.5 mg per injection). The tumor volume target for the start of dosing was 150 $mm^3$. A satellite group (n=6) was sacrificed on Day 12 for TME analysis. The study schedule is shown in Table 3.

TABLE 3

BRD4-20 Dose Titration Study Design

| Group | N | Test Article | Dose/mouse (IT 50 μl/dose) | Dosing Days |
|---|---|---|---|---|
| 1 | 12 | PBS | 50 μl | 1, 3, 7, 10, 14 |
| 2 | 12 | BRD4-20 | 0.5 mg | 1, 3, 7, 10, 14 |
| 3 | 12 | BRD4-20 | 0.25 mg | 1, 3, 7, 10, 14 |
| 4 | 12 | BRD4-20 | 0.1 mg | 1, 3, 7, 10, 14 |
| 5 | 12 | BRD4-20 | 0.02 mg | 1, 3, 7, 10, 14 |
| 6 | 12 | NTC-647 | 0.5 mg | 1, 3, 7, 10, 14 |

Figure 9A:
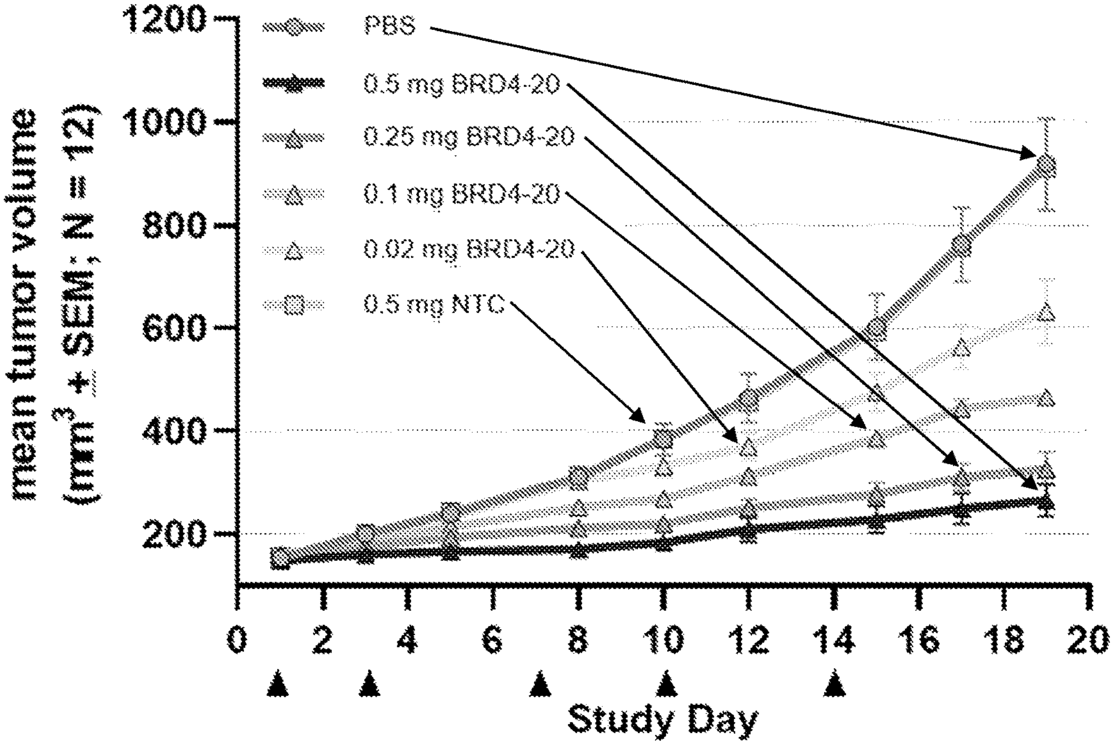
FIGS. 9A-9B show tumor volume during the study.
Figure 9B:
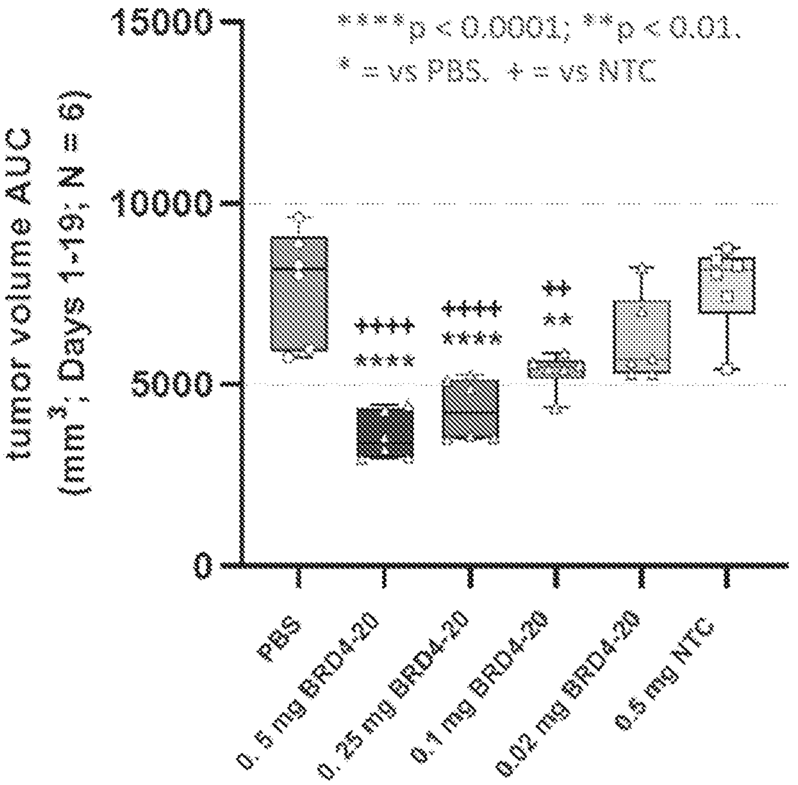

A non-targeting control (NTC) was used as a negative control. The longitudinal mean tumor volume ($mm^3$) was recorded (FIG. 9A) and tumor volume AUC (FIG. 9B) was calculated by trapezoidal transformation. Statistical significance was assessed by one way ANOVA and Tukey's multiple comparisons post-hoc tests.

Intratumoral administration of BRD4-20 resulted in a dose-dependent inhibition of tumor growth.

TABLE 1

BRD1 Target Sites (BRD1 human; NM_058243.2)

| Duplex ID | Start Site | SEQ ID | mRNA Target Site | SEQ ID | Gene Region |
|---|---|---|---|---|---|
| BRD4-1 | 577 | 1 | UACUGGAAUGCUCAGGAAUG | 25 | aaacaacuauUACUGGAAUGCUCAGGAAUGuauccaggacu |
| BRD4-2 | 581 | 2 | GGAAUGCUCAGGAAUGUAUC | 26 | aacuauuacuGGAAUGCUCAGGAAUGUAUCcaggacuucaa |
| BRD4-3 | 593 | 3 | AAUGUAUCCAGGACUUCAAC | 27 | aaugcucaggAAUGUAUCCAGGACUUCAACacuauguuuac |
| BRD4-4 | 734 | 4 | UCAUGAUAGUCCAGGCAAAA | 28 | gaaaccgagaUCAUGAUAGUCCAGGCAAAAggaagaggacg |
| BRD4-5 | 803 | 5 | CCACGGUACCAAACACAACU | 29 | ccuggcguuuCCACGGUACCAAACACAACUcaagcaucgac |
| BRD4-6 | 1303 | 6 | CUCAAGGAGAUGUUUGCCAA | 30 | cagcggcaucCUCAAGGAGAUGUUUGCCAAgaagcacgccg |
| BRD4-7 | 1306 | 7 | AAGGAGAUGUUUGCCAAGAA | 31 | cggcauccucAAGGAGAUGUUUGCCAAGAAgcacgccgccu |
| BRD4-8 | 1384 | 8 | CACGACUACUGUGACAUCAU | 32 | acugggccuaCACGACUACUGUGACAUCAUcaagcacccca |

TABLE 1-continued

| BRD1 Target Sites (BRD1 human; NM_058243.2) | | | | | |
|---|---|---|---|---|---|
| Duplex ID | Start Site | SEQ ID | mRNA Target Site | SEQ ID | Gene Region |
| BRD4-9 | 1414 | 9 | AUGGACAUGAGCACAAUCAA | 33 | caagcaccccAUGGACAUGAGCACAAUCAAgucuaaacugg |
| BRD4-10 | 1416 | 10 | GGACAUGAGCACAAUCAAGU | 34 | agcaccccauGGACAUGAGCACAAUCAAGUcuaaacuggag |
| BRD4-11 | 1487 | 11 | UCCGAUUGAUGUUCUCCAAC | 35 | ggugcugacgUCCGAUUGAUGUUCUCCAACugcuauaagua |
| BRD4-12 | 1491 | 12 | AUUGAUGUUCUCCAACUGCU | 36 | cugacguccgAUUGAUGUUCUCCAACUGCUauaaguacaac |
| BRD4-13 | 2236 | 13 | ACCUCCUGUUUGCGGAAGAA | 37 | gcgcuaugucACCUCCUGUUUGCGGAAGAAaaggaaaccuc |
| BRD4-14 | 2241 | 14 | CUGUUUGCGGAAGAAAAGGA | 38 | augucaccucCUGUUUGCGGAAGAAAAGGAaaccucaagcu |
| BRD4-15 | 550 | 15 | AUAAAGAAGCGCUUGGAAAA | 39 | uaugggaacaAUAAAGAAGCGCUUGGAAAAcaacuauuacu |
| BRD4-16 | 434 | 16 | UCAAGACACUAUGGAAACAC | 40 | agaguggugcUCAAGACACUAUGGAAACACcaguuugcaug |
| BRD4-17 | 1500 | 17 | CUCCAACUGCUAUAAGUACA | 41 | gauugauguuCUCCAACUGCUAUAAGUACAacccuccugac |
| BRD4-18 | 1388 | 18 | ACUACUGUGACAUCAUCAAG | 42 | ggccuacacgACUACUGUGACAUCAUCAAGcaccccaugga |
| BRD4-19 | 1574 | 19 | AAAUGCGCUUUGCCAAGAUG | 43 | gauguguucgAAAUGCGCUUUGCCAAGAUGccggacgagcc |
| BRD4-20 | 1559 | 20 | UCCAGGAUGUGUUCGAAAUG | 44 | gcccgcaagcUCCAGGAUGUGUUCGAAAUGcgcuuugccaa |
| BRD4-21 | 1930 | 21 | CCUAAAAAGACGAAGAAAAA | 45 | ggaaccuccuCCUAAAAAGACGAAGAAAAAuaauagcagca |
| BRD4-22 | 2273 | 22 | AGAAAGUUGAUGUGAUUGCC | 46 | ccucaagcugAGAAAGUUGAUGUGAUUGCCggcuccuccaa |
| BRD4-23 | 2177 | 23 | UUGAAAUCGACUUUGAGACC | 47 | cccgacgagaUUGAAAUCGACUUUGAGACCcugaagccguc |
| BRD4-24 | 2358 | 24 | UGACAGCGAAGACUCCGAAA | 48 | ccagcuccucUGACAGCGAAGACUCCGAAAcagagauggcu |

TABLE 2

| BRD4 INTASYL ™ Sequences (passenger/sense strand; guide/antisense strand) | | | |
|---|---|---|---|
| Duplex ID | Start Site | Sequence | SEQ ID NO: |
| BRD4-1 | 577 | fG.mA.fA.mU.fG.mC.fU.mC.fA.mG.fG.mA.fA*mU*fA.TEG-Chl | 49 |
| | | P.mU.fA.mU.fU.mC.fC.mU.fG.mA.fG.mC.fA.mU.fU*mC*fC*mA*fG*mU*fA | 50 |
| BRD4-2 | 581 | fG.mC.fU.mC.fA.mG.fG.mA.fA.mU.fG.mU.fA*mU*fA.TEG-Chl | 51 |
| | | P.mU.fA.mU.fA.mC.fA.mU.fU.mC.fC.mU.fG.mA.fG*mC*fA*mU*fU*mC*fC | 52 |
| BRD4-3 | 593 | fA.mU.fC.mC.fA.mG.fG.mA.fC.mU.fU.mC.fA*mA*fA.TEG-Chl | 53 |
| | | P.mU.fU.mU.fG.mA.fA.mG.fU.mC.fC.mU.fG.mG.fA*mU*fA*mC*fA*mU*fU | 54 |
| BRD4-4 | 734 | fA.mU.fA.mG.fU.mC.fC.mA.fG.mG.fC.mA.fA*mA*fA.TEG-Chl | 55 |
| | | P.mU.fU.mU.fU.mG.fC.mC.fU.mG.fG.mA.fC.mU.fA*mU*fC*mA*fU*mG*fA | 56 |
| BRD4-5 | 803 | fG.mU.fA.mC.fC.mA.fA.mA.fC.mA.fC.mA.fA*mC*fA.TEG-Chl | 57 |
| | | P.mU.fG.mU.fU.mG.fU.mG.fU.mU.fU.mG.fG.mU.fA*mC*fC*mG*fU*mG*fG | 58 |

TABLE 2-continued

| BRD4 INTASYL ™ Sequences (passenger/sense strand; guide/antisense strand) | | | |
|---|---|---|---|
| Duplex ID | Start Site | Sequence | SEQ ID NO: |
| BRD4-6 | 1303 | fG.mG.fA.mG.fA.mU.fG.mU.fU.mU.fG.mC.fC*mA*fA.TEG-Chl | 59 |
| | | P.mU.fU.mG.fG.mC.fA.mA.fA.mC.fA.mU.fC.mU.fC*mC*fU*mU*fG*mA*fG | 60 |
| BRD4-7 | 1306 | fG.mA.fU.mG.fU.mU.fU.mG.fC.mC.fA.mA.fG*mA*fA.TEG-Chl | 61 |
| | | P.mU.fU.mC.fU.mU.fG.mG.fC.mA.fA.mA.fC.mA.fU*mC*fU*mC*fC*mU*fU | 62 |
| BRD4-8 | 1384 | fC.mU.fA.mC.fU.mG.fU.mG.fA.mC.fA.mU.fC*mA*fA.TEG-Chl | 63 |
| | | P.mU.fU.mG.fA.mU.fG.mU.fC.mA.fC.mA.fG.mU.fA*mG*fU*mC*fG*mU*fG | 64 |
| BRD4-9 | 1414 | fC.mA.fU.mG.fA.mG.fC.mA.fC.mA.fA.mU.fC*mA*fA.TEG-Chl | 65 |
| | | P.mU.fU.mG.fA.mU.fU.mG.fU.mG.fC.mU.fC.mA.fU*mG*fU*mC*fC*mA*fU | 66 |
| BRD4-10 | 1416 | fU.mG.fA.mG.fC.mA.fC.mA.fA.mU.fC.mA.fA*mG*fA.TEG-Chl | 67 |
| | | P.mU.fC.mU.fU.mG.fA.mU.fU.mG.fU.mG.fC.mU.fC*mA*fU*mG*fU*mC*fC. | 68 |
| BRD4-11 | 1487 | fU.mU.fG.mA.fU.mG.fU.mU.fC.mU.fC.mC.fA*mA*fA.TEG-Chl | 69 |
| | | P.mU.fU.mU.fG.mG.fA.mG.fA.mA.fC.mA.fU.mC.fA*mA*fU*mC*fG*mG*fA | 70 |
| BRD4-12 | 1491 | fU.mG.fU.mU.fC.mU.fC.mC.fA.mA.fC.mU.fG*mC*fA.TEG-Chl | 71 |
| | | P.mU.fG.mC.fA.mG.fU.mU.fG.mG.fA.mG.fA.mA.fC*mA*fU*mC*fA*mA*fU | 72 |
| BRD4-13 | 2236 | fC.mU.fG.mU.fU.mU.fG.mC.fG.mG.fA.mA.fG*mA*fA.TEG-Chl | 73 |
| | | P.mU.fU.mC.fU.mU.fC.mC.fG.mC.fA.mA.fA.mC.fA*mG*fG*mA*fG*mG*fU | 74 |
| BRD4-14 | 2241 | fU.mG.fC.mG.fG.mA.fA.mG.fA.mA.fA.mA.fG*mG*fA.TEG-Chl | 75 |
| | | P.mU.fC.mC.fU.mU.fU.mU.fC.mU.fU.mC.fC.mG.fC*mA*fA*mA*fC*mA*fG | 76 |
| BRD4-15 | 550 | fG.mA.fA.mG.fC.mG.fC.mU.fU.mG.fG.mA.fA*mA*fA.TEG-Chl | 77 |
| | | P.mU.fU.mU.fU.mC.fC.mA.fA.mG.fC.mG.fC.mU.fU*mC*fU*mU*fU*mA*fU | 78 |
| BRD4-16 | 434 | fA.mC.fA.mC.fU.mA.fU.mG.fG.mA.fA.mA.fC*mA*fA.TEG-Chl | 79 |
| | | P.mU.fU.mG.fU.mU.fU.mC.fC.mA.fU.mA.fG.mU.fG*mU*fC*mU*fU*mG*fA | 80 |
| BRD4-17 | 1500 | fA.mC.fU.mG.fC.mU.fA.mU.fA.mA.fG.mU.fA*mC*fA.TEG-Chl | 81 |
| | | P.mU.fG.mU.fA.mC.fU.mU.fA.mU.fA.mG.fC.mA.fG*mU*fU*mG*fG*mA*fG | 82 |
| BRD4-18 | 1388 | fU.mG.fU.mG.fA.mC.fA.mU.fC.mA.fU.mC.fA*mA*fA.TEG-Chl | 83 |
| | | P.mU.fU.mU.fG.mA.fU.mG.fA.mU.fG.mU.fC.mA.fC*mA*fG*mU*fA*mG*fU | 84 |
| BRD4-19 | 1574 | fC.mG.fC.mU.fU.mU.fG.mC.fC.mA.fA.mG.fA*mU*fA.TEG-Chl | 85 |
| | | P.mU.fA.mU.fC.mU.fU.mG.fG.mC.fA.mA.fA.mG.fC*mG*fC*mA*fU*mU*fU | 86 |
| BRD4-20 | 1559 | fG.mA.fU.mG.fU.mG.fU.mU.fC.mG.fA.mA.fA*mU*fA.TEG-Chl | 87 |
| | | P.mU.fA.mU.fU.mU.fC.mG.fA.mA.fC.mA.fC.mA.fU*mC*fC*mU*fG*mG*fA | 88 |
| BRD4-21 | 1930 | fA.mA.fA.mG.fA.mC.fG.mA.fA.mG.fA.mA.fA*mA*fA.TEG-Chl | 89 |
| | | P.mU.fU.mU.fU.mU.fC.mU.fU.mC.fG.mU.fC.mU.fU*mU*fU*mU*fA*mG*fG | 90 |
| BRD4-22 | 2273 | fG.mU.fU.mG.fA.mU.fG.mU.fG.mA.fU.mU.fG*mC*fA.TEG-Chl | 91 |
| | | P.mU.fG.mC.fA.mA.fU.mC.fA.mC.fA.mU.fC.mA.fA*mC*fU*mU*fU*mC*fU | 92 |
| BRD4-23 | 2177 | fA.mU.fC.mG.fA.mC.fU.mU.fU.mG.fA.mG.fA*mC*fA.TEG-Chl | 93 |
| | | P.mU.fG.mU.fC.mU.fC.mA.fA.mA.fG.mU.fC.mG.fA*mU*fU*mU*fC*mA*fA | 94 |
| BRD4-24 | 2358 | fG.mC.fG.mA.fA.mG.fA.mC.fU.mC.fC.mG.fA*mA*fA.TEG-Chl | 95 |
| | | P.mU.fU.mU.fC.mG.fG.mA.fG.mU.fC.mU.fU.mC.fG*mC*fU*mG*fU*mC*fA | 96 |

Key
A = adenosine
G = guanosine
U = uridine
C = cytodine
m = 2'-O-methyl nucleotide
f = 2'fluoro nucleotide
Y = 5 methyl uridine
X = 5 methyl cytodine
* = phosphorothioate linkage
. = phosphodiester linkage
TEG-Chl = cholesterol-TEG-Glyceryl
P = 5' inorganic Phosphate
VP - 5'Vinyl Phosphonate
S - 5' Thiophosphate

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. An isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications, wherein the isolated asymmetric double stranded nucleic acid molecule is directed against a gene encoding BRD4, and wherein the sequence of the isolated asymmetric double stranded nucleic acid molecule comprises at least 12 contiguous nucleotides of:

SEQ ID NO: 87 (fG.mA.fU.mG.fU.mG.fU.mU.fC.mG.fA.mA.fA*mU*fA.TEG-Chl) and/or

SEQ ID NO: 88 (P.mU.fA.mU.fU.mU.fC.mG.fA.mA.fC.mA.fC.mA.fU*mC*fC*mU*fG*mG*fA).

2. A composition comprising the isolated asymmetric double stranded nucleic acid molecule of claim 1 and a pharmaceutically acceptable excipient.

3. The composition of claim 2, wherein the isolated asymmetric double stranded nucleic acid molecule comprises or consists of the sequence set forth in BRD4-20 (SEQ ID NOs: 87 and 88).

4. The composition of claim 2, wherein the isolated asymmetric double stranded nucleic acid molecule comprises:

a sense strand having the sequence set forth in SEQ ID NO: 87 and/or an antisense strand having the sequence set forth in SEQ ID NO: 88.

5. An immunomodulatory composition comprising a host cell which was treated ex vivo with a chemically-modified double stranded nucleic acid molecule that is directed against a gene encoding BRD4 to control and/or reduce the level of differentiation of the host cell to enable the production of a specific immune cellular population for administration in a human, wherein the sequence of the chemically-modified double stranded nucleic acid molecule comprises at least 12 contiguous nucleotides of:

SEQ ID NO: 87 (fG.mA.fU.mG.fU.mG.fU.mU.fC.mG.fA.mA.fA*mU*fA.TEG-Chl) and/or

SEQ ID NO: 88 (P.mU.fA.mU.fU.mU.fC.mG.fA.mA.fC.mA.fC.mA.fU*mC*fC*mU*fG*mG*fA).

6. The immunomodulatory composition of claim 5, wherein the chemically-modified double stranded nucleic acid molecule directed against a gene encoding BRD4 is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modification.

7. The immunomodulatory composition of claim 5, wherein the host cell is selected from the group of: T-cell, Tumor infiltrating lymphocytes (TILs), NK-cell, antigen-presenting cell (APC), dendritic cell (DC), stem cell (SC), induced pluripotent stem cell (iPSC), stem cell memory T-cell, tumor cell, Cytokine-induced Killer cell (CIK), and macrophage.

8. The immunomodulatory composition of claim 7, wherein the host cell is a T-cell, and the T-cell is a CD8+ T-cell.

9. The immunommodulatory composition of claim 8, wherein the T-cell is differentiated into a TSCM or TCM after introduction of the chemically-modified double stranded nucleic acid molecule.

10. The immunommodulatory composition of claim 9, wherein the immunomodulatory composition comprises at least 50%, at least 60%, at least 70%, at least 80%, at least 90%, at least 95%, at least 99% or 100% TSCM or TCM cells.

11. The immunomodulatory composition of claim 7, wherein the T-cell comprises one or more transgenes expressing a high affinity T-cell receptor (TCR) and/or a chimeric antigen receptor (CAR).

12. A method for producing an immunomodulatory composition, the method comprising introducing into a cell the isolated asymmetric double stranded nucleic acid molecule of claim 1.

13. The method of claim 12, wherein the cell is derived from a healthy donor or a subject having or suspected of having a proliferative disease.

14. A method for treating a subject suffering from a proliferative disease or infectious disease, the method comprising administering to the subject the immunomodulatory composition of claim 5.

15. The method of claim 14, wherein the immunomodulatory composition is for administration via adoptive cell transfer.

16. A method for treating a subject suffering from a proliferative disease or infectious disease, the method comprising administering to the subject the isolated asymmetric double stranded nucleic acid molecule of claim 1.

* * * * *

SEQUENCE LISTING

```
<160> NUMBER OF SEQ ID NOS: 96

<210> SEQ ID NO 1
<211> LENGTH: 20
<212> TYPE: RNA
<213> ORGANISM: Homo Sapiens

<400> SEQUENCE: 1

uacuggaaug cucaggaaug                                                20


<210> SEQ ID NO 2
<211> LENGTH: 20
<212> TYPE: RNA
<213> ORGANISM: Homo Sapiens

<400> SEQUENCE: 2

ggaaugcuca ggaauguauc                                                20


<210> SEQ ID NO 3
<211> LENGTH: 20
<212> TYPE: RNA
<213> ORGANISM: Homo Sapiens

<400> SEQUENCE: 3

aauguaucca ggacuucaac                                                20


<210> SEQ ID NO 4
<211> LENGTH: 20
<212> TYPE: RNA
<213> ORGANISM: Homo Sapiens

<400> SEQUENCE: 4

ucaugauagu ccaggcaaaa                                                20


<210> SEQ ID NO 5
<211> LENGTH: 20
<212> TYPE: RNA
<213> ORGANISM: Homo Sapiens

<400> SEQUENCE: 5

ccacgguacc aaacacaacu                                                20


<210> SEQ ID NO 6
<211> LENGTH: 20
<212> TYPE: RNA
<213> ORGANISM: Homo Sapiens

<400> SEQUENCE: 6

cucaaggaga uguuugccaa                                                20


<210> SEQ ID NO 7
<211> LENGTH: 20
<212> TYPE: RNA
<213> ORGANISM: Homo Sapiens

<400> SEQUENCE: 7

aaggagaugu uugccaagaa                                                20
```

```
<210> SEQ ID NO 8
<211> LENGTH: 20
<212> TYPE: RNA
<213> ORGANISM: Homo Sapiens

<400> SEQUENCE: 8

cacgacuacu gugacaucau                                                    20


<210> SEQ ID NO 9
<211> LENGTH: 20
<212> TYPE: RNA
<213> ORGANISM: Homo Sapiens

<400> SEQUENCE: 9

auggacauga gcacaaucaa                                                    20


<210> SEQ ID NO 10
<211> LENGTH: 20
<212> TYPE: RNA
<213> ORGANISM: Homo Sapiens

<400> SEQUENCE: 10

ggacaugagc acaaucaagu                                                    20


<210> SEQ ID NO 11
<211> LENGTH: 20
<212> TYPE: RNA
<213> ORGANISM: Homo Sapiens

<400> SEQUENCE: 11

uccgauugau guucuccaac                                                    20


<210> SEQ ID NO 12
<211> LENGTH: 20
<212> TYPE: RNA
<213> ORGANISM: Homo Sapiens

<400> SEQUENCE: 12

auugauguuc uccaacugcu                                                    20


<210> SEQ ID NO 13
<211> LENGTH: 20
<212> TYPE: RNA
<213> ORGANISM: Homo Sapiens

<400> SEQUENCE: 13

accuccuguu ugcggaagaa                                                    20


<210> SEQ ID NO 14
<211> LENGTH: 20
<212> TYPE: RNA
<213> ORGANISM: Homo Sapiens

<400> SEQUENCE: 14

cuguuugcgg aagaaaagga                                                    20


<210> SEQ ID NO 15
<211> LENGTH: 20
<212> TYPE: RNA
<213> ORGANISM: Homo Sapiens

<400> SEQUENCE: 15

auaaagaagc gcuuggaaaa                                                    20
```

<210> SEQ ID NO 16
<211> LENGTH: 20
<212> TYPE: RNA
<213> ORGANISM: Homo Sapiens

<400> SEQUENCE: 16
ucaagacacu auggaaacac 20

<210> SEQ ID NO 17
<211> LENGTH: 20
<212> TYPE: RNA
<213> ORGANISM: Homo Sapiens

<400> SEQUENCE: 17
cuccaacugc uauaaguaca 20

<210> SEQ ID NO 18
<211> LENGTH: 20
<212> TYPE: RNA
<213> ORGANISM: Homo Sapiens

<400> SEQUENCE: 18
acuacuguga caucaucaag 20

<210> SEQ ID NO 19
<211> LENGTH: 20
<212> TYPE: RNA
<213> ORGANISM: Homo Sapiens

<400> SEQUENCE: 19
aaaugcgcuu ugccaagaug 20

<210> SEQ ID NO 20
<211> LENGTH: 20
<212> TYPE: RNA
<213> ORGANISM: Homo Sapiens

<400> SEQUENCE: 20
uccaggaugu guucgaaaug 20

<210> SEQ ID NO 21
<211> LENGTH: 20
<212> TYPE: RNA
<213> ORGANISM: Homo Sapiens

<400> SEQUENCE: 21
ccuaaaaaga cgaagaaaaa 20

<210> SEQ ID NO 22
<211> LENGTH: 20
<212> TYPE: RNA
<213> ORGANISM: Homo Sapiens

<400> SEQUENCE: 22
agaaaguuga ugugauugcc 20

<210> SEQ ID NO 23
<211> LENGTH: 20
<212> TYPE: RNA
<213> ORGANISM: Homo Sapiens

<400> SEQUENCE: 23
uugaaaucga cuuugagacc 20

<210> SEQ ID NO 24
<211> LENGTH: 20
<212> TYPE: RNA
<213> ORGANISM: Homo Sapiens

<400> SEQUENCE: 24
ugacagcgaa gacuccgaaa 20

<210> SEQ ID NO 25
<211> LENGTH: 41
<212> TYPE: RNA
<213> ORGANISM: Homo Sapiens

<400> SEQUENCE: 25
aaacaacuau uacuggaaug cucaggaaug uauccaggac u 41

<210> SEQ ID NO 26
<211> LENGTH: 41
<212> TYPE: RNA
<213> ORGANISM: Homo Sapiens

<400> SEQUENCE: 26
aacuauuacu ggaaugcuca ggaauguauc caggacuuca a 41

<210> SEQ ID NO 27
<211> LENGTH: 41
<212> TYPE: RNA
<213> ORGANISM: Homo Sapiens

<400> SEQUENCE: 27
aaugcucagg aauguaucca ggacuucaac acuauguuua c 41

<210> SEQ ID NO 28
<211> LENGTH: 41
<212> TYPE: RNA
<213> ORGANISM: Homo Sapiens

<400> SEQUENCE: 28
gaaaccgaga ucaugauagu ccaggcaaaa ggaagaggac g 41

<210> SEQ ID NO 29
<211> LENGTH: 41
<212> TYPE: RNA
<213> ORGANISM: Homo Sapiens

<400> SEQUENCE: 29
ccuggcguuu ccacgguacc aaacacaacu caagcaucga c 41

<210> SEQ ID NO 30
<211> LENGTH: 41
<212> TYPE: RNA
<213> ORGANISM: Homo Sapiens

<400> SEQUENCE: 30
cagcggcauc cucaaggaga uguuugccaa gaagcacgcc g 41

<210> SEQ ID NO 31
<211> LENGTH: 41
<212> TYPE: RNA
<213> ORGANISM: Homo Sapiens

<400> SEQUENCE: 31
cggcauccuc aaggagaugu uugccaagaa gcacgccgcc u 41

<210> SEQ ID NO 32
<211> LENGTH: 41
<212> TYPE: RNA
<213> ORGANISM: Homo Sapiens

<400> SEQUENCE: 32
acugggccua cacgacuacu gugacaucau caagcacccc a 41

<210> SEQ ID NO 33
<211> LENGTH: 41
<212> TYPE: RNA
<213> ORGANISM: Homo Sapiens

<400> SEQUENCE: 33
caagcacccc auggacauga gcacaaucaa gucuaaacug g 41

<210> SEQ ID NO 34
<211> LENGTH: 41
<212> TYPE: RNA
<213> ORGANISM: Homo Sapiens

<400> SEQUENCE: 34
agcaccccau ggacaugagc acaaucaagu cuaaacugga g 41

<210> SEQ ID NO 35
<211> LENGTH: 41
<212> TYPE: RNA
<213> ORGANISM: Homo Sapiens

<400> SEQUENCE: 35
ggugcugacg uccgauugau guucuccaac ugcuauaagu a 41

<210> SEQ ID NO 36
<211> LENGTH: 41
<212> TYPE: RNA
<213> ORGANISM: Homo Sapiens

<400> SEQUENCE: 36
cugacguccg auugauguuc uccaacugcu auaaguacaa c 41

<210> SEQ ID NO 37
<211> LENGTH: 41
<212> TYPE: RNA
<213> ORGANISM: Homo Sapiens

<400> SEQUENCE: 37
gcgcuauguc accuccuguu ugcggaagaa aaggaaaccu c 41

<210> SEQ ID NO 38
<211> LENGTH: 41
<212> TYPE: RNA
<213> ORGANISM: Homo Sapiens

<400> SEQUENCE: 38
augucaccuc cuguuugcgg aagaaaagga aaccucaagc u 41

<210> SEQ ID NO 39
<211> LENGTH: 41
<212> TYPE: RNA
<213> ORGANISM: Homo Sapiens

<400> SEQUENCE: 39
uaugggaaca auaaagaagc gcuuggaaaa caacuauuac u 41

<210> SEQ ID NO 40
<211> LENGTH: 41
<212> TYPE: RNA
<213> ORGANISM: Homo Sapiens

<400> SEQUENCE: 40
agaguggugc ucaagacacu auggaaacac caguuugcau g 41

<210> SEQ ID NO 41
<211> LENGTH: 41
<212> TYPE: RNA
<213> ORGANISM: Homo Sapiens

<400> SEQUENCE: 41
gauugauguu cuccaacugc uauaaguaca acccuccuga c 41

<210> SEQ ID NO 42
<211> LENGTH: 41
<212> TYPE: RNA
<213> ORGANISM: Homo Sapiens

<400> SEQUENCE: 42
ggccuacacg acuacuguga caucaucaag caccccaugg a 41

<210> SEQ ID NO 43
<211> LENGTH: 41
<212> TYPE: RNA
<213> ORGANISM: Homo Sapiens

<400> SEQUENCE: 43
gauguguucg aaaugcgcuu ugccaagaug ccggacgagc c 41

<210> SEQ ID NO 44
<211> LENGTH: 41
<212> TYPE: RNA
<213> ORGANISM: Homo Sapiens

<400> SEQUENCE: 44
gcccgcaagc uccaggaugu guucgaaaug cgcuuugcca a 41

<210> SEQ ID NO 45
<211> LENGTH: 41
<212> TYPE: RNA
<213> ORGANISM: Homo Sapiens

<400> SEQUENCE: 45
ggaaccuccu ccuaaaaaga cgaagaaaaa uaauagcagc a 41

<210> SEQ ID NO 46
<211> LENGTH: 41
<212> TYPE: RNA
<213> ORGANISM: Homo Sapiens

<400> SEQUENCE: 46
ccucaagcug agaaaguuga ugugauugcc ggcuccucca a 41

<210> SEQ ID NO 47
<211> LENGTH: 41
<212> TYPE: RNA
<213> ORGANISM: Homo Sapiens

<400> SEQUENCE: 47
cccgacgaga uugaaaucga cuuugagacc cugaagccgu c 41

<210> SEQ ID NO 48
<211> LENGTH: 41
<212> TYPE: RNA
<213> ORGANISM: Homo Sapiens

<400> SEQUENCE: 48
ccagcuccuc ugacagcgaa gacuccgaaa cagagauggc u 41

<210> SEQ ID NO 49
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:

<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 49
gaaugcucag gaaua 15

<210> SEQ ID NO 50
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 50
uauuccugag cauuccagua 20

<210> SEQ ID NO 51
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)

<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 51
gcucaggaau guaua 15

<210> SEQ ID NO 52
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 52
uauacauucc ugagcauucc 20

<210> SEQ ID NO 53
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:

-continued

<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 53
auccaggacu ucaaa 15

<210> SEQ ID NO 54
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 54

-continued uuugaagucc uggauacauu 20

<210> SEQ ID NO 55
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 55
auaguccagg caaaa 15

<210> SEQ ID NO 56
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:

<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 56
uuuugccugg acuaucauga 20

<210> SEQ ID NO 57
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 57
guaccaaaca caaca 15

<210> SEQ ID NO 58
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)

<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 58
uguuguguuu gguaccgugg 20

<210> SEQ ID NO 59
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 59
ggagauguuu gccaa 15

<210> SEQ ID NO 60
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:

<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 60
uuggcaaaca ucuccuugag 20

<210> SEQ ID NO 61
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 61
gauguuugcc aagaa 15

<210> SEQ ID NO 62
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 62
uucuuggcaa acaucuccuu 20

<210> SEQ ID NO 63
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:

-continued

<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 63
cuacugugac aucaa 15

<210> SEQ ID NO 64
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages -continued
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 64
uugaugucac aguagucgug 20

<210> SEQ ID NO 65
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)

<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 65
caugagcaca aucaa 15

<210> SEQ ID NO 66
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 66
uugauugugc ucauguccau 20

<210> SEQ ID NO 67
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:

<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 67
ugagcacaau caaga 15

<210> SEQ ID NO 68
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide -continued
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 68
ucuugauugu gcucaugucc 20

<210> SEQ ID NO 69

-continued

<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 69
uugauguucu ccaaa 15

<210> SEQ ID NO 70
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:

<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 70
uuuggagaac aucaaucgga 20

<210> SEQ ID NO 71
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 71
uguucuccaa cugca 15

<210> SEQ ID NO 72
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)

<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 72
ugcaguugga gaacaucaau 20

<210> SEQ ID NO 73
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 73
cuguuugcgg aagaa 15

<210> SEQ ID NO 74
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:

<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 74
uucuuccgca aacaggaggu 20

<210> SEQ ID NO 75
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 75
ugcggaagaa aagga 15

<210> SEQ ID NO 76
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)

```
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
```

<222> LOCATION: (20)..(20)
<223> OTHER INFORMATION: 2' fluoro nucleotide

<400> SEQUENCE: 76
uccuuuucuu ccgcaaacag 20

<210> SEQ ID NO 77
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:

-continued

<221> NAME/KEY: misc_feature
<222> LOCATION: (15)..(15)
<223> OTHER INFORMATION: may be modified by cholesterol-TEG-Glyceryl

<400> SEQUENCE: 77
gaagcgcuug gaaaa 15

<210> SEQ ID NO 78
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 78
uuuuccaagc gcuucuuuau 20

<210> SEQ ID NO 79
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)

<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 79
acacuaugga aacaa 15

<210> SEQ ID NO 80
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 80
uuguuuccau agugucuuga 20

<210> SEQ ID NO 81
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:

<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 81
acugcuauaa guaca 15

<210> SEQ ID NO 82
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 82
uguacuuaua gcaguuggag 20

<210> SEQ ID NO 83
<211> LENGTH: 15
<212> TYPE: RNA
<213> ORGANISM: Artificial Sequence
<220> FEATURE:

<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 83
ugugacauca ucaaa 15

<210> SEQ ID NO 84
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:

<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 84
uuugaugaug ucacaguagu 20

<210> SEQ ID NO 85
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 85
cgcuuugcca agaua 15

<210> SEQ ID NO 86
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)

<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 86
uaucuuggca aagcgcauuu 20

<210> SEQ ID NO 87
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base -continued
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 87
gauguguucg aaaua 15

<210> SEQ ID NO 88
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:

<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 88
uauuucgaac acauccugga 20

<210> SEQ ID NO 89
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 89
aaagacgaag aaaaa 15

<210> SEQ ID NO 90
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)

<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 90
uuuuucuucg ucuuuuuagg 20

<210> SEQ ID NO 91
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 91
guugauguga uugca 15

<210> SEQ ID NO 92
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide -continued
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 92
ugcaaucaca ucaacuuucu 20

<210> SEQ ID NO 93
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)

<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 93
aucgacuuug agaca 15

<210> SEQ ID NO 94
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 94
ugucucaaag ucgauuucaa 20

<210> SEQ ID NO 95
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 2' fluoro nucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2' fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2' fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:

<221> NAME/KEY: modified_base
<222> LOCATION: (7)..(7)
<223> OTHER INFORMATION: 2' fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2' fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2' fluoro nucleotide
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2' fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2' fluoro nucleotide
<220> FEATURE:
<221> NAME/KEY: misc_feature
<222> LOCATION: (15)..(15)
<223> OTHER INFORMATION: may be modified by cholesterol-TEG-Glyceryl

<400> SEQUENCE: 95
gcgaagacuc cgaaa 15

<210> SEQ ID NO 96
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: may be modified by 5' inorganic Phosphate
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (2)..(2)
<223> OTHER INFORMATION: 2' fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2' fluoro nucleotide
<220> FEATURE:
<221> NAME/KEY: modified_base
<222> LOCATION: (5)..(5)
<223> OTHER INFORMATION: 2'-O-methyl nucleotide -continued

```
<220> FEATURE:
<221> NAME/KEY: modified_base
<222> LOCATION: (6)..(6)
<223> OTHER INFORMATION: 2' fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2' fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2' fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2' fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: misc_feature
<222> LOCATION: (14)..(20)
<223> OTHER INFORMATION: phosphorothioate linkages
<220> FEATURE:
<221> NAME/KEY: modified_base
<222> LOCATION: (14)..(14)
<223> OTHER INFORMATION: 2' fluoro nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2' fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2' fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2' fluoro nucleotide

<400> SEQUENCE: 96

uuucggaguc uucgcuguca                                        20
```